United States Patent
Davis et al.

(10) Patent No.: US 8,614,056 B2
(45) Date of Patent: Dec. 24, 2013

(54) MICROFLUIDIC METHOD FOR MEASUREMENT OR DETECTION INVOLVING CELLS OR BIOMOLECULES

(75) Inventors: Ronald W. Davis, Palo Alto, CA (US); Mehdi Javanmard, Fremont, CA (US); Michael N. Mindrinos, Menlo Park, CA (US); Janine A. Mok, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/070,002

(22) Filed: Mar. 23, 2011

(65) Prior Publication Data

US 2011/0312518 A1    Dec. 22, 2011

Related U.S. Application Data

(60) Provisional application No. 61/341,173, filed on Mar. 24, 2010.

(51) Int. Cl.
*C12Q 1/68*    (2006.01)

(52) U.S. Cl.
USPC ............................................................ 435/6

(58) Field of Classification Search
USPC ..................... 435/6.19, 7.1, 287.2; 422/503
See application file for complete search history.

(56) References Cited

U.S. PATENT DOCUMENTS

| | | | |
|---|---|---|---|
| 2002/0076690 A1 | 6/2002 | Miles et al. | |
| 2007/0151848 A1 | 7/2007 | Novak et al. | |
| 2009/0053732 A1 | 2/2009 | Vermesh et al. | |
| 2010/0075340 A1* | 3/2010 | Javanmard et al. | 435/7.1 |
| 2010/0120016 A1 | 5/2010 | Li et al. | |
| 2012/0196383 A1* | 8/2012 | Nitkowski et al. | 436/501 |

OTHER PUBLICATIONS

Javanmard M. et al. Electrical Detection of Proteins and DNA Using Bioactivated Microfluidic Channels. J of Vacuum Science & Technology B 27(6)3099-3103, 2009.*
Diercks A. et al. A Microfluidic Device for Multiplexed Prtoein Detection in Nano Liter Volumes. Analytical Biochemistry 386(1)30-35 Mar. 1, 2009.*
Verpoorte E. Beads and Chips: New Recipies for Analysis. Lab Chip 3:60N-68N, 2003.*
Javanmard, Mehdi, "Electrical Detection of Biomarkers Using Bioactivated Microfluidic Channels," Ph.D. Thesis, Sep. 2008.
Daniels, Jonathan S., et al., "Label-Free Impedance Biosensors: Opportunities and Challenges," Electroanalysis, May 16, 2007, 19(12): 1239-1257.
Javanmard, Mehdi, et al., "Targeted cell detection based on microchannel gating," Biomicrofluidics 1, 2007, 044103-1-044103-10.
Schoch, Reto B., et al., "Transport phenomena in nanofluidics," Review of Modern Physics, vol. 80, Jul.-Sep. 2008, 839-883.
Javanmard, Mehdi, et al., "A Microfluidic Platform for Characterization of Protein-Protein Interactions," IEEE Sens J. Aug. 2009, 9(8): 883-891.
Javanmard, Mehdi, et al., "Electrical detection of protein biomarkers using bioactivated microfluidic channels," Lab Chip, May 21, 2009, 9(10): 1429-1434.
Shinwari, M. Waleed, et al., "Microfabricated Reference Electrodes and their Biosensing Applications," Sensors 2010, 10, 1679-1715.

* cited by examiner

*Primary Examiner* — Ralph Gitomer
(74) *Attorney, Agent, or Firm* — David J. Aston; Peters Verny, LLP

(57) ABSTRACT

Embodiments of the invention are related to microfluidic devices for detecting or determining the concentration of biomolecules in an analyte comprising: a channel, wherein a surface of said channel is fabricated to be functionalized with at least one molecule selected to interact with a biomolecule, said channel being configured to interact with a microsphere, wherein a surface of said microsphere is fabricated to be functionalized with at least one same or different molecule selected to interact with said biomolecule; a second channel in fluid communication with said first channel; a system to move fluid containing said microsphere through said first and second channels; and a system to measure a change in electrical impedance or optical microscopy across said second channel as said microsphere moves through said second channel. Other embodiments concern related devices, and methods of making and using.

11 Claims, 43 Drawing Sheets

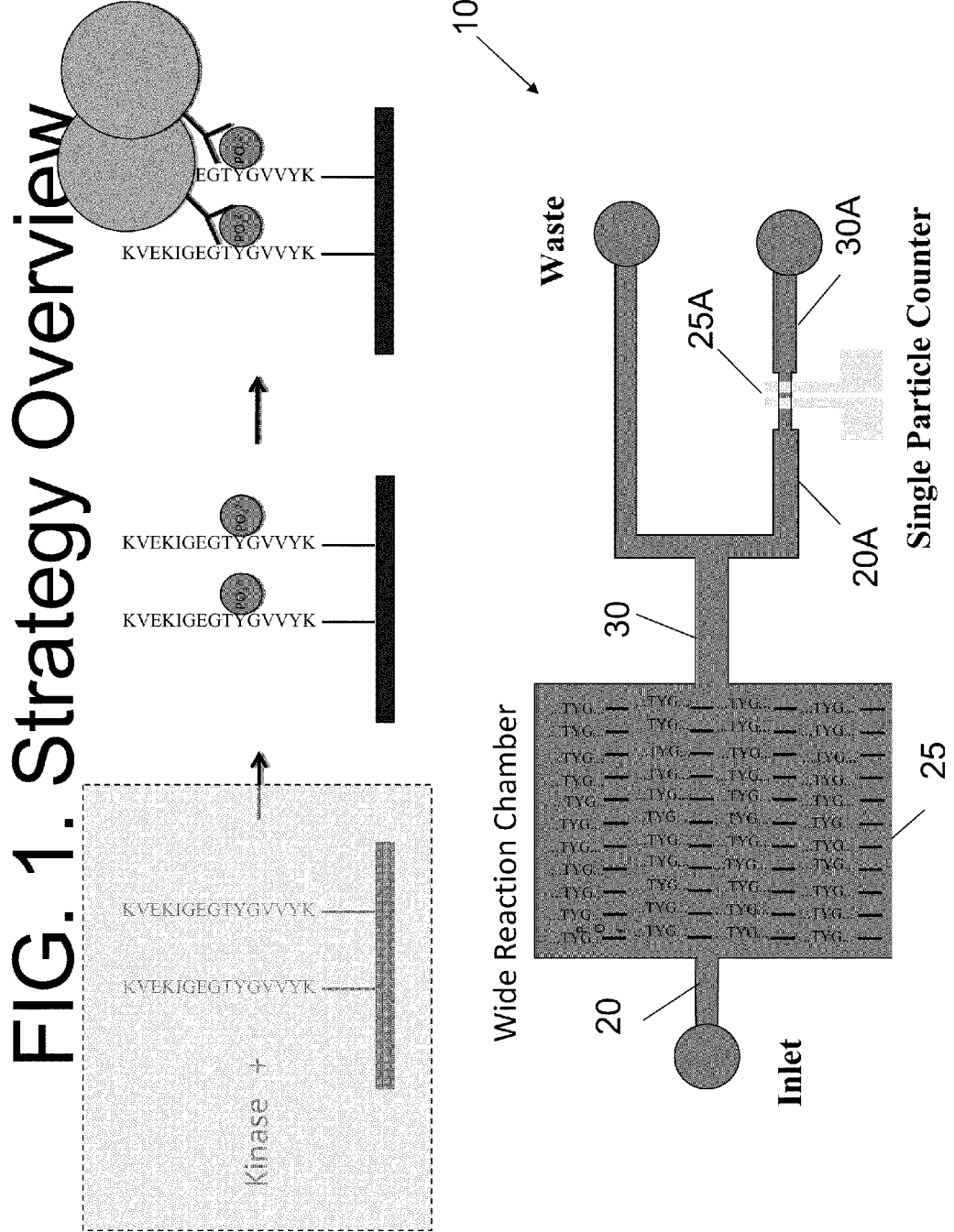

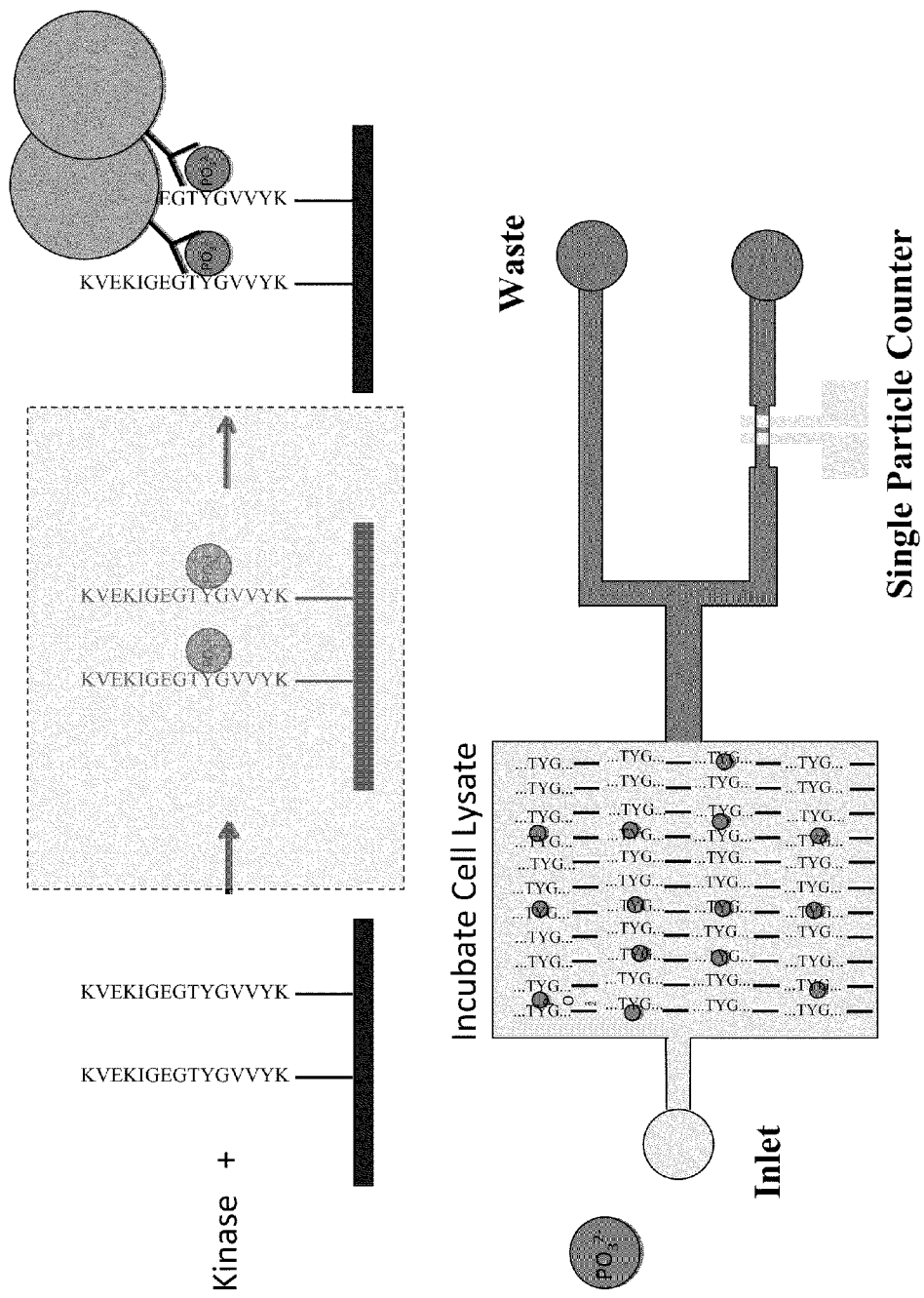
FIG. 2a. Incubate Cell Lysate

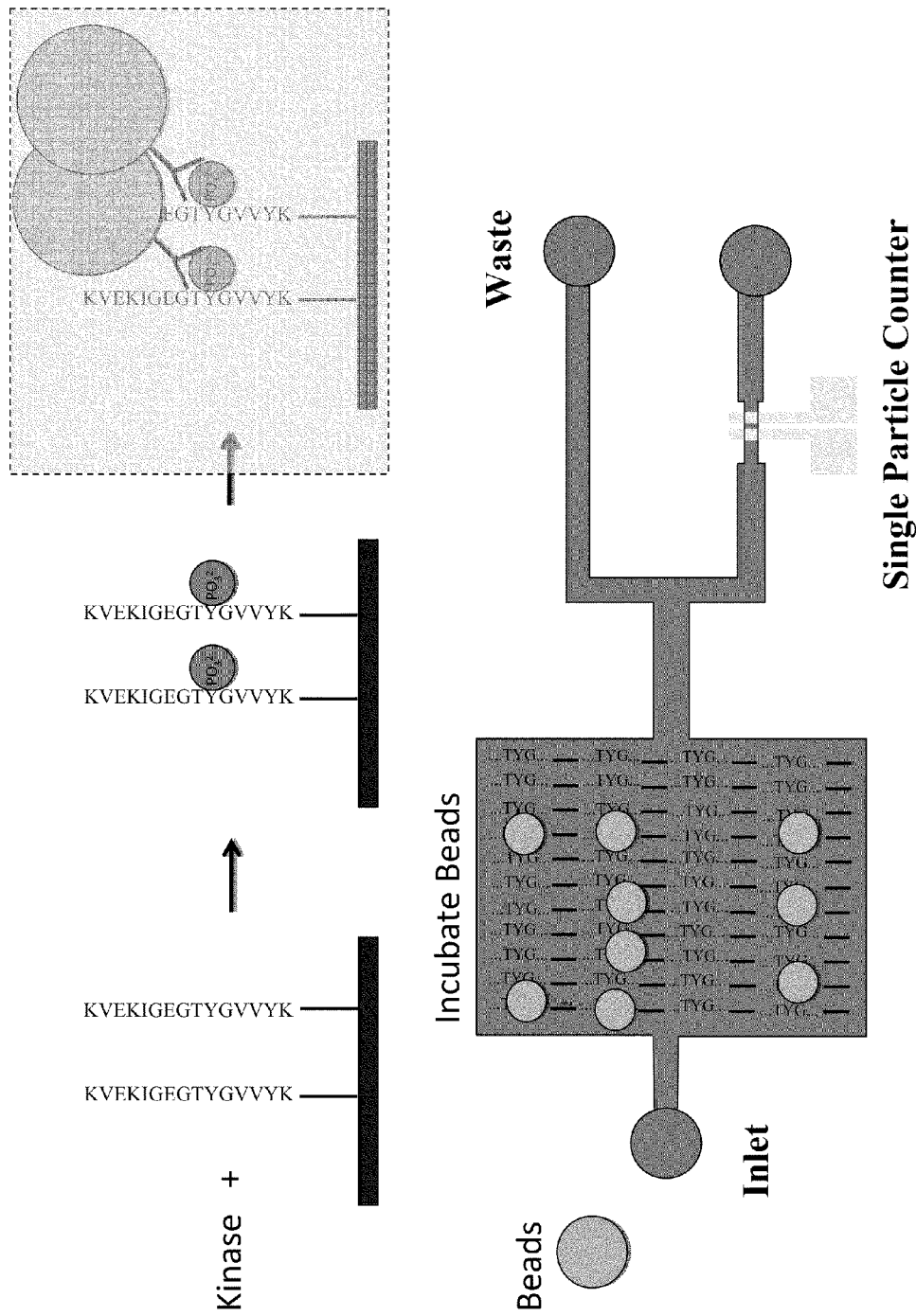
FIG. 2b. Incubate Beads

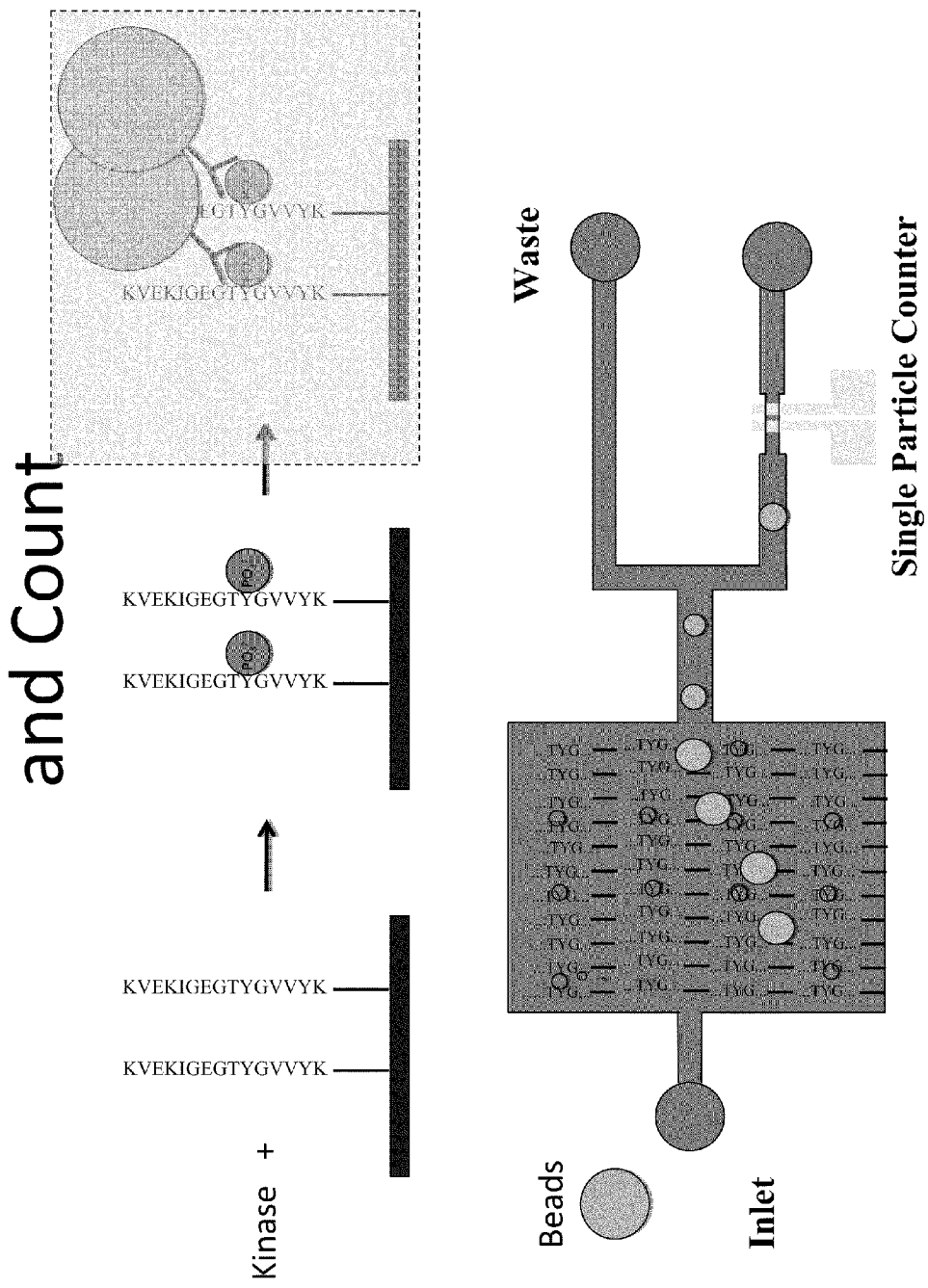

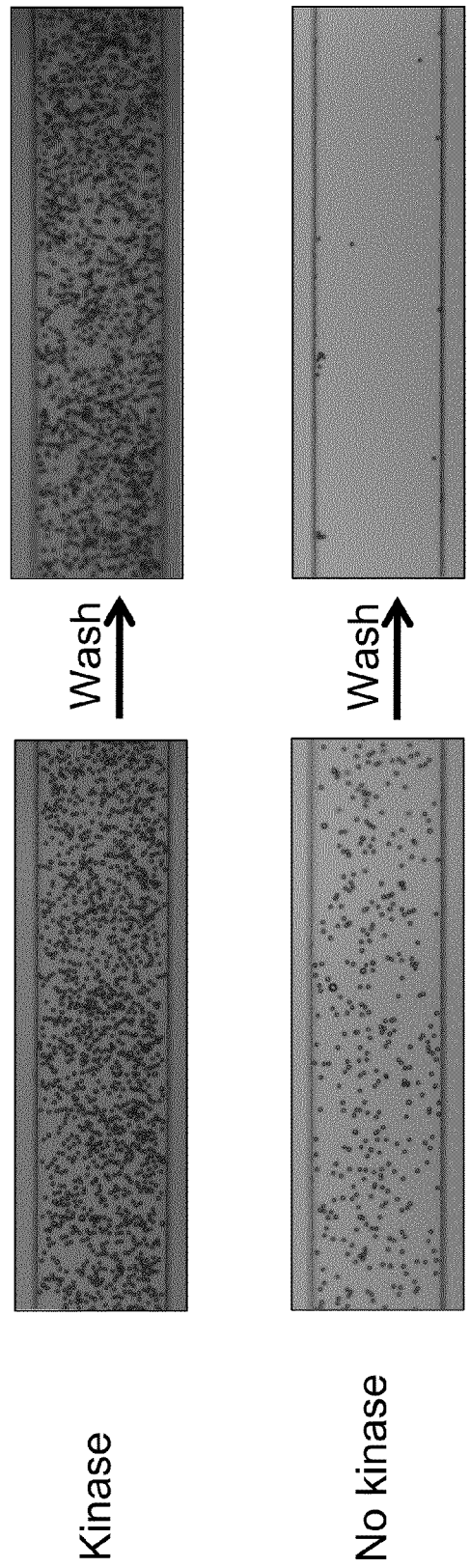
FIG. 3. Representative Results

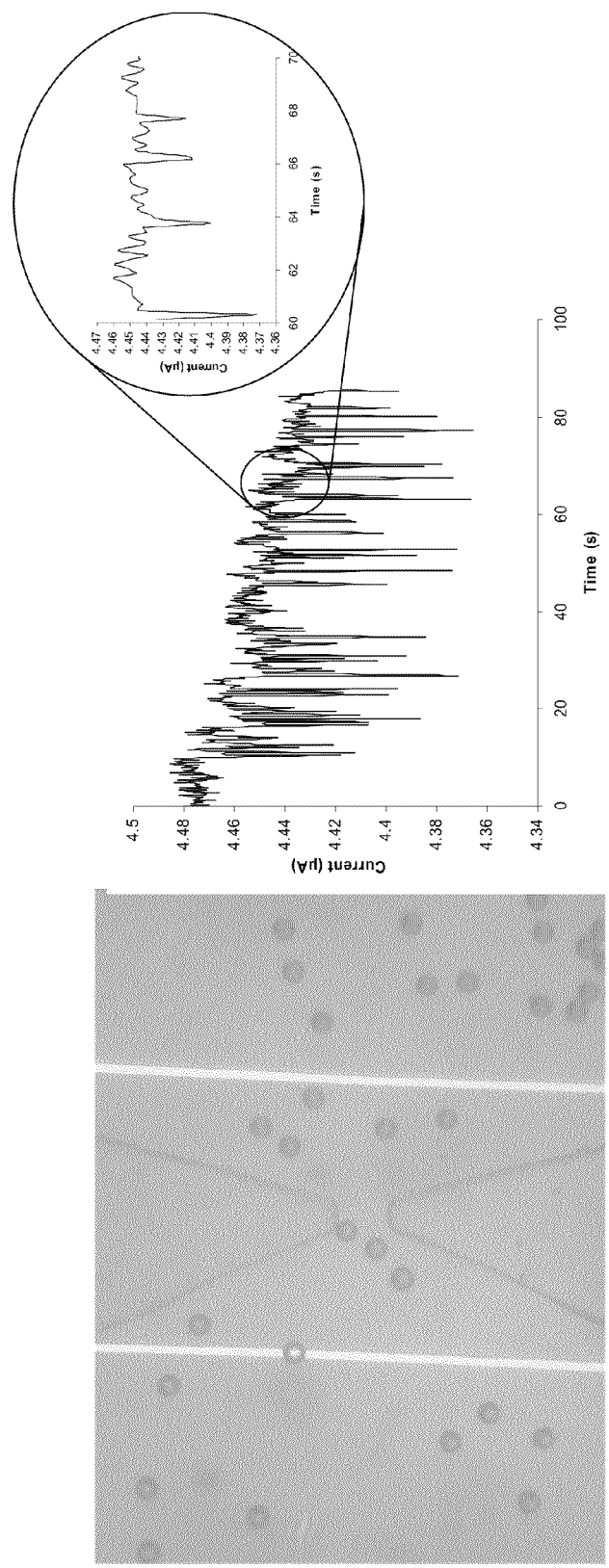
FIG. 4. Bead Counting

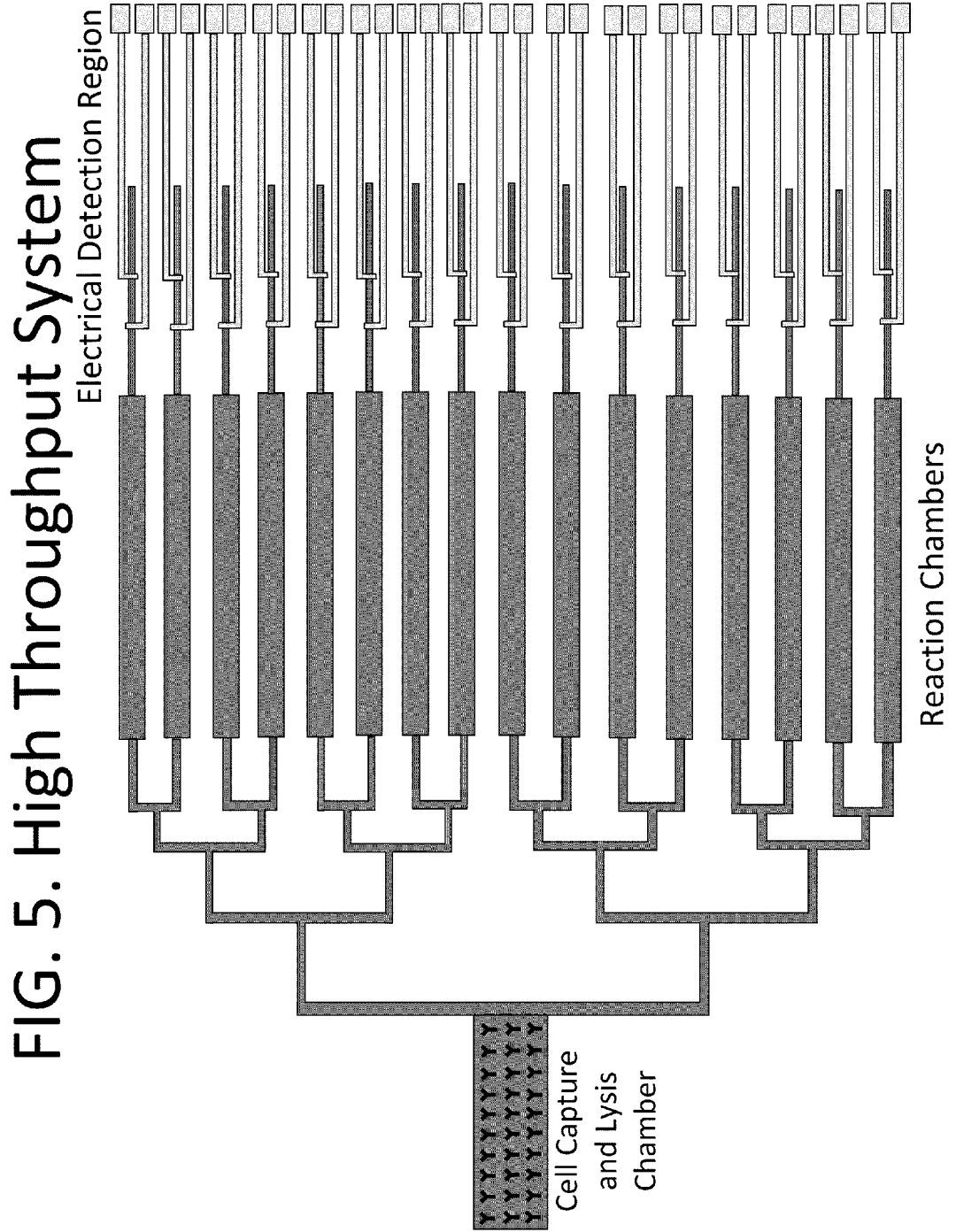

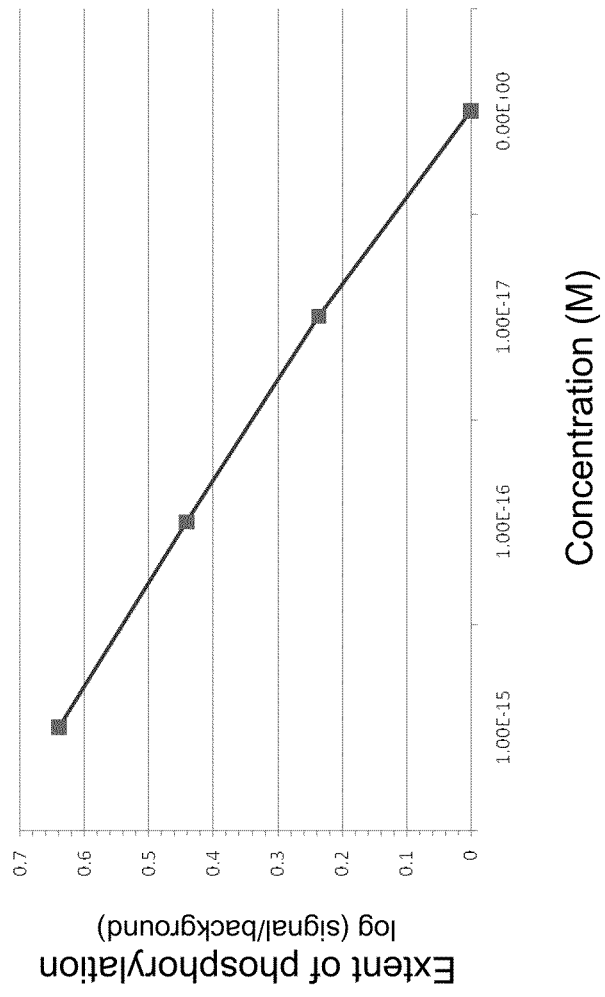
FIG. 6. Attomolar Detection

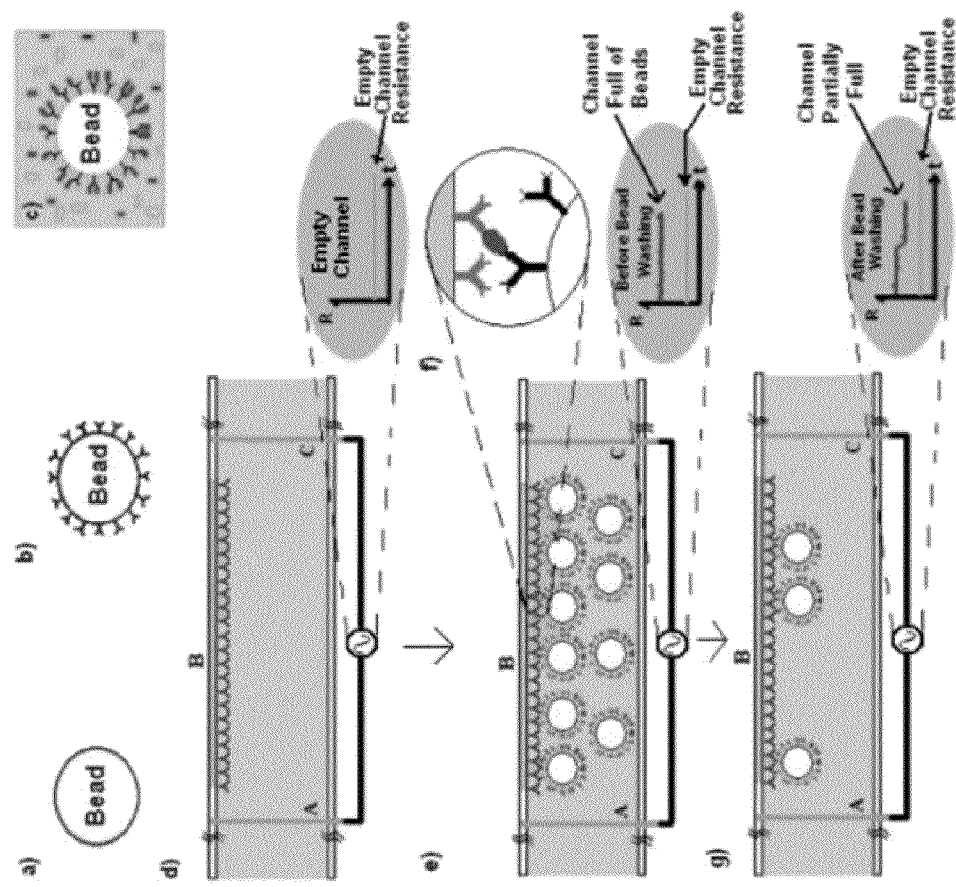

FIG. 9
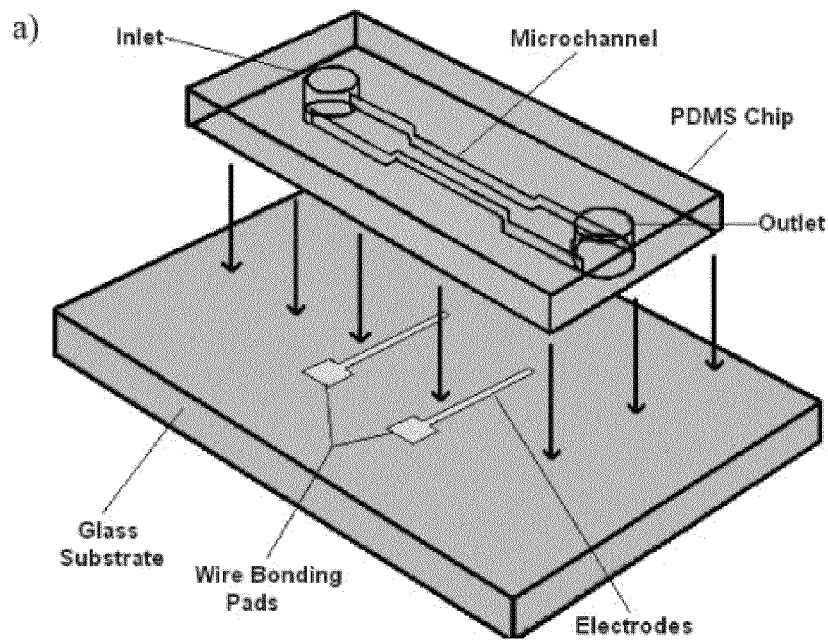
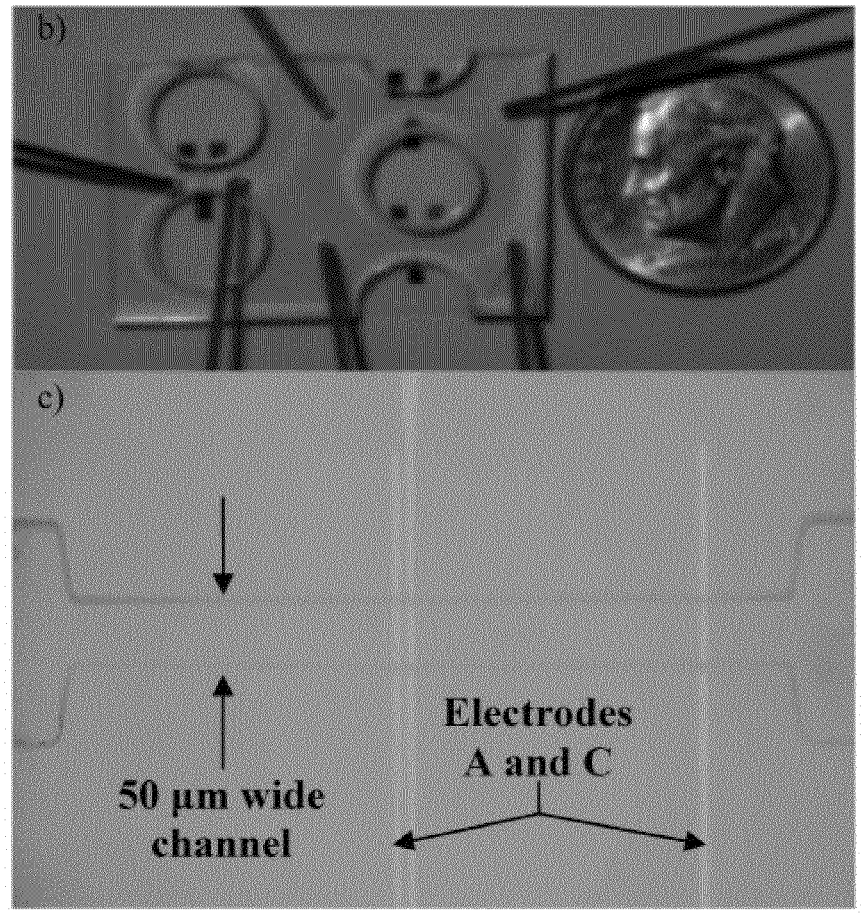

MICROFLUIDIC METHOD FOR MEASUREMENT OR DETECTION INVOLVING CELLS OR BIOMOLECULES

CROSS-REFERENCE TO RELATED APPLICATIONS

This application claims the benefit of U.S. Provisional Application No. 61/341,173, filed Mar. 24, 2010, which is incorporated herein by reference.

FEDERALLY-SPONSORED RESEARCH OR DEVELOPMENT

This invention was made with Government support under contract HG000205 awarded by the National Institutes of Health. The Government has certain rights in this invention.

STATEMENT REGARDING GOVERNMENT SUPPORT

This invention was made with Government support under contract 5P01GH-000205 awarded by the National Institutes of Health (NIH). The Government has certain rights in this invention.

BACKGROUND OF THE INVENTION

1. Field of the Invention

The field of the invention is measuring or detecting processes involving cells, nucleic acids, or proteins, including enzymes, devices therefor, and processes for forming such devices.

2. Description of Related Art

Current methods used for detection and quantification of protein biomarkers include techniques like the sandwich ELISA, an expensive technique requiring bulky optical equipment and also labeling of the proteins. The long incubation times required (several hours) make this a rather time consuming technique. Proteins are also separated and recognized using Western blotting, based on gel electrophoresis, also requiring labeling of the proteins, making it an expensive and time consuming technique due to the reagent preparation required and the long separation time. Western blotting is typically used in conjunction with mass spectrometry to recognize and analyze proteins.

Protein microarrays have also provided the ability for multiplexed quantification and detection. However, similar to all other fluorescence based detection techniques, protein microarrays require long incubation times and high reagent costs. The use of impedance based sensors for the detection of biomolecules eliminate the need for fluorescent labeling and also provide the opportunity for multiplexed analysis of biomolecules due to the ease of integrating CMOS (complementary metal oxide semiconductor), thus being a good candidate for the clinical setting.

Nanogap sensors have been used to demonstrate detection of proteins. Using techniques such as resistive pulse sensing, changes in the size of functionalized microspheres have been used for demonstrating multiplexed target protein biomarker detection at concentrations as low as 15 ng ml-1. With further optimization, it may be possible to decrease the detection limit by one or two orders of magnitude to achieve the detection limits required for cancer detection (4 ng ml-1 for PSA). Capacitive electrical biosensors, based on changes induced by target molecule and probe binding on the surface charge on the electrode-electrolyte interface, have also been reported for detection of DNA hybridization and protein biomarkers. However, consistency in the results is problematic for these types of sensors. Recently, the electrical detection of protein biomarkers at detection limits as low as 1 pg ml-1 has also been demonstrated using nanowires, however the sensor operates at very low salt concentrations, making it incompatible with physiological conditions in clinical samples like blood. Nanowires are also more difficult and expensive to fabricate making it an unsuitable candidate for the clinical setting in the near future. Detection of protein biomarkers and nucleic acid biomarkers has been demonstrated at the single molecule level using solid-state nanopores.

A rapid and inexpensive methodology for detecting the hybridization of two DNA strands can be useful in detecting the presence of certain genes in a patient's DNA. By detecting such gene sequences it is possible to determine whether a patient has predisposition to a certain type of disease allowing him to get treatment to prevent the disease. Currently DNA hybridization is detected using techniques such the use of DNA microarrays and also real-time PCR. Such techniques are expensive given that they require the use of fluorescent labels which result in high reagent costs. The other major cost comes from the use of expensive and bulky optical scanners required for reading the fluorescent signals. DNA hybridization also requires overnight incubation given that thousands of molecules must hybridize in order to produce enough optical signal to be readable by the fluorescent scanner.

The main challenge for rapid detection of a single bacterial cell lies in establishing a procedure which is ultrasensitive and can detect in real time, while, at the same time, being inexpensive and easy to use. Recently, many efforts have been made toward the use of impedance based sensors for detection of bacterial cells. Impedance based sensors are advantageous since they eliminate the need for fluorescence labeling. Several groups have reported pathogen detection using electrical impedance sensors. Many of the electrical impedance sensors presented (with some exceptions) to date require numerous washing steps and lack the ability for real-time detection. As for detection time, flow-cytometry based methods such as the use of coulter counters, have provided the ability to analyze the dielectric properties of a cell in real time. With the on-chip integration of microchannels and microelectrodes, the ability to count, sort, and trap cells and analyze their dielectric properties has been demonstrated. This type of device would operate on the principle of measuring the current change caused by the displacement in the fluid as the particle passes by two measuring electrodes. A device relying solely on this principle has difficulty in differentiating between two different types of cells which may have similar dielectric properties. Thus, this type of device would have difficulty in detecting a target cell in a complex mixture. The use of electroosmotic trapping when used in conjunction with impedance spectroscopy is a promising method for detection of targeted particles.

BRIEF SUMMARY OF THE INVENTION

A first embodiment is a microfluidic device for detecting or determining the concentration of biomolecules in an analyte comprising:

A channel, wherein a surface of said channel is fabricated to be functionalized with at least one molecule selected to interact with a biomolecule, said channel being configured to interact with a microsphere, wherein a surface of said microsphere is fabricated to be functionalized with at least one same or different molecule selected to interact with said biomolecule;

A second channel in fluid communication with said first channel;

A system to move fluid containing said microsphere through said first and second channels; and A system to measure a change in electrical impedance or optical microscopy across said second channel as said microsphere moves through said second channel.

A second embodiment is a microfluidic device for detecting or determining the concentration of nucleic acids in an analyte comprising:

A channel, wherein a surface of said channel is fabricated to be functionalized with at least one probe nucleic acid selected to hybridize with a target nucleic acid, said channel being configured to interact with a microsphere, wherein a surface of said microsphere is fabricated to be functionalized with at least one molecule selected to interact with said target nucleic acid;

A second channel in fluid communication with said first channel;

A system to move fluid containing said microsphere through said first and second channels; and A system to measure a change in electrical impedance or optical microscopy across said second channel as said microsphere moves through said second channel.

A third embodiment is a microfluidic device for detecting or determining the concentration of enzymes in an analyte comprising:

A channel, wherein a surface of said channel is fabricated to be functionalized with at least one substrate selected to be catalyzed by said enzyme, said channel being configured to interact with a microsphere, wherein a surface of said microsphere is fabricated to be functionalized with at least one molecule selected to interact with a product of catalysis of said substrate by said enzyme;

A second channel in fluid communication with said first channel;

A system to move fluid containing said microsphere through said first and second channels; and A system to measure a change in electrical impedance or optical microscopy across said second channel as said microsphere moves through said second channel.

A fourth embodiment is a microfluidic device for detecting or determining the concentration of enzymes in an analyte comprising:

A channel, wherein a surface of said channel is fabricated to be functionalized with at least one molecule selected to interact with a product of catalysis of a substrate by said enzyme, said channel being configured to interact with a microsphere, wherein a surface of said microsphere is fabricated to be functionalized with at least one substrate selected to be catalyzed by said enzyme;

A second channel in fluid communication with said first channel;

A system to move fluid containing said microsphere through said first and second channels; and A system to measure a change in electrical impedance or optical microscopy across said second channel as said microsphere moves through said second channel.

A fifth embodiment is a microfluidic device for detecting or determining the concentration of cells in an analyte comprising:

A channel, wherein a surface of said channel is fabricated to be functionalized with at least one molecule selected to interact with a biomolecule on a surface of a cell, said channel being configured to interact with said cell;

A second channel in fluid communication with said first channel;

A system to move fluid containing said cell through said first and second channels; and A system to measure a change in electrical impedance or optical microscopy across said second channel as said cell moves through said second channel.

A sixth embodiment is the device of the first embodiment, wherein said at least one molecule is an antibody and said at least one same or different molecule is a same or different antibody.

A seventh embodiment is the device of any of the first to the sixth embodiment, wherein said first channel is fabricated in polydimethylsiloxane (PDMS).

An eighth embodiment is the device of any of the first to the seventh embodiment, wherein said second channel is fabricated in polydimethylsiloxane (PDMS).

A ninth embodiment is the device of any of the first to the eighth embodiment, wherein a molded PDMS slab comprising said second channel is sealed to a glass chip with prefabricated electrodes.

A tenth embodiment is a single chip comprising a device or a plurality thereof of any of the first to the ninth embodiment.

An eleventh embodiment is a method for detecting or determining the concentration of biomolecules in an analyte comprising:

Moving fluid containing a microsphere through a microfluidic channel, wherein a surface of said channel is functionalized with at least one molecule selected to interact with a biomolecule, said channel being configured to interact with a microsphere, wherein a surface of said microsphere is functionalized with at least one same or different molecule selected to interact with said biomolecule, whereby said microsphere interacts said channel;

Moving fluid containing said microsphere upon elution from said first channel through a second microfluidic channel in fluid communication with said first channel; and Measuring a change in electrical impedance or optical microscopy across said second channel as said microsphere moves through said second channel.

A twelfth embodiment is a method for detecting or determining the concentration of nucleic acids in an analyte comprising:

Moving fluid containing a microsphere through a microfluidic channel, wherein a surface of said channel is functionalized with at least one probe nucleic acid selected to interact with a target nucleic acid, said channel being configured to interact with a microsphere, wherein a surface of said microsphere is functionalized with at least one molecule selected to interact with said target nucleic acid, whereby said microsphere interacts with said channel;

Moving fluid containing said microsphere upon elution from said first channel through a second microfluidic channel in fluid communication with said first channel; and Measuring a change in electrical impedance or optical microscopy across said second channel as said microsphere moves through said second channel.

A thirteenth embodiment is a method for detecting or determining the concentration of enzymes in an analyte comprising:

Moving fluid containing a microsphere through a microfluidic channel, wherein a surface of said channel is functionalized with at least one substrate selected to be catalyzed by said enzyme, said channel being configured to interact with a microsphere, wherein a surface of said microsphere is functionalized with at least one molecule selected to interact with a product of catalysis of said substrate by said enzyme, whereby said microsphere interacts with said channel;

Moving fluid containing said microsphere upon elution from said first channel through a second microfluidic channel in fluid communication with said first channel; and Measuring a change in electrical impedance or optical microscopy across said second channel as said microsphere moves through said second channel.

A fourteenth embodiment is a method for detecting or determining the concentration of enzymes in an analyte comprising:

Moving fluid containing a microsphere through a microfluidic channel, wherein a surface of said channel is functionalized with at least one molecule selected to interact with a product of catalysis of a substrate by said enzyme, said channel being configured to interact with a microsphere, wherein a surface of said microsphere is functionalized with at least one substrate selected to be catalyzed by said enzyme, whereby said microsphere interacts with said channel;

Moving fluid containing said microsphere upon elution from said first channel through a second microfluidic channel in fluid communication with said first channel; and Measuring a change in electrical impedance or optical microscopy across said second channel as said microsphere moves through said second channel.

A fifteenth embodiment is a method for detecting or determining the concentration of cells in an analyte comprising:

Moving fluid containing a cell through a microfluidic channel, wherein a surface of said channel is functionalized with at least one molecule selected to interact with a biomolecule on a surface of said cell, said channel being configured to interact with said cell, whereby said cell interacts with said channel;

Moving fluid containing said cell upon elution from said first channel through a second microfluidic channel in fluid communication with said first channel; and Measuring a change in electrical impedance or optical microscopy across said second channel as said cell moves through said second channel.

A sixteenth embodiment is the method of the eleventh embodiment, wherein said at least one molecule is an antibody and said at least one same or different molecule is a same or different antibody.

A seventeenth embodiment is the method of any of the eleventh to the sixteenth embodiment, wherein said first channel is fabricated in polydimethylsiloxane (PDMS).

An eighteenth embodiment is the method of any of the eleventh to the seventeenth embodiment, wherein said second channel is fabricated in polydimethylsiloxane (PDMS).

A nineteenth embodiment is the method of any of the eleventh to the eighteenth embodiment, wherein a molded PDMS slab comprising said second channel is sealed to a glass chip with prefabricated electrodes.

A twentieth embodiment is a multiplexing method comprising a method or a plurality thereof of any of the eleventh to the nineteenth embodiment.

BRIEF DESCRIPTION OF THE DRAWINGS

FIG. 1. Strategy overview. KVEKIGEGTYGVVYK is SEQ ID NO:1.

FIG. 2. (a) Incubate cell lysate. (b) Incubate beads. (c) Elute specifically bound beads and count. KVEKIGEGTYGVVYK is SEQ ID NO:1.

FIG. 3. Representative results.

FIG. 4. Bead counting.

FIG. 5. High throughput system.

FIG. 6. Attomolar detection.

FIG. 7. Schematic of microfluidic sensor for protein biomarkers. (a) Micron sized bead. (b) Bead coated with receptors. (c) Bead immersed in analyte. (d) Protein functionalized microchannel biosensor. (e) Beads loaded into microchannel biosensor. (f) Sandwich assay. (g) Flushed channel.

FIG. 9. (a) Schematic of microfluidic biochip. (b) Photograph of single chip. (c) Optical image of channel.

DETAILED DESCRIPTION OF THE EMBODIMENTS

Figure 8:
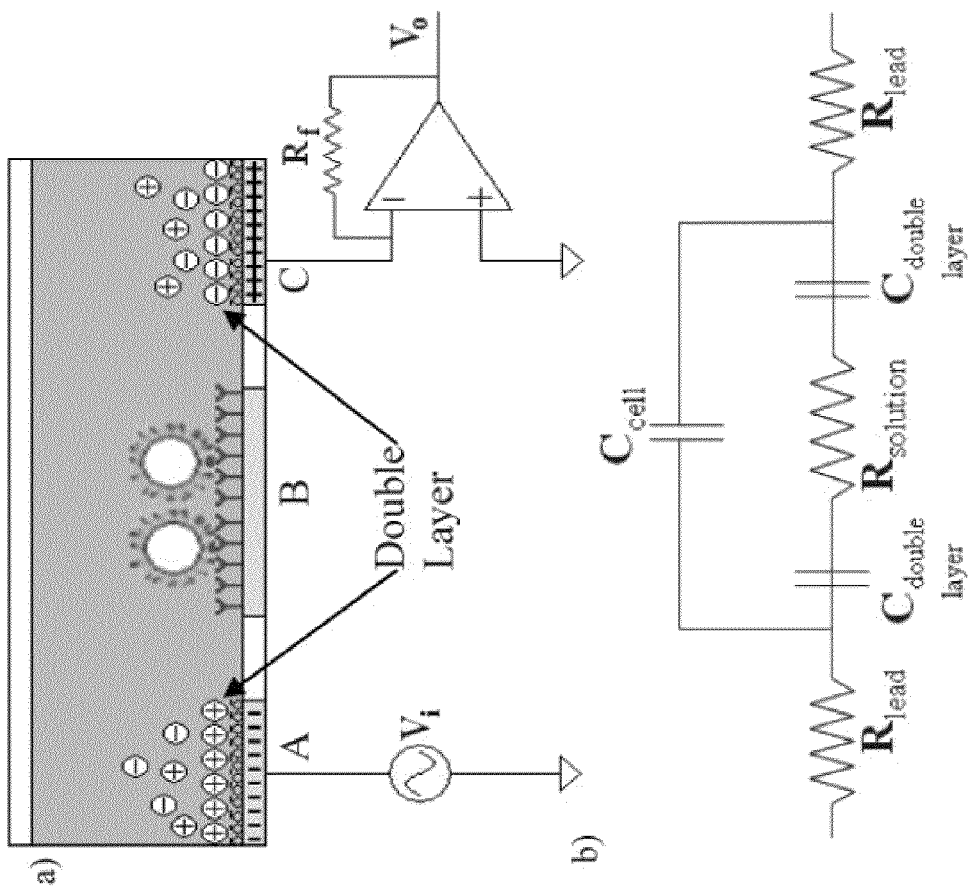
FIG. 8. (a) Side view cross section of microfluidic sensor. (b) An equivalent circuit.

Unless defined otherwise, terms used herein have the same meaning as commonly understood by one of ordinary skill in the art to which this invention belongs. See, e.g., Paul Singleton and Diana Sainsbury, *Dictionary of Microbiology and Molecular Biology* (3d ed. revised, John Wiley & Sons, Chichester, England, 2006).

Lab-On-Chips

The principle of the lab-on-chip (LOC) is to integrate all the necessary devices on a single small chip to perform complicated biological and chemical processes that are usually done with larger volumes in well-equipped laboratories. In the past ten years, the research and application in this area has been rapidly growing. After an initial focus on electrokinetic separation techniques on the chip, the scope of the technology has widened to include topics like microfluidics, DNA analysis, cell analysis, microreactors, and mass spectrometer interfacing. Microfabrication and the drive to analyze thousands or hundreds of samples quickly and efficiently have led to the development of this new form of analytical technology.

The idea of LOC is to have a bank of specialized modules that can be fitted together like building blocks to create a system, custom-tailored toward a specific application. The LOC would combine tiny channels, pumps, and storage chambers with electronic and optical devices, actuators and sensors to perform multi-step tasks. These systems, fabricated using technologies adopted from the microelectronics industry, are enabling researchers from many disciplines to approach their activities in new ways.

Microfluidics is the core technology that deals with the movement of small amounts of fluid. Subtechnologies would include electrophoresis, electrodynamics, semiconductor fabrication methods, labeling technology, laser fluorometry, and inkjet printing. A microfluidic device can be identified by the fact that it has one or more channels with at least one dimension less than 1 mm Microfluidics can handle common fluids such as whole blood samples, bacterial cell suspensions, protein or antibody solutions and various buffers; it is the key toward the development of microsynthesis, microseparations and lab-on-chips for sample preparation, rinsing, mixing, reaction, and other fluid processing needs for small volumes that cannot be performed in traditional ways.

The use of microfluidic devices to conduct biomedical research and create clinically useful technologies has a number of significant advantages. Because of the small volume, usually several nanoliters, the amount of reagents and analytes used is quite small. This is especially significant for expensive reagents. The microfluidic technologies for such devices are relatively inexpensive and are very amenable both to highly elaborate, multiplexed devices and also to mass production. One of the long-term goals in the field of microfluidics is to create integrated, portable clinical diagnostic devices for home and bedside use, thereby eliminating time-consuming laboratory analysis procedures.

Among the most important fluid handling components in a LOC are pumps and valves. There are two main methods by which fluid actuation through microchannels can be achieved: pressure driven and electroosmotic flow. In pressure driven flow, the fluid is pumped through the device via positive displacement pumps, such as syringe pumps, peristaltic pumps, etc.

The electroosmotic pumping is executed when an electric field is applied across the channel. The moving force comes from the ion moving in the double layer at the wall towards the electrode of opposite polarity, which creates motion of the fluid near the walls and transfer of the bulk fluid in convection motion via viscous forces.

Valves are often classified by whether they work by themselves (passive or check valves) or if they need an external energy to work (active valves).

The importance of mixing in a chemical/biological microsystem is obvious, particularly in a microreactor. Passive mixing in a microsystem solely depends on diffusion.

A LOC system mainly has four activities: sensing, actuation, heating, and processing. In analytical application, the sensors translate information from their environments into electrical signals. That information is then processed, either by the LOC itself, by a nearby integrated circuit, or by a computer. Thus, except pumps and valves, other functional components, such as injection, dosing, metering, sensing, and temperature measurement, actuators, and control/sensing circuit components, are all or partially needed in the LOC.

Protein Chips

Protein arrays (or chips), in comparison to DNA chips, represent a great technical advance, allowing thousands of proteins to be studied in a single experiment for the understanding of biological systems or system biology, in which protein plays a central role as most biological functions in organisms are mainly executed by protein.

Currently, protein microarrays can be divided into various types depending on the strategies to be chosen. Meanwhile, considering the field of application, protein microarrays can be classified into different categories: antibody array and antigen or reverse array, functional array, solute array, and others.

The principle of antibody arrays, and their converse counterparts, antigen or reverse arrays, is to use high affinity ligands to detect the presence of specific proteins and biomarkers in a complex mixture.

Functional arrays are concerned with elucidating novel protein interactions. These arrays are used to examine protein interactions with other ligands such as proteins, lipids, or other molecules. In addition, functional arrays are also used to determined enzyme activity and substrate specificity.

Solute arrays are described as containing coded microspheres in solution.

No matter what kind of biochip is chosen for use, the first and sometimes the most important step to construct a biochip is to effectively immobilize proteins or biomolecules on a solid surface. At present, a wide range of solid substrates are available for protein immobilization. According to the protein attachment strategies, namely, adsorption, affinity binding, and covalent binding, all these substrates can be separated into three main parts. Surfaces like polyvinylidene fluoride (PVDF), polydimethylsiloxane (PDMS), nitrocellulose, polystyrene, and poly-1-lysine coated glass can adsorb proteins by electrostatic or hydrophobic forces. A potential drawback of such substrates is the difficulty in preventing non-specific binding. To solve this problem, various blocking agents have been employed to saturate the free binding sites on the surface and thus reduce nonspecific binding.

Compared with the adsorption method, affinity binding can offer a strong and highly selective attachment through the use of specific biological interactions, for instance between biotin and avidin or between protein A and IgG. Note that both the surface and the protein to be attached should be derivatized with the components of the interaction.

Covalent binding is the most promising method for microarray technology for the reason that it provides the strongest attachment of proteins to surfaces. Most materials developed for covalent binding of proteins cannot be directly used unless their surfaces are functionalized. Normally, inorganic oxides, particularly silica, porous glass, and oxidized metals, are derivatized with organosilanes. The most popular examples are aminopropyltrimethoxysilane (APTES) treated glasses, silica, and quartz. Gold-based substrates are also widely investigated for covalent binding of probes. Except inorganic substrates, functionalized polymer membranes are another choice to immobilize proteins.

Electronic Biochips

Electronic biochips based on the detection of alterations in the electrical properties of an electrode arising from DNA hybridization and protein bindings have been extensively studied and developed.

Most fabrication techniques for silicon-based biochips have their roots in the standard manufacturing methods developed for the semiconductor industry. Currently, four basic fabrication steps are employed by the microchip manufacturers: (i) thin film deposition (ii) photolithography, (iii) etching, and (iv) substrate bonding.

In thin film deposition, a wide variety of techniques including chemical vapor deposition (CVD), thermal oxidation, physical deposition (sputtering, spin coating or E-beam), and electroplating are utilized to deposit thin films of different materials such as silicon, silicon nitride, silicon oxide, etc. onto a substrate.

Photolithography is used to transfer a computer-generated pattern onto a substrate. Here, a film of photoresist is spin-coated onto the substrate and exposed to UV light through a photolithographic mask; the light exposure transfers the desired pattern to the photoresist. Depending on whether the resist material is "positive" or "negative", the photoresist is developed by washing off the UV-exposed or -unexposed regions. When the substrate is subjected to chemicals, the photoresist would protect the surface below it and thus transfer the pattern to the substrate.

Lithography is always followed by an etching step in order to obtain a patterned film or selective material removal from the substrate. Etching can be divided into wet or dry etching.

Substrate bonding refers to bonding two substrates such as silicon-silicon, silicon-glass, and glass-glass to fabricate complex 3D structures. The two most popular bonding techniques are fusion bonding and anodic bonding.

Although optical detection techniques are perhaps the most prevalent in biology and life sciences, electronic or electro-chemical detection techniques have also been used in biochips due to their great sensitivity, high specificity, and low cost. These techniques can be amenable to portability and miniaturization, when compared to optical detection techniques. Electrochemical detection includes a type known as impedimetry, which measures conductance or capacitance changes associated with changes in the overall ionic medium between two electrodes.

Impedimetry measures the changes in the electrical impedance between two electrodes. The impedance changes at the electrode interface or in the bulk region can be used to identify biomolecular interreactions between DNAs, proteins, antigen-antibody bindings or microorganisms. Impedimetric techniques are attractive due to their simplicity and ease of use since an electrochemical label into the target molecule is not needed.

DNA Arrays

In a DNA array, gene-specific probes are created and immobilized on a chip (silicon wafer, nylon or glass array substrate). Biological samples are labeled, usually with fluorescent dyes or radioactivity. These labeled samples are then incubated with the probes to allow hybridizations to take place in a high fidelity manner. After incubation, non-hybridized samples are washed away and spot fluorescent or radioactivity signals resulting from hybridization can be detected.

DNA arrays are fabricated by immobilizing complementary DNA (cDNA) onto a solid substrate such as silicon, nylon or glass. This can be achieved by robotic printing of polymerase chain reaction (PCR) products (also known as direct-deposition approach), photolithographical synthesis of complementary oligonucleotides, or piezoelectric inkjet printing of PCR products (also known as indirect-deposition approach).

Microspheres

As used herein, microspheres are defined as any small amount of material capable of causing a change in electrical characteristic of a fluid (e.g., capacitance or conductance) when the fluid comprising microspheres flows through a microfluidic device. By way of example, but not by way of limitation, microspheres are any polymer particle, such as polystyrene particles or beads, metal colloids (e.g., gold colloidal particles), magnetic particles, dielectric particles, nanocrystals of materials, and bioparticles, etc. In embodiments of the invention, the microspheres are in the nanometer and/or micrometer size range, for example, but not limited to, from about 1 nm to about 100 µm.

Interactions

As used herein, interactions are defined as binding of a molecule to another molecule. For components A and B and the binding equilibrium $A+B \leftrightarrows AB$, the dissociation constant KD is given by $[A][B]/[AB]$, and it is smaller the tighter the binding between A and B. Herein, interactions mean binding with a $KD \geq \sim 10\text{-}5$ M-1, $KD \geq \sim 10\text{-}6$ M-1, $KD \geq \sim 10\text{-}7$ M-1, $KD \geq \sim 10\text{-}8$ M-1, $KD \geq \sim 10\text{-}9$ M-1, $KD \geq \sim 10\text{-}10$ M-1, $KD \geq \sim 10\text{-}11$ M-1, or $KD \geq \sim 10\text{-}12$ M-1.

Optical Detection

Although optical microscopy is eschewed in favor of electrical impedance, optical microscopy is another embodiment of the present invention. Detection of the microspheres can be performed optically without any label. Or the microspheres can be labeled with fluorochromes or be made of fluorescent material.

Charge Detection Using Single Electrode Charge Sensor

An alternative embodiment is detection of the microspheres by charge sensing using a single electrode charge sensor. Anderson, E. P. et al. 2008 *Sens Actuators B Chem.* 129(1): 79-86.

Magnetoresistive Detection

An alternative embodiment is detection of the microspheres by magnetoresistive sensing. Wang, H. et al. 2009 *International Solid-State Circuits Conference (ISSCC)* 25.6; Li, G. et al. 2003 *J. Appl. Phys.* 93: 7557.

Piezoresistive Pressure Detection

An alternative embodiment is detection of the microspheres by piezoresistive pressure sensing. Oosterbroek, R. E. et al. 1999 *Sensors and Actuators A: Physical* 77 (3): 167-177.

Single Molecule Sensing

An alternative embodiment is detection of a single molecule, e.g., a protein, a DNA, etc., instead of a microsphere, through a nanopore channel. Chang, H. et al. 2004 *Nano Letters* 4 (8): 1551-1556.

Simplified Embodiment of Present Invention

One embodiment of the present invention provides an apparatus for identifying individual biomolecules, as follows. FIG. 1 shows a simplified embodiment of the present invention. Specifically, device 10 comprises an input reservoir 20, an output reservoir 30, and a channel 25 connecting reservoirs 20 and 30.

A system is included to move fluid containing a microsphere from input reservoir 20 through channel 25 and into output reservoir 30.

A surface of channel 25 is functionalized with at least one molecule selected to interact with a biomolecule, the channel 25 is configured to interact with the microsphere passing through the channel 25, and a surface of the microsphere is functionalized with at least one same or different molecule selected to interact with the biomolecule.

Take an example. The surface of channel 25 is functionalized with a protein P1 (or other molecule). The surface of the microsphere is functionalized with a same or different protein P2 (or other molecule). The biomolecule will interact with protein P1 and P2 such that the microsphere interacts with channel 25 (as compared to the scenario of no biomarker, in which case the microsphere will pass therethrough).

In this embodiment of the present invention, device 10 comprises a second input reservoir 20A, a second output reservoir 30A, and a second channel 25A connecting second reservoirs 20A and 30A. The second channel is non-functionalized.

A system is included to move fluid containing the microsphere from second input reservoir 20A through second channel 25A and into second output reservoir 30A.

The second channel is in fluid communication with the first channel, and a system is included to move fluid containing the microsphere from the first channel into the second channel.

As such, the present invention also includes a system to measure the movement of the particle through the second channel.

It is to be understood that although the output reservoir of one channel may be directed into the input reservoir of a second channel, such two reservoirs may be one and the same; or they may instead be separated by a channel.

In one aspect, the second channel comprises a conduit through which a liquid suspension of microspheres to be sensed can be made to pass, wherein the conduit has an effective electrical impedance that is changed with the passage of each microsphere therethrough; and a measurement system for sensing the change of electrical impedance in the conduit.

In an alternative aspect, the second channel comprises a conduit through which a liquid suspension of microspheres to be sensed can be made to pass, wherein the conduit has an effective optical microscopy that is changed with the passage of each microsphere therethrough; and a measurement system for sensing the change of optical microscopy in the conduit.

The device is used to detect the presence of the individual microspheres in the second channel 25A. By determining the change in electrical impedance or optical microscopy as each individual microsphere passes through second channel 25A, it is possible to determine that interaction between the functionalized surface of the channel 25 and the functionalized surface of the microsphere has occurred as mediated by the biomolecule. Thus, in accordance with the present invention, it is possible to detect the presence and determine the concentration in an analyte of biomolecules.

It is to be understood that the above description is only exemplary and not limiting. For example, biomolecules can be replaced by cells, bacteria, viruses, and other microorganisms, and biomolecules themselves embrace a protein, a phospholipid, a sugar, a carbohydrate, and a peptidoglycan, DNA or RNA or any oligonucleotide chain. In addition, although the surface of channel 25 may be functionalized with a protein P1, it may more generally be functionalized by other molecules, including, but not limited to, a phospholipid, a sugar, a carbohydrate, a peptidoglycan, DNA or RNA or any oligonucleotide chain. Similarly, the surface of the microsphere may be functionalized with a protein P2, and may more generally be functionalized by other molecules, including, but not limited to, a phospholipid, a sugar, a carbohydrate, and a peptidoglycan, DNA or RNA or any oligonucleotide chain.

Electrical Detection of Kinase Activity

With the increasing popularity of personalized medicine, there continues to be needs to both identify biomarkers that are associated with disease phenotypes as well as develop methods to assay these biomarkers quickly and inexpensively. Despite the immense evidence implicating the role of kinases in disease, the use of kinase activity as a biomarker remains a relatively untapped area of research due to the lack of methods suitable for clinical applications. To this end, we are focused on developing the technology for an inexpensive assay capable of the rapid analysis of protein kinase activities in complex biological samples.

We have previously developed a microfluidic device capable of the electrical detection of protein biomarkers. In this technique, biomarker proteins are captured in microchannels functionalized with receptors for the targeted biomarker. Micron sized beads conjugated with different receptors for the targeted biomarker are then injected into the channel and allowed to bind the captured biomarker proteins. Using gold electrodes placed on either side of the channel, the ionic solution resistance across the channel is measured. As binding of the beads to the biomarker proteins will occlude the channel, the presence of protein biomarkers in an analyte can be detected by an increase in the resistance in the channel relative to baseline. With a one hour assay, this device has successfully been used to detect the presence of anti-hCG antibody at a concentration of at 1 ng/ml and a dynamic range of three orders of magnitude.

This technology has since been advanced to assay kinase activity in complex samples. To accomplish this, we have functionalized the microchannel with peptide substrates specific to a kinase of interest instead of receptors to a protein biomarker. Kinase reactions are performed on a chip, and any resulting phosphorylated peptides are then detected using beads that are conjugated with receptors specific to the phosphorylated peptide (e.g., anti-phosphotyrosine antibodies). As before, binding of the beads to the phosphorylated peptides will result in an increase in the ionic solution resistance and therefore be indicative of the presence of kinase activity. Preliminary work has now demonstrated that Src kinase activity can be detected using microchannels functionalized with a Src peptide substrate (15-mer corresponding to amino acids 6-20 of $p34^{Cdc2}$) and anti-phosphotyrosine conjugated beads.

Referring to FIG. 1, peptides specific to a target kinase are immobilized on a solid substrate. When the target kinase interacts with the peptide, it phosphorylates tyrosine residues. Beads coated with antibodies recognizing phosphorylated peptides attach to the peptide and serve to amplify the electrical signal.

We propose herein to improve the sensitivity of our device through a redesign that physically separates measuring the ionic resistance from bead binding as a correlate of the kinase reaction. In this next generation device, a flow rate is used to elute beads bound to phosphorylated peptides and direct them towards a second microchannel. Gold electrodes are placed on either side of this second microchannel to measure the ionic solution resistance across the microchannel. As each eluted bead passes through the active electrodes, there is a detectable increase in resistance across the microchannel relative to baseline. Thus, counting each change in resistance correlates to the number of beads bound to phosphorylated peptides, and in turn is indicative of the kinase activity in the sample assayed.

Hunter 2001 *Nature* 411 (6835): 355-365; Cohen, P. 2002 *Nat Cell Biol* 4 (5): E127-130). For example, the cell cycle checkpoint kinase Cdc2 has been shown to be improperly activated in colon, liver, and breast cancers (Ohta, T. et al. 1997 *Breast Cancer* 4 (1): 17-24; Kim, J. H. et al. 1999 *Cancer* 85 (3): 546-553; Li, K. K. et al. 2002 *Liver* 22 (3): 259-268). Similarly, loss of function mutations in PEK, a kinase involved in the ER unfolded protein response, has been correlated with Wolcott-Rallison Syndrome (WRS), a disease characterized by, among other symptoms, the onset of insulin-dependent diabetes in early infancy (Jiang, H. Y. et al. 2003 *Mol Cell Biol* 23 (16): 5651-5663; Wek, R. C., H. Y. Jiang, and T. G. Anthony 2006 *Biochem Soc Trans* 34 (Pt 1): 7-11). Kinases have naturally emerged as popular drug targets in the pharmaceutical arena (Noble, M. E., J. A. Endicott, and L. N. Johnson 2004 *Science* 303 (5665): 1800-1805; Garber, K. 2006 *Nat Biotechnol* 24 (2): 127-130).

Referring to the following table, kinases play an important role in disease.

| Kinase | Molecular Basis | Disease | Reference |
|---|---|---|---|
| ABL 1 | Translocation | Cancer (CML and ALL) | Chissoe, S. L. et al. 1995 *Genomics* 27(1): 67-82. |
| AKT 1 | Amplified, overexpression, activated | Cancer (breast, prostate, lung, colon, pancreatic, liver, ovary) | Carpten, J. D. et al. 2007 *Nature* 448(7152): 439-444. |
| ATM | Loss of function mutation | Ataxia telangiectasia (cancer and immune deficiency | Savitsky, K. et al. 1995 *Science* 268(5218): 1749-1753. |
| ATR | Mutation, splice change | Seckel Syndrome (dwarfism, mental retardation), cancer | O'Driscoll, M. et al. 2003 *Nat Genet* 33(4): 497-501; Alderton, G. K. et al. 2004 *Hum Mol Genet* 13(24): 3127-38; O'Driscoll, M. et al. 2007 *Am J Hum Genet* 81(1): 77-86. |
| KIT | Gain of function mutation, loss of function mutation, activated | Cancer and depigmentation | Hirota, S. et al. 1998 *Science* 1998 279(5350): 577-580; Longley, B. J. Jr. et al. 1999 *Proc Natl Acad Sci USA* 96(4): 1609-1614. |
| RHOK | Loss of function mutation | Type 2 Oguchi Disease (night blindness) | Hayashi, T. et al. 2007 *Ophthalmology* 114(1): 134-141. |
| SRC | Mutation, overexpression, activated | Cancer (breast, pancreas, colon, lung, ovary, CNS) | Irby, R. B. et al. 1999 *Nat Genet* 21(2): 187-190. |

We also anticipate and recognize translating this improved technology into a portable handheld device for clinical use. By multiplexing an array of microchannels, this device is able to assay clinically relevant complex mixtures, such as lysates prepared from primary tumors, for misregulated kinase activities and serve as an informative cancer diagnostic. While the redesign of this device is optimized to kinase activity, this technology is envisioned and recognized as being easily adapted to profile other enzymatic activities, as biomarkers for other diseases.

Its Significance

Phosphorylation represents one of the most important post-translational modifications found in all eukaryotes. With nearly 30% of the eukaryotic proteome estimated to be phosphorylated (Cohen, P. 2000 *Trends Biochem Sci* 25 (12): 596-601), it is not surprising that phosphorylation is involved in the regulation of virtually every basic cellular process (Hunter, T. 2000 *Cell* 100 (1): 113-127). Several studies have shown that many disease phenotypes are associated with the misregulation of kinase activity (Blume-Jensen, P. and T.

The close relationship of kinase activity with disease phenotypes strongly suggests the utility of kinase activity as a biomarker for disease diagnosis and monitoring of treatment. However, current methods to detect kinase activity are ill suited for clinical applications. Traditional kinase assays typically make use of radioactive isotopes (Witt, J. J. and R. Roskoski, Jr., 1975 *Anal Biochem* 66 (1): 253-258; Glass, D. B. et al. 1978 *Anal Biochem* 87 (2): 566-575). Radioactive assays can be expensive, demand special precautions to be followed when performing the assay, and generate waste that requires regulated disposal. In addition, the lack of known protein targets for kinases makes the detection of kinase activity within complex mixtures difficult. A kinase purification step in turn is usually necessary which, in addition to being time-consuming, is not always possible for clinical samples if an antibody is not available. Based on the embodiments herein, we have developed the technology suitable for the quick, inexpensive detection of the activity of a particular kinase present within a complex mixture and envisage and recognize demonstrating its utility in the clinical setting.

Device Theory for Kinase Detection

We have already developed a microfluidic device capable of electrical detection of protein biomarkers, DNA-DNA hybridizations, and target cells (Javanmard, M. et al. 2007 *Biomicrofluidics* 1 (4): 044103-044101; Javanmard, M. et al. 2009 *Sensors Journal, IEEE* 9 (8): 883-891; Javanmard, M. et al. 2009 *Lab on a Chip* 9 (10): 1429-1434). We have advanced this current technology to assay kinase activity in complex samples and improved upon its sensitivity by decoupling the reaction chamber from the electrical sensor. Referring to FIG. 2a, the device contains two regions. The first is a microfluidic chamber for the reaction to take place, and the second is a micropore integrated with electrodes. The reaction chamber is functionalized with peptide substrates specific to the kinase of interest. The cell lysate is injected into the chamber, so that the target kinase, if present, phosphorylates the peptides on the surface. Referring to FIG. 2b, beads that are conjugated with receptors to the phosphorylated peptides (e.g., anti-phosphotyrosine antibodies) are incubated in the reaction chamber, where they are captured. The nonspecifically bound beads are washed out of the chamber. Referring to FIG. 2c, the specifically bound beads are eluted from the surface and injected into the micropore that electrically counts the beads one by one as they pass through the electrical counter. The number of beads that have been counted is directly proportional to the number of peptides that have been phosphorylated, phosphorylation being directly proportional to the concentration of target kinase in the complex mixture. Thus this method is useful not only for kinase detection but for quantification as well. We also emphasize that while we are focusing on kinase detection, this technique is very general and is envisioned and recognized as being applied for many different applications like detection of protein biomarkers, nucleic acid hybridizations, and target cells.

Advantages to This Approach

The main advantage to this approach is that the reaction chamber and the detection chamber have been completely decoupled from each other. In the case of electrical biosensors, typically the capture step and detection step are both coupled to each other. This is undesirable, however, due to the fact that the constraints for designing an optimal detector contradict with that of an optimal chamber for enzymatic reaction or molecular capture. In order to maximize sensitivity of an electrical detector that transduces based on changes in resistance, one must make the channel as small as possible compared to the target molecule. In the case of reaction chambers or capture chambers, it is desirable to have as large of a probe functionalized surface as possible to maximize the number of interactions that will occur between target molecules in the buffer and the probe molecules immobilized on the surface. When trying to couple these two tasks together, one must compromise one over the other. Whereas when decoupling the two from each other gives a large degree of flexibility in tailoring each design to suit its own purpose.

Representative Results

We have demonstrated the ability to electrically detect kinase activity using the first generation device with Src as the target protein kinase. Src is a non-receptor tyrosine kinase known to be activated in many cancers, including colon cancer (Irby, R. B. et al. 1999 *Nat Genet* 21 (2): 187-190). The surface of the microchannel was coated with peptides of a sequence specific to Src (KVEKIGEGTYGVVYK) (SEQ ID NO:1). Anti-phosphotyrosine antibodies, which have a specific affinity to phosphorylated peptides, were adsorbed to protein G functionalized beads of various sizes (800 nm and 7 μm). Various concentrations of Src kinase suspended in buffer were injected into the functionalized microchannel at a slow yet continuous flow rate for 1 hour.

After a one hour kinase reaction and several washes, the antibody conjugated beads were injected into the chamber and incubated for one minute such that they had sufficient time to settle. Then a flow rate of 90 nl/min was applied across the channel to remove the beads that were not specifically bound to the surface of the active area of the sensor. Referring to FIG. 3, the top reproduction illustrates representative images of our Src protein kinase reaction using 7 μm beads both before and after washing. The bottom reproduction illustrates representative images of a negative control reaction (no kinase) performed in parallel both before and after washing.

Referring to FIG. 4, this figure illustrates representative data of beads being counted in our micropore. The beads were injected into the microchannel at a flow rate of 175 nl/min An optical micrograph showing the beads passing through the channel is shown on the left. The current was monitored across the micropore as shown on the right. The downward spikes correspond to beads passing through the channel. By these experiments, we have demonstrated proof of concept for our technique with polystyrene beads, resulting in a detection limit of 100 fM.

Future Optimization

We have demonstrated the proof of concept for our technique's ability in detecting kinase activity. We envision and recognize optimizing the device parameters to achieve sensitivity at the attomolar level. Optimization of the geometry and parameters of the microfluidic capture chamber, the electronic micropore used for counting, and the detection circuitry to maximize the detection limit is empirical and well within the level of skill in the art. We also anticipate and recognize demonstrating multiplexed detection (FIG. 5). Referring to FIG. 5, a waste channel can also be added to each reaction chamber to flow out the nonspecifically bound beads, but this is unnecessary as they can be washed out through the electrical detection region before the counting begins. Finally, we contemplate and recognize working towards fabricating a fully integrated microfluidic biosensor with a complementary metal oxide semiconductor (CMOS) integrated circuit, resulting in a handheld device suitable for point of care diagnostics.

Protein Biomarkers[1]

[1] To repeat, we have already developed a microfluidic device capable of electrical detection of protein biomarkers. Javanmard, M. et al. 2009 *Lab on a Chip* 9 (10): 1429-1434. We have advanced this current technology and improved upon its sensitivity by decoupling the capture chamber from the electrical sensor. Adaptation is empirical and well within the level of skill in the art given the present disclosure.

Current methods used for analyzing biomarkers involve expensive and time consuming techniques like the Sandwich ELISA which require lengthy incubation times, high reagent costs, and bulky optical equipment. We have developed a technique involving the use of a microchannel with integrated electrodes, functionalized with receptors specific to target biomarkers. We have applied our biochip to the rapid electrical detection and quantification of target protein biomarkers using protein functionalized microchannels. We successfully demonstrate detection of anti-hCG antibody, at a concentration of 1 ng ml-1 and a dynamic range of three orders of magnitude, in less than one hour. We envision and recognize the use of this technique in a handheld device for multiplex high throughput analysis using an array of microchannels for probing various protein biomarkers in clinically relevant samples such as human serum for cancer detection.

Protein Biomarker Detection with Bioactivated Microchannel

In the microchannel gating technique for protein biomarker detection, micron sized beads (FIG. 7a) are coated with primary receptors (FIG. 7b) and then the targeted protein biomarker is captured as the functionalized beads are immersed in a multianalyte solution (FIG. 7c). Presented in FIG. 7d is the protein functionalized microchannel biosensor, with gold electrodes labeled A and C. Protein receptors with affinities to target biomarkers are immobilized on the surface of the channel between electrodes A and C. The region between these two electrodes is the active region of the channel in which the ionic solution resistance is measured. Gold electrodes are very suitable for surface chemistry modifications, such as deposition of surface assembled monolayers, which will optimize the immobilization of the receptors. The beads are then injected into the microchannel (FIG. 7e) partially occluding the channel resulting in a resistance higher than the baseline value. If any of the bead surfaces are labeled with the targeted biomarkers, the beads will attach to the receptors on the channel wall. After the beads have come to rest, a flow is applied across the channel causing the unbound beads to be washed out of the channel, resulting in a drop in the ionic solution resistance depending on the number of beads remaining (FIG. 7g). The number of beads remaining attached is proportional to the targeted protein biomarker concentration. A high concentration of target biomarkers will result in a smaller drop in resistance compared to a low concentration of biomarkers. Thus, in addition to being able to detect the presence of protein biomarkers at low concentration, this sensor also provides the ability of measuring the concentration of the target biomarker.

Referring to FIG. 7, to recap, (a) shows a micron sized bead. (b) shows a bead coated with receptors and then (c) immersed in a multianalyte solution. (d) shows a protein functionalized microchannel biosensor. (e) shows the beads labeled with targeted biomarkers, in a phosphate buffered saline (PBS) solution (138 mM NaCl, 2.4 mM KCl) with a pH of 7.4, loaded into the channel and allowed to bind to the secondary receptor molecules which are immobilized on the gold electrode forming a (f) sandwich assay at the channel surface (top plot). (Bottom plot) shows the prediction of resistance across electrodes A and C after injection of beads. (g) shows the channel is then flushed, causing the unbound beads to be removed from the channel. The magnitude of the resistance change across electrodes A and C is proportional to the target biomarker concentration.

The requirement for successful detection of the target biomarker is that the surfaces of the microspheres contain primary receptors and that the active area of the sensor contains secondary receptors, both of which should be specific to the targeted biomarker. It is also necessary that the microspheres used be comparable in size to that of the channel geometry.

Electrode Electrolyte Interface

The physical processes occurring at the interface between the electrode and the electrolyte and also the bulk solution directly dictate the impedance behavior of the channel. FIG. 8a shows a side view cross section of the device. The gold electrode surfaces are assumed to be hydrophilic. An equivalent circuit network (FIG. 8b) based on the parasitic resistances and capacitances between electrodes A and C (electrode B is floating) can be used to describe the impedance behavior. The small separation of the layer of accumulated ions (FIG. 8a) on electrodes A and C results in the double layer capacitance, C double layer which is measured to be approximately 0.4 nF for our system, dominating the impedance at low frequencies. Effects such as the Warburg impedance and the electron transfer resistance also significantly affect the impedance at low frequencies. We did not include either of these two parasitic impedances in our equivalent circuit model since they are negligible at the frequencies which we operate. Due to the large separation, the capacitance between the electrodes A and C, C cell, is negligible. Given that we want to detect the presence of the microspheres due to the resulting change in channel resistance, we want to minimize the effect on the impedance measurement resulting from all impedances except for the bulk solution resistance, R solution. This can be achieved by working at sufficiently high frequencies. From our previous work, we measured the onset of bulk solution resistance dominating the impedance at frequencies above 20 kHz. Bulk solution resistance levels were measured to be approximately 80 KΩ with a salt concentration of 138 mM NaCl. We found approximately 30 kHz to be an optimum frequency to operate our device, because at frequencies below this, the impedance due to the double layer capacitance had not yet completely diminished, however as the frequency of the excitation voltage signal was increased above 30 kHz, the output signal became noisier.

Referring to FIG. 8, (a) shows a side view cross section of a microfluidic sensor. Positive and negative circles represent positive and negative ions accumulating at the surface of electrodes A and C. Electrode B is floating. A function generator is tied to the left electrode and a current pre-amplifier is tied to the right electrode, which is used to measure the current across the channel. (b) shows an equivalent circuit used in our system for understanding the impedance behavior as a function of frequency.

Device Design

The microfluidic biochip used in this study is shown in FIG. 9a. Experiments were conducted on microchannels of various sizes 10 μm deep and 20 μm wide, and 50 μm deep and 50 μm wide channels (FIG. 9c). For smaller channel sizes, channel clogging and nonspecific binding was problematic, so the larger channel sizes were used.

Referring to FIG. 9, (a) shows a schematic of a microfluidic biochip. A PDMS chip and glass chip are bonded together. (b) shows a photograph of a single chip containing three different channels with integrated electrodes. (c) shows an optical image of a 50 μm channel with three electrodes. Resistance is measured between electrodes A and C. Electrode B is not used in this study.

Fabrication

Au/Cr electrodes (2000 Å/150 Å) were micropatterned on a glass wafer using traditional photolithography, sputtering, and then lift-off processing and then cut into separate chips using a wafer saw. The microchannels were fabricated in PDMS.

The master mold for the microchannels was patterned onto a silicon substrate using SU-8 photoresist. PDMS (10:1 prepolymer:curing agent) was poured onto the master mold and allowed to cure. The glass chips and the PDMS slabs were aligned and then bonded together after oxygen plasma treatment.

Measurement Apparatus

Electrical impedance measurements were collected across the channel in the region between electrodes A and C. We applied a voltage signal to electrode A and a low noise current pre-amplifier (Stanford Research Systems Model SR570) to electrode C in order to measure the current across the channel and then the data were collected with a National Instruments data acquisition card and read by a Labview program. The channels were also monitored using optical microscopy in order to confirm that the electrical signal changes were due to beads binding in between the electrodes.

Microsphere Preparation

Anti-rabbit IgG, which has a specific affinity to rabbit anti-hCG antibody, was used as the primary receptor which was physically adsorbed onto 10 μm polystyrene beads (Bangs Labs, Wis.). The microspheres were suspended in 50 μl of PBS buffer at a concentration of 11.8 mg ml-1. 10 μl of anti-rabbit IgG (Sigma Aldrich, St. Louis, Mo.), at a concentration of 5 μg ml-1, was added to the bead solution, and incubated in a rotator for 45 min in order to prevent precipitation. The solution was then centrifuged, the supernatant was removed, and the beads were again resuspended in PBS. This process was repeated three times in order to ensure that all free antibodies were removed from the solution.

Channel Surface Bioactivation

Anti-rabbit IgG was also used as the secondary receptor which was physically adsorbed onto the base of the microfluidic channel. Anti-rabbit IgG diluted in PBS solution to 5 μg ml-1 was injected into the channel and incubated for 15 min The microchannel surface was then coated with a blocking buffer, 1 mg ml-1 bovine serum albumin (BSA) in order to minimize nonspecific interactions. BSA solution was injected into the channel and incubated for 10 min Since the probe molecules could be physically adsorbed onto the glass base of the channel, the use of a channel with a wide floating electrode (electrode B) in between the active electrodes (A and C) was unnecessary.

Anti-hCG Antibody Assay

For the test sample, PBS solution was spiked with various concentrations of anti-hCG antibody ranging from 10 pg ml-1 to 1 μg ml-1. The functionalized beads were immersed in the test sample, and placed in a rotator for 45 min to capture target proteins in the sample. Anti-rabbit IgG molecules capture anti-hCG antibodies based on an interaction which occurs between the Fab region of the anti-rabbit IgG and an epitope located on the Fc region of the anti-hCG antibody. The solution was then centrifuged, then resuspended in PBS. This process was repeated three times in order to ensure that the free target protein molecules were removed completely from the solution.

The bead solution was injected into the microchannel and incubated for 1 min to allow the beads which captured the target protein to bind to the base of the channel forming a sandwich assay. Fluids were injected into the channel, and the flow rates were controlled using a pressure driven Harvard Apparatus Model 11 syringe pump (Instech Solomon, Plymouth Meeting, Pa.). A flow rate of 50 nl min-1, which was experimentally determined to be the minimum flow rate required to wash off the nonspecifically bound beads, was then applied to the microchannel in order to flush out the unbound beads. The number of beads before and after the washing was counted manually, and the electrical impedance was recorded simultaneously.

Results and Discussion

In order to demonstrate the ability of our technique to detect the target biomarker, we performed real-time electrical measurements. We looked at the percentage drop in resistance across the channel after washing. The percent change provides information as to how many beads are removed from the channel as compared to how many were present before the washing step. The electrical measurements are shown in real-time (FIG. 10a) as the channel was washed. As the flow was applied to the channel, the unbound beads are flushed out of the channel. As the concentration of the target protein biomarker decreases, the drop in the electrical impedance increases. The decrease in the target biomarker concentration results in more beads being removed from the sensing area of the channel (FIG. 10a), thus resulting in a larger drop in impedance across the electrodes. When the target concentration is 1 μg ml-1, almost all of the beads remain attached (FIG. 10b) corresponding to no change in the impedance after washing. In the scenario where no target protein was present in the test sample, almost all of the beads were removed from the base of the channel, with the exception of a few which remain attached due to nonspecific binding. This corresponds to the largest drop in impedance (FIG. 10c).

Figure 10:
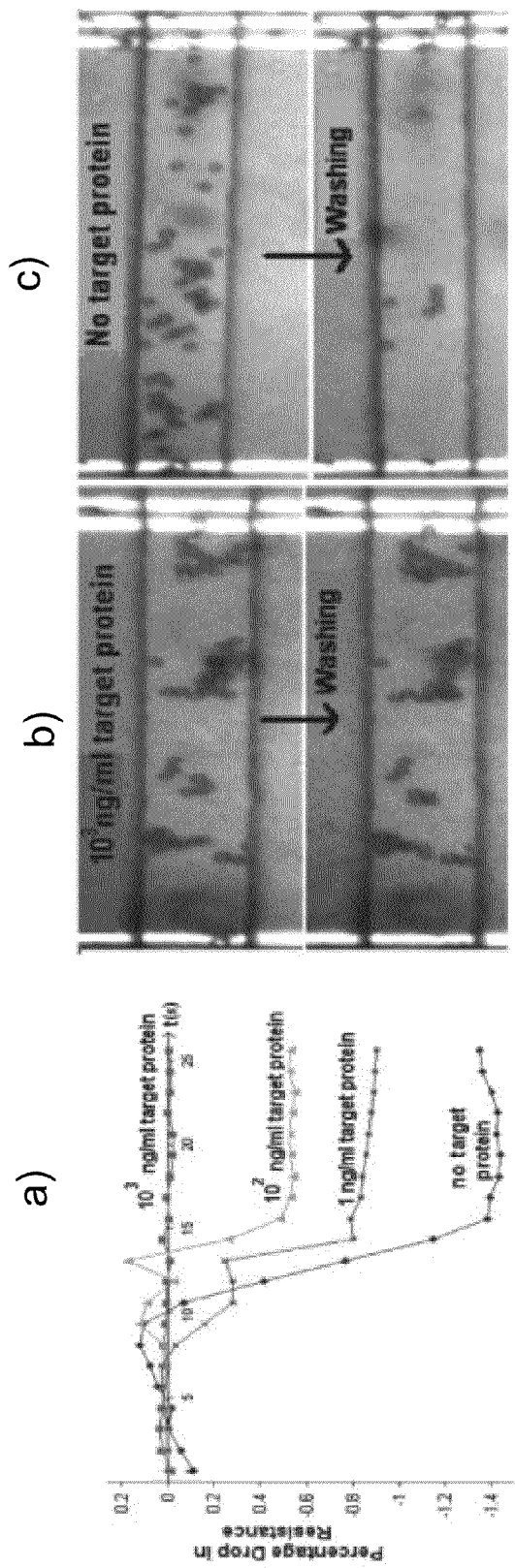
FIG. 10. (a) Percentage drop in resistance as a function of time. (b) High concentration of target protein. (c) No target protein.

Referring to FIG. 10, a) shows the percentage change in resistance as a function of time. The real time drop in resistance increases as the concentration of target protein biomarker decreases. (b) shows a high concentration of target protein results in almost all beads remaining bound after washing. (c) shows no target protein in test sample results in almost all beads being washed off.

We analyzed the ability of this technique to quantify target protein biomarkers in detail by performing this assay over a wide range of target protein concentrations. The assay was confirmed optically (FIG. 11a), where the beads in the channel were counted before and after washing. The standard error bars for over five different experiments for each data point is included. A dynamic range of three orders of magnitude and a repeatable detection limit of 1 ng ml-1 (7 pM) are demonstrated. The average percentage decrease in electrical resistance measured as a function of target biomarker concentration is shown (FIG. 11b) confirming the optical results (FIG. 11a). Decrease in target biomarker concentration results in more beads being removed from the sensing area of the channel, thus resulting in a larger drop in resistance across the electrodes. As a control experiment, we tested the case where no target protein biomarkers were present in the test sample, which resulted in an average capture of less than 4% of the beads due to nonspecific binding of the beads, and a 0.5% drop in impedance.

Figure 11:
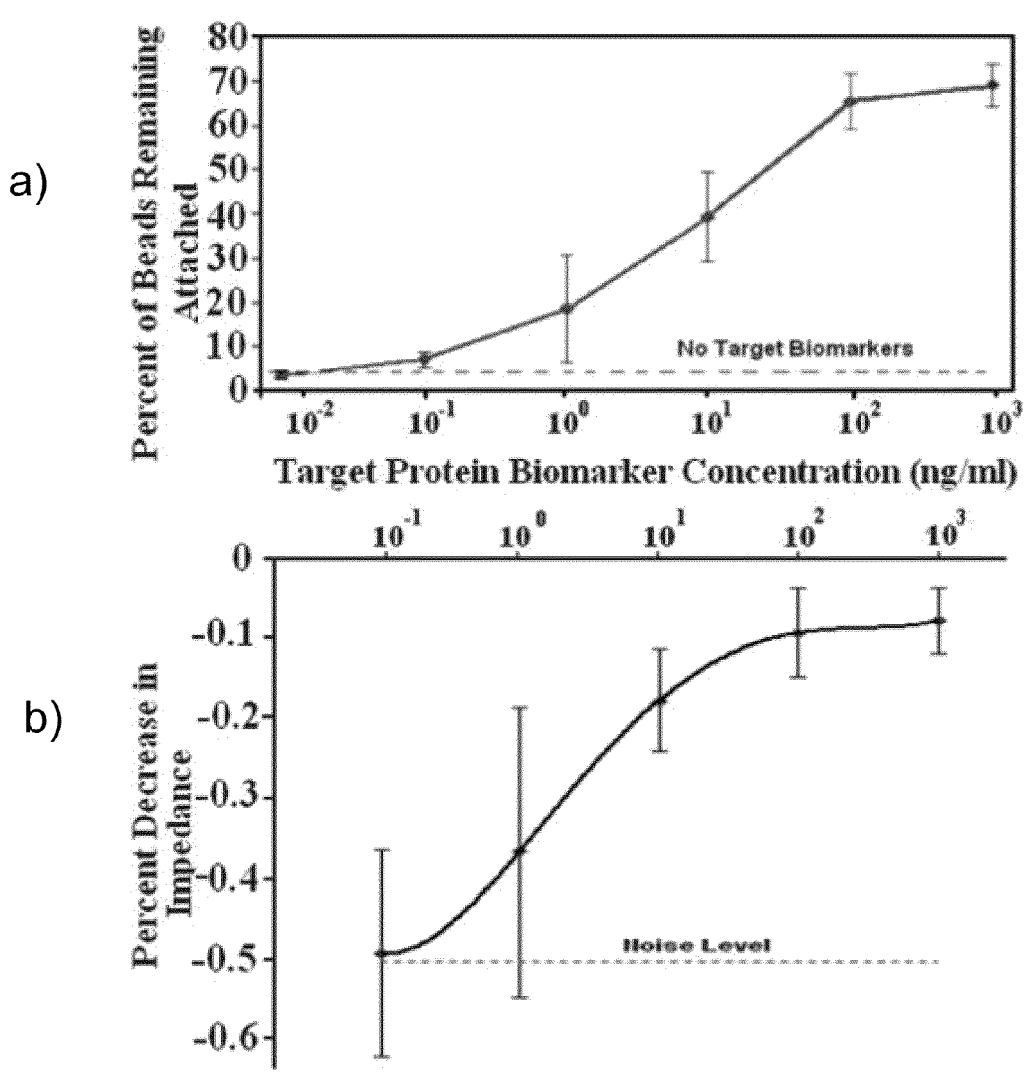
FIG. 11. (a) Percentage of beads remaining as a function of target protein biomarker concentration. (b). Percentage decrease in impedance as a function of target protein biomarker concentration.

Referring to FIG. 11, (a) shows the percentage of beads remaining attached in the micro-channel after incubation, with different concentrations of target protein biomarker as measured optically, establishing a dynamic range of 3 orders of magnitude. A detection limit of 1 ng ml-1 has been demonstrated. (b) show the percentage decrease in ionic impedance across the channel as a function of protein biomarker concentration with standard error bars. Detection limit of 1 ng ml-1 and dynamic range of three orders of magnitude has been demonstrated.

The standard error bars for the electrical measurements are greater than the standard error bars for the optical measurements. The impedance sensitivity to the location of the beads between the electrodes is the main cause for this inconsistency. The current method used for solving this problem is to run the experiment at least five times and to plot the average value as shown in FIG. 11b. This results in a higher resolution of biomarker concentration, making quantification using this technique practical. There are several other methods for reducing the standard error bar for the electrical quantification measurements. One possibility is to integrate interdigitated electrodes at the base of the channel across the whole channel, effectively increasing the active area of the sensor. Another possibility is to integrate multiple sets of electrodes across the whole channel, which will not only effectively increase the active area of the sensor, it will also have a higher electrical sensitivity than a channel with interdigitated electrodes.

Although we performed the capture of the target protein biomarker off-chip, it is also possible to perform this step on-chip to inject the test sample in the microfluidic channel so that the target proteins get captured by the primary receptors immobilized on the surface of the channel. Doing so would simplify the process for preparing reagents and remove the need for the centrifuging step required in order to remove the free target proteins from the solution.

One of the main advantages of our techniques is that it is able to operate at salt concentrations as high as 138 mM NaCl or even 800 mM NaCl, as opposed to other techniques such as the use of bionanoFETs where they are limited to salt concentrations as low as 2 µM, which makes them unable to operate in physiologically relevant samples. This opens the door to the possibility of direct detection of biomarkers in clinical samples such as blood or serum.

We describe here a method for electrically detecting target protein biomarkers without the need for labeling and bulky readout instruments. We have achieved a detection limit comparable to sandwich ELISA, which tends to achieve detection limits above 10 pM. Electrical detection is much more inexpensive and can be easily multiplexed and integrated into a portable device useful for analyzing a wide panel of markers. Electrical detection also eliminates the need for fluorescent labeling which lowers the costs of the reagents.

While we demonstrated the detection of anti-hCG, we emphasize that this assay is applicable to all protein biomarkers. Our technique has the advantage of real-time, electrical detection and quantification of target biomarkers. By fabricating multiple channels onto a single chip and immobilizing different antibodies in each of the channels, this technique can be used for multiplex sensitive high throughput analysis for probing a complex mixture, which is of utmost necessity for point-of-care and early stage diagnosis.

Conclusions

Our technique addresses the clinical need for developing an inexpensive platform for analyzing a wide panel of biomarkers necessary for early disease diagnosis. We present herein a device using a functionalized microchannel with integrated electrodes which can be used for multianalyte detection and quantification. We have demonstrated the detection of a target biomarker with a detection limit of 1 ng ml-1 and a dynamic range of three orders of magnitude, and the ability to operate at high salt concentrations. We have described the design, fabrication, and the electronic apparatus employed for testing our sensors in detail. Given that our technology has the ability to be multiplexed, we envision and recognize that this technique opens many new doors in the development of high throughput devices used in the clinical setting.

DNA-DNA Hybridizations[2]

[2] To repeat, we have already developed a microfluidic device capable of electrical detection of DNA-DNA hybridizations. Javanmard, M. et al. 2009 Sensors Journal, IEEE 9 (8): 883-891. We have advanced this current technology and improved upon its sensitivity by decoupling the capture chamber from the electrical sensor. Adaptation is empirical and well within the level of skill in the art given the present disclosure.

Disease diagnosis at an early stage requires the availability of inexpensive platforms which can accurately and rapidly analyze a wide panel of biomarkers, genomic biomarkers in particular. Genetic biomarkers are typically detected through recognition of DNA hybridization events, which is typically performed using DNA microarrays, requiring overnight incubation times, and bulky and costly optical equipment. Here, we present the use of bioactivated microfluidic channels for the real time detection of DNA hybridization electrically. Our technique is several orders of magnitude faster in time compared to the use of microarrays, and two orders of magnitude lower in cost.

Introduction

In the microchannel gating technique for DNA biomarker detection, DNA probe molecules are immobilized on the surface of the microchannel. Target DNA molecules are immobilized on the surface of micron sized beads. The beads are then injected into the microchannel (FIG. 12A) partially clogging the channel resulting in an instantaneous increase in the baseline resistance (FIG. 12C). The requirement for successful detection of the DNA hybridization (FIG. 12B) is that the surfaces of the microspheres contain target DNAs which are specific and complementary to the probe DNAs immobilized on the active area of the sensor.

Figure 12:
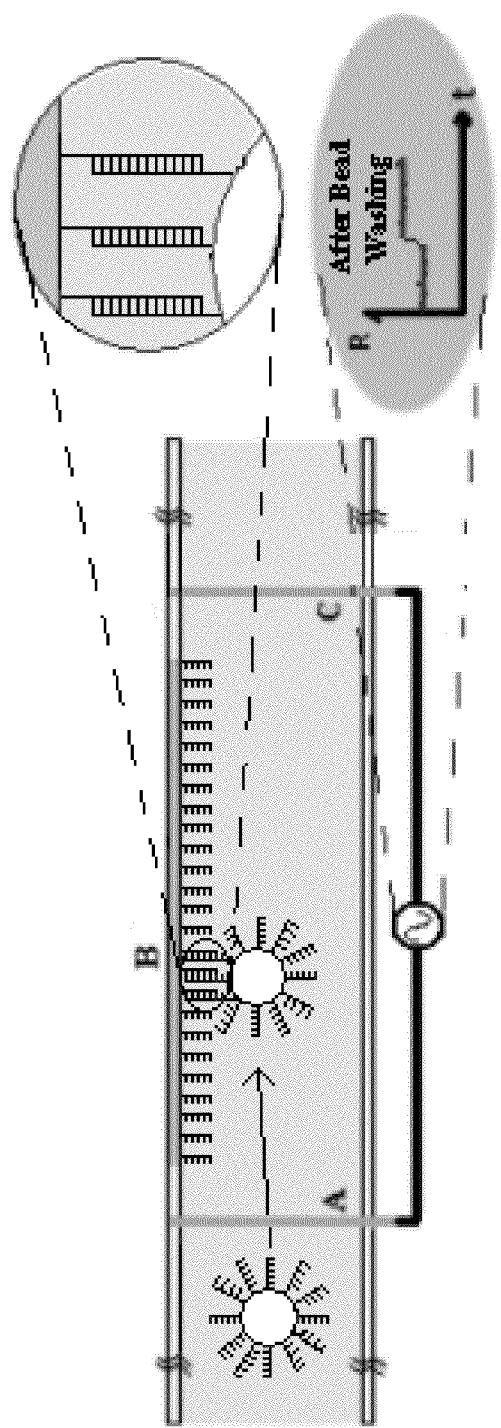
FIG. 12. (A) Microchannel surface activated with oligonucleotide probes. (B) Hybridization. (C) Increase in channel resistance.

Referring to FIG. 12, to recap, A) shows the surface of the microchannel is activated with oligonucleotide probes. Target DNA strands are immobilized on the surface of polystyrene beads, which are injected into the micro-channel. B) shows hybridization of the DNA strands causes capture of beads resulting in C) an increase in the channel resistance. In order to be able to detect the hybridization resulting in the capture of a single bead, it is also necessary that the microspheres used be comparable in size to that of the channel geometry.

Experimental Procedures

The microsensor consists of gold electrodes on a glass substrate covered with a PDMS slab embedded with a microfluidic channel. Electrodes were patterned using evaporation and then lift-off.

The target DNA sequence of 5'-CCCCCCCCCC TTTTTTTTTTTTTTTTTTTTTTTTTTTTTTTTTTTTTTTT TTTTTTTTTTTTT (SEQ ID NO:2), 62 base pairs long, was biotinylated at the 5' end. 1 µl of biotinylated target DNA (150 µM) was poured into 50 µl solution (PBS buffer) containing 0.5% (m/v) 20 µm polystyrene beads precoated with streptavidin (Spherotech Inc., Lake Forest, Ill.). The solution was rotated for 15 minutes in order to prevent precipitant from forming. The solution was then centrifuged, the supernatant removed, and the beads were again resuspended in PBS. The PBS buffer had a salt concentration of 700 mM NaCl which is required for rapid hybridization of DNA strands. This process was repeated three times in order to ensure that all free target DNA strands were removed from the solution. The same procedure was also used to coat 20 µm polystyrene beads precoated with streptavidin (Spherotech Inc., Lake Forest, Ill.) with DNA. The probe DNA sequence of 5'-CCCCCCCCCCAAAAAAAAAAAAAAAAAAAAAAAAA AAAAAAAAAAAAAAAAAAAAAAAAAAAAA (SEQ ID NO:3), 62 base pairs long, was biotinylated at the 5' end. Biotinylated Bovine Serum Albumin was immobilized on the bottom of the surface channel by physical adsorption. Afterwards, Streptavidin was incubated in the channel for 15 minutes in order to bind onto the biotinylated BSA. The biotinylated probe DNA was then incubated in the channel to be captured by the streptavidin molecules. Incubation times of at least 15 minutes were necessary to produce optimal immobilization results.

DNA Assay

The beads coated with target DNA were injected into the bioactivated microchannel at a flow rate of less than 200 nl/min. Complementary target DNA strands were observed to be captured instantaneously, while beads with non complementary DNA were not captured on the channel surface. It is interesting that the hybridization of the two DNA strands occurred within seconds, compared to DNA microarrays which require incubation times as long as 24 hours. This will be discussed further below.

Figure 13:
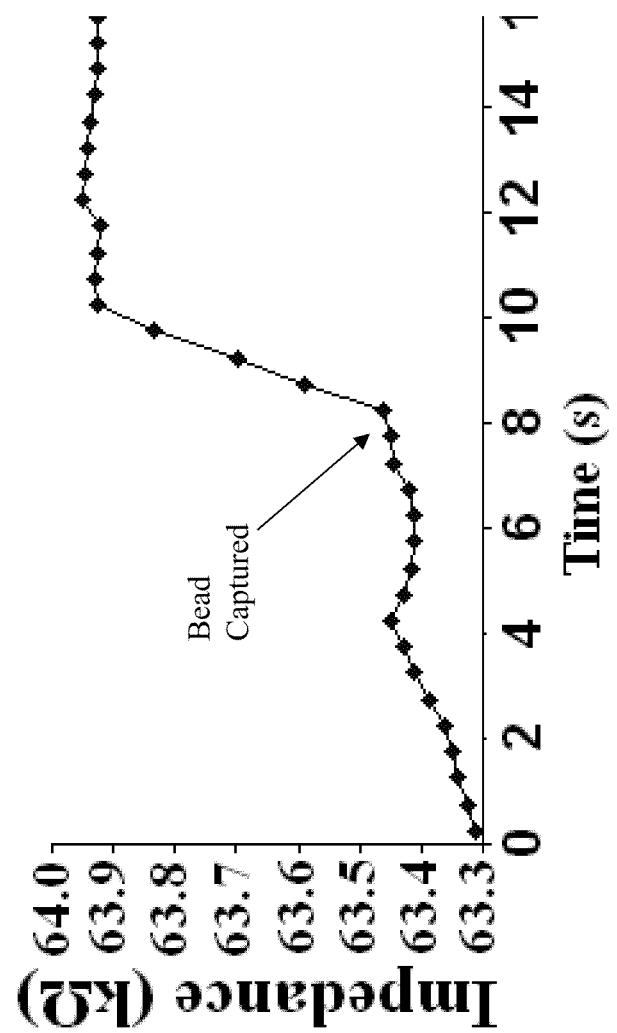
FIG. 13. Impedance as a function of time.
Figure 14:
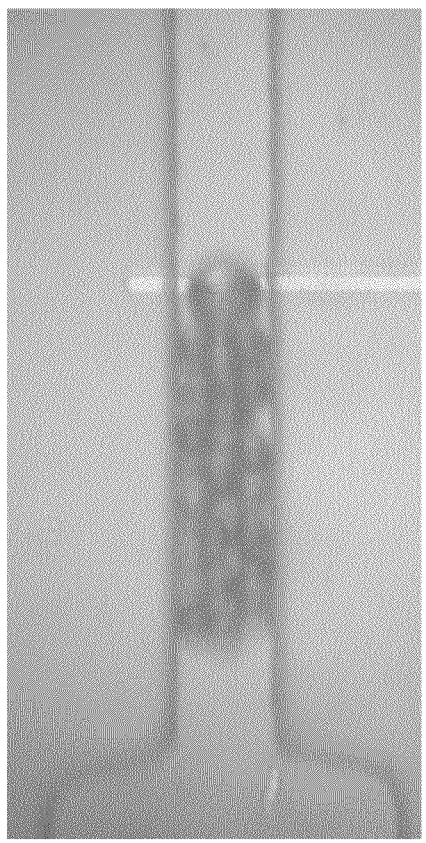
FIG. 14. Optical image of beads in channel.

In FIG. 13, we show representative data of a case where a large bead is captured. This results in an instantaneous increase in the channel resistance. Referring to FIG. 13, the resistance is measured across electrodes A and C. The resistance increases at t=9 s as the beads passing through the channel are trapped onto electrode C, as shown in FIG. 14. Referring to FIG. 14, it shows an optical image of beads in the channel as a large bead is captured on electrode C at t=9 s. After the large bead is captured several beads pile up in the channel behind it. This particular case was not due necessarily to DNA hybridization; however we included this to show the ability of our system to detect impedance changes as a result of beads being captured in the active region of the sensor. After the first bead is captured onto electrode C, several beads pile up in the channel behind it.

Minimizing False Positive Signals

It is important to minimize the false positive signals which arise from beads nonspecifically binding to the surface of the channel. This result can be due to electrostatic interactions between the beads and the channel surface, the nonspecific interactions between the DNA and the surface, beads coming to rest on the surface, and many other causes. In general bead capture due to DNA strands hybridizing is higher in affinity compared to nonspecifically bound beads. By adjusting the flow rate such that the drag force on the beads is strong enough such that nonspecifically bound beads can be pulled off while the beads bound due to DNA hybridization remain attached, it is possible to minimize the nonspecific interactions.

In this assay the target DNA consisted of the following sequence, Biotin-5'-AGGTGTGGGGTGATCATTTGT-CAGTGTGAGGGAGTGTGGTAGTGC-3' (SEQ ID NO:4), and the probe DNA consisted of Biotin-5'-ACACCTGCAC-TACCACACTCCCTCACACTGACAAATGATCACCCC-3' (SEQ ID NO:5). We also examined a target DNA strand with a single base pair mismatch in the 27$^{th}$ position of the sequence. In this assay we used 10 μm beads.

Figure 15:
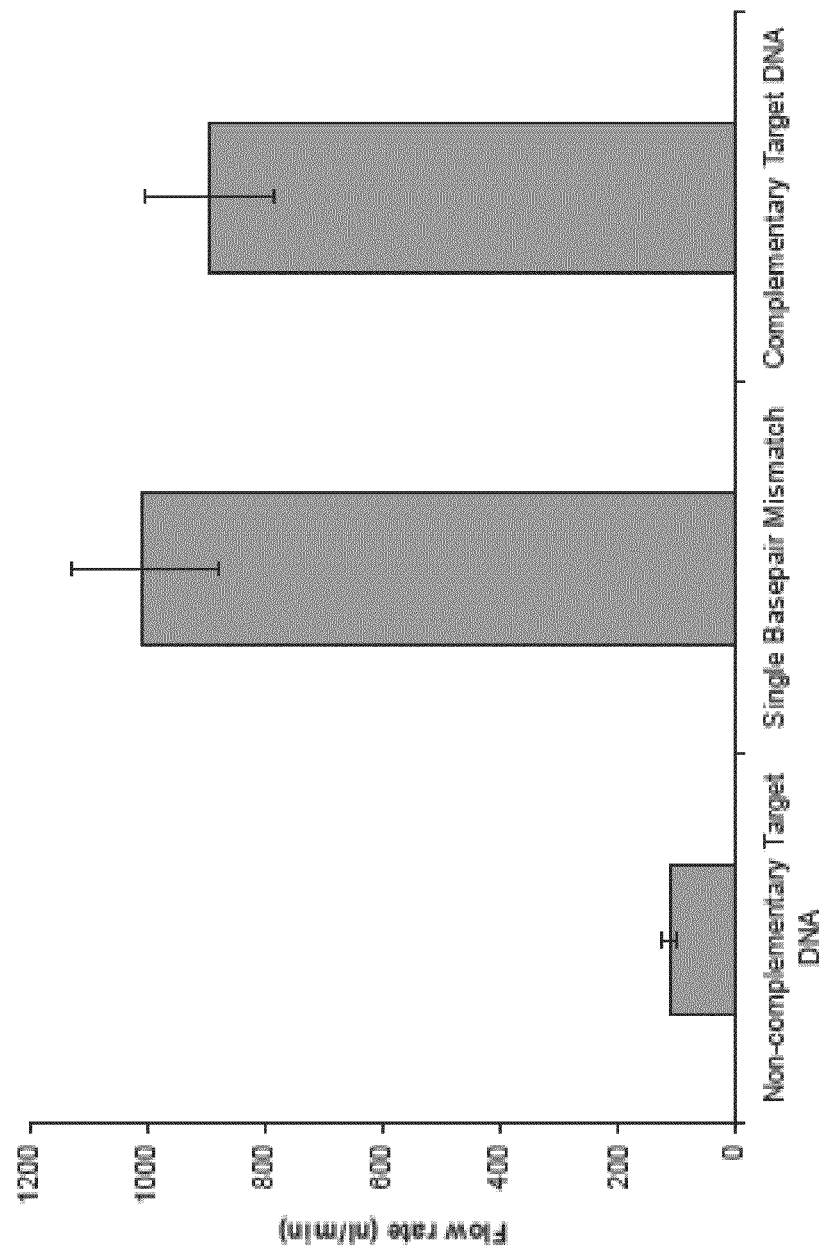
FIG. 15. Flow rate as a function of complementarity of target DNA.

The beads for each assay were separately incubated in the channel for one minute. The flow rate was incrementally increased as the beads were pulled off. The average flow rates and the standard error required to detach the beads from the surface of the channel are shown in FIG. 15. In the first column the target DNA on the beads and the probe DNA on the channel surface were non-complementary with each other, and were not expected to hybridize. A flow rate of 100 nl/min was required to wash off the beads. In the second column, the target DNA and the probe DNA were mismatched by a single base pair, requiring a high flow rate of 1000 nl/min to wash off the beads. In the third column the target DNA and the probe DNA were complementary to each other also requiring a high flow rate of 900 nl/min to wash off the beads. In the second case, the single base pair mismatched DNA unexpectedly has a higher affinity compared to the perfectly matched DNA, however their error bars overlap with each other. With more experiments, it is expected that these two average flow rates will converge. With lengths of DNA as long as those we have examined in this study, we are unable to distinguish between single base pair mismatches and perfectly complementary DNA. This may however be more feasible with shorter length DNA molecules.

Referring to FIG. 15, it shows the average flow rate required to pull off all of the beads attached to the base of the channel, and also the standard error bars. In the first column, the target DNA and the probe DNA were completely mismatched, thus a negligible flow rate of 100 nl/min was sufficient to pull off the beads. In the second column, the DNA on the beads was mismatched with the probe DNA on the channel surface by a single base pair, and a flow rate of 1000 nl/min was necessary to pull off the beads. In the third column, where the target and probe DNA were expected to hybridize a flow rate greater than 900 nl/min was required to pull the beads off. In order to minimize the false positive signals due to beads non-specifically binding, one could operate within the flow rate window between 100 nl/min to 900 nl/min.

DNA microarrays typically require overnight incubation before the hybridization can be detected. Using our biochip we are able to achieve detection of hybridization within seconds. The reason for this great decrease in analysis time is a result of the number of molecules required to hybridize before being detectable by the sensing apparatus. For DNA microarray technologies, at least several thousand molecules are required to hybridize before producing enough optical signal to be detected by the fluorescent scanners. In the case of our assay, this number can be determined by calculating the affinity of the beads to the surface of the microchannel, and then determining the number of hybridized DNA molecules by dividing the total force by the force holding a single molecule together.

Calculation of the Affinity of the Beads and the Channel Surface

The flow rate in the channel is directly proportional to the drag force applied to the beads. The drag force required to detach the beads from the surface of the channel is equal to the binding force between the hybridized DNA molecules. In order to determine the binding force between the hybridized DNA molecules accurately using the flow rates in FIG. 15, it would be necessary to perform a rigorous calculation of the relationship between the flow rate and the drag force on a sphere on the bottom of a microchannel with the dimensions of our fabricated channels. However, in order to get a quick order of magnitude estimate of the drag force, it is possible to use the sphere-drag formula of Stokes:

$$F=6\pi\mu Ua \quad (1)$$

where U is the mean velocity at which the sphere travels, and a is the radius of the sphere.

An average flow rate of roughly 900 nl/min was required to pull the beads off the surface of the channel which corresponds to a drag force of 126 pN. The rupture forces for larger molecules of DNA tends to saturate at around 70 pN. This means that on average the beads are held attached to the base of the channel by the force of one or two DNA molecules.

This confirms our initial hypothesis regarding the reason for the rapid hybridization detection rates. This is due to the fact that a single DNA molecule hybridizing is sufficient to cause the bead to get captured, compared to DNA microarrays which require several thousand DNA molecules to hybridize in order to generate enough optical signal to be detectable by the fluorescent scanners.

Conclusion

We have demonstrated herein the ability of our biochip to detect the hybridization of complementary DNA molecules within seconds. Our system is advantageous over conventional DNA microarray technology because the readout time is reduced by four orders of magnitude without the need for any fluorescent labels. The costs required for labeling on an affymetrix chip average at roughly $250, whereas the use of polystyrene microspheres for labeling averages at about $3 per chip, a decrease of two orders of magnitude. A sample volume of roughly 0.1 μl is required to perform this assay. The ability to detect DNA hybridization on chip electrically opens up the potential for multiplexed detection of nucleic acid biomarkers on a portable device which can be a good candidate for use in the clinical setting.

Target Cells[3]

[3] To repeat, we have already developed a microfluidic device capable of electrical detection of target cells. Javanmard, M. et al. 2007 *Biomicrofluidics* 1 (4): 044103-044101. We have advanced this current technology and improved upon its sensitivity by decoupling the capture chamber from the electrical sensor. Adaptation is empirical and well within the level of skill in the art given the present disclosure.

Currently, microbiological techniques such as culture enrichment and various plating techniques are used for detection of pathogens. These expensive and time consuming methods can take several days. Described herein is the design, fabrication, and testing of a rapid and inexpensive sensor, involving the use of microelectrodes in a microchannel, which can be used to detect single bacterial cells electrically (label-free format) in real time. As a proof of principle, we have successfully demonstrated real-time detection of target yeast cells using Concanavalin A (Con A), a glycoprotein with affinity for the sugar molecules on yeast surface, in place of antibodies, by measuring instantaneous changes in ionic impedance. We have also demonstrated the selectivity of our sensors in responding to target cells while remaining irresponsive to nontarget cells. Using this technique, it can be possible to multiplex an array of these sensors onto a chip and probe a complex mixture for various types of bacterial cells.

Device Operation and Theory

The basic device (FIG. 16) contains three electrodes. The channel current is monitored between electrodes A and C. The volume between electrodes A and C is the active area of the sensor. A third gold electrode, B, is included in the active area of the channel, allowing for immobilization of antibodies with an affinity to bind to target bacterial cells in the active area of the sensor. Gold electrodes are very suitable for surface chemistry modifications, such as deposition of surface assembled monolayers, which will optimize the immobilization of the antibodies. A sample suspected of containing the target bacterial cells is injected into the microchannel. If the sample contains the targeted bacteria, they will attach to the electrodes, partially clogging the channel thus resulting in solution resistance increase. By monitoring the impedance across microelectrodes A and C, it is possible to detect the channel gating caused by bacteria attached inside the channel. By choosing channel and electrode geometries close to the bacteria size, the probability of bacterial cells being captured by the electrodes and also the impedance changes are maximized.

Figure 16:
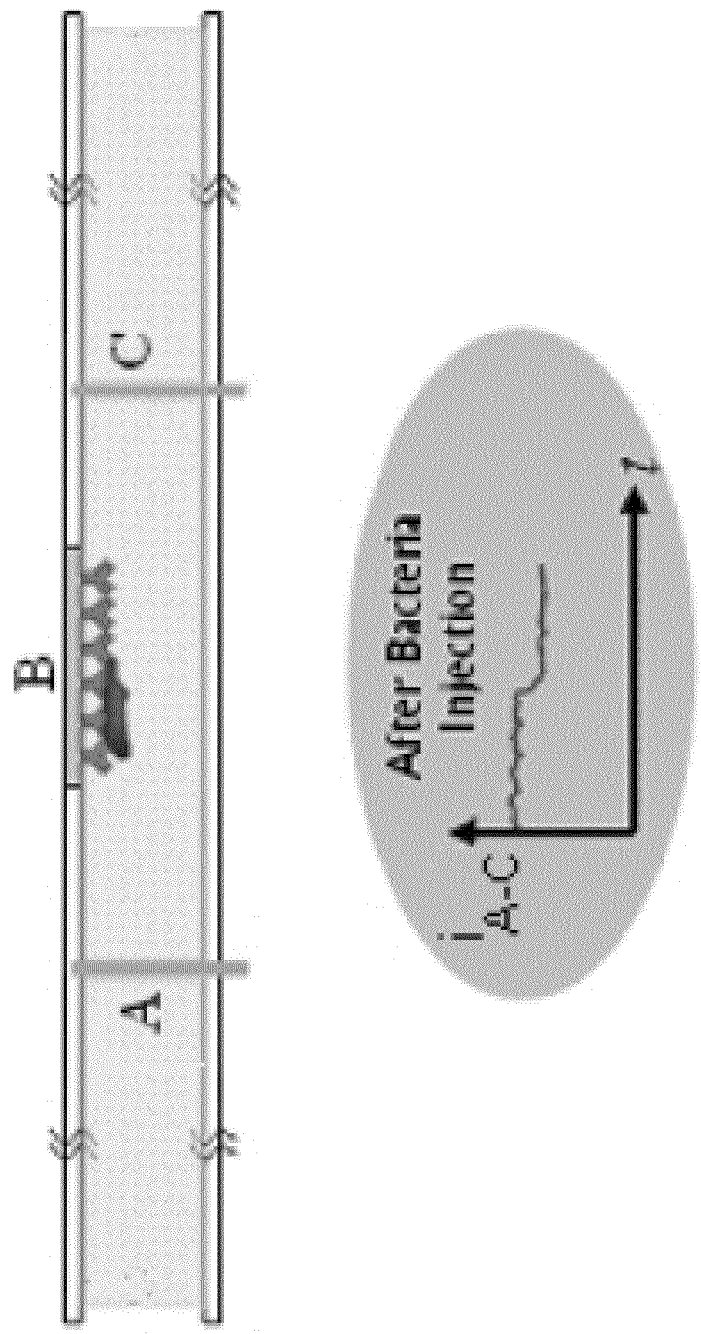
FIG. 16. Schematic of microfluidic sensor for target cells.

Referring to FIG. 16, to recap, the figure shows a cross section schematic of a gated microchannel with electrodes labeled A, B, and C. The targeted bacteria bind to the antibodies which are immobilized on the gold electrode. The bottom plot predicts the current between electrodes A and C after injection of bacteria.

For selective detection to be achieved, this technique would require that the channel geometry closely correspond to that of the target cell and that the target cell contain surface markers specific for the monoclonal antibodies immobilized in the active area of the sensor. Thus, we emphasize that the successful detection of target yeast cells demonstrated in this study can be extended for detection of all types of cells including pathogenic bacteria or even cancer cells in blood. However, the channel geometry must be tailored to the type of cell which is being targeted.

Device Design

The microfluidic biochip used in this study is shown in FIG. 17A. Multiple channels were fabricated onto a single chip as shown in FIG. 17B. Experiments were conducted on two sets of channel sizes, one 50 μm deep and 50 μm wide (FIG. 17C), and the other 20 μm wide and 10 μm deep (FIG. 17D).

Figure 17:
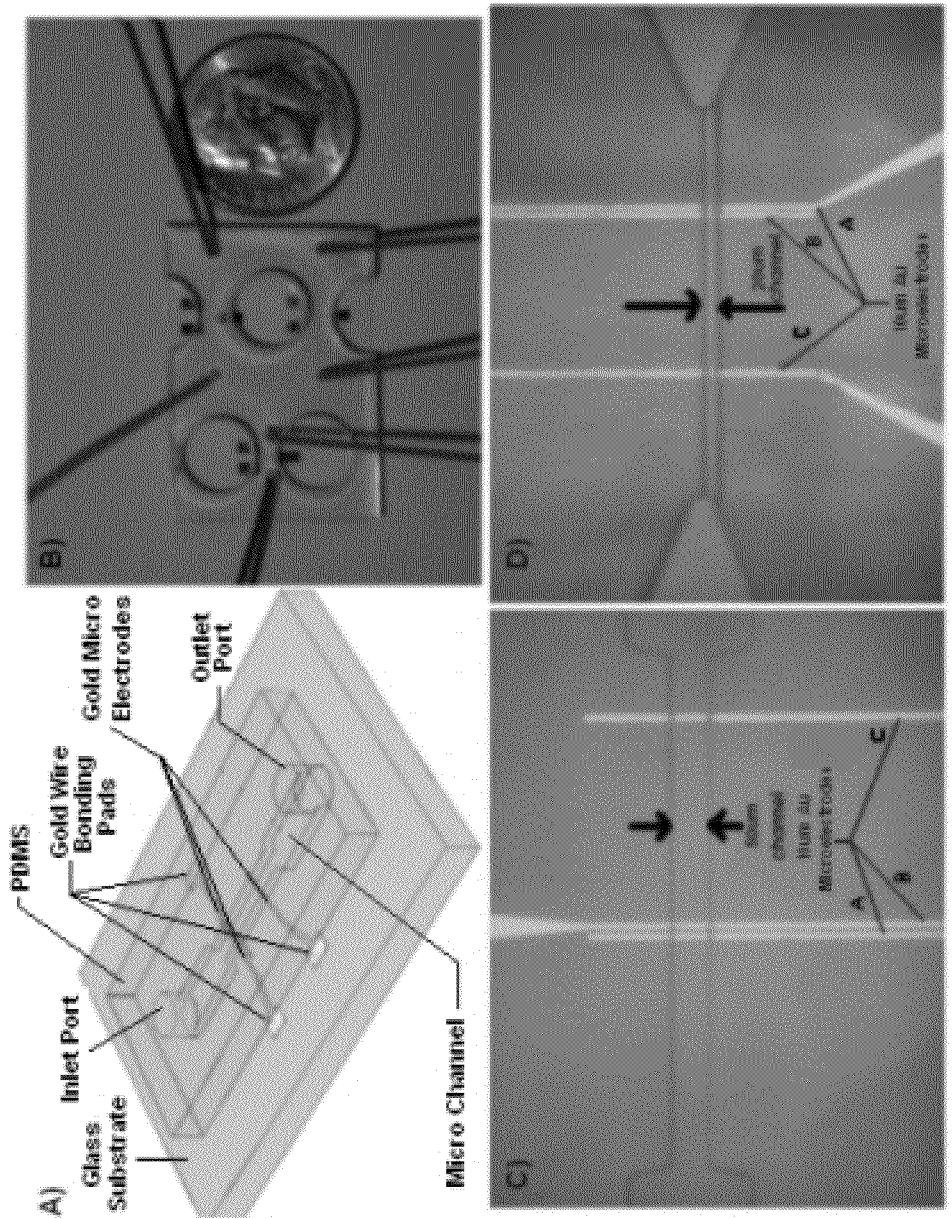
FIG. 17. (A) Schematic of a single chip. (B) Photograph of a single chip. (C) Optical micrograph of channel of one size. (D) Optical micrograph of channel of different size.

Referring to FIG. 17, more particularly, (A) shows a schematic of a microfluidic chip used in this study. (B) shows a photograph of a single chip containing three different channels with integrated electrodes. (C) shows an optical micrograph of the top view of a 50 μm deep channel device integrated with electrodes labeled A, B, and C. Electrode B was not used in this study. (D) shows an optical micrograph of the top view of a 10 μm deep channel.

Electrode Fabrication

Au/Cr electrodes (2000 Å/150 Å) were fabricated on a glass wafer using traditional photolithography, sputtering, and then lift-off processing. The glass wafer was then diced into individual chips, in order to prepare them for bonding to the PDMS cover.

Channel Fabrication in PDMS

The PDMS cover was made by patterning SU-8 25 photoresist on a silicon wafer. PDMS (10:1 prepolymer:curing agent) was poured into a petri dish with the master mold at the bottom, and then cured. Microbore tubes were inserted to make holes for the inlet and outlet ports of the channels. Individual sets of microchannels were cut and removed for sealing onto the patterned glass chips.

PDMS Glass Bonding

The glass chips and the PDMS slabs embedded with microchannels were both treated with oxygen plasma. The PDMS slab and the glass chips were then aligned under a microscope so that the electrodes overlap properly with the channel, and subsequently bonded together to make a very tight seal.

Measurement Apparatus

Figure 18:
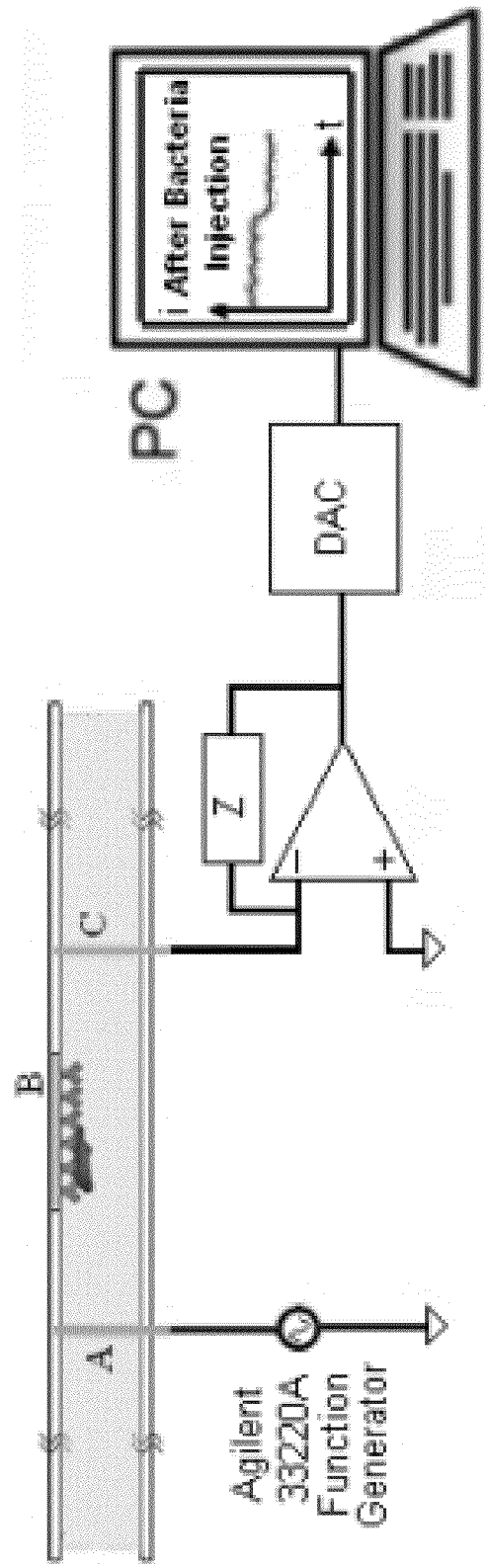
FIG. 18. Schematic of experimental setup.

Electrical impedance measurements were collected across electrodes A and C both as a function of frequency and time (FIG. 18). FIG. 18 shows a schematic of the experimental setup including amplification circuitry and data acquisition. A voltage signal was applied to electrode A using an Agilent 33320A function generator. The current passing across electrodes A and C was converted to a voltage and amplified with an EI-400 Potentiostat (Ensman Instruments, Bloomington, Ind.), and then sampled with a National Instruments PCI4452 data acquisition card. The data were read and analyzed by a Labview program. In order to confirm the validity of our real-time electrical measurements, we simultaneously monitored our channels using optical microscopy.

Experimental Procedure

In this study, yeast cells were used as target cells, and Concanavalin A (Con A), a glycoprotein with affinity for the sugar molecules on yeast was used in place of antibodies in order to demonstrate the success of the technology in selectively detecting target cells.

Preparation of Yeast and Con A

Yeast (*S. cerevisiae*) cells were maintained on YPD (Yeast Extract/Peptone/Dextrose) agar plates at 4° C. An isolated colony was used to inoculate 5 ml of YPD broth, and the culture was grown to saturation for 16 h at 30° C. Cells were then collected by centrifugation and resuspended in a solution containing 200 mM KCl and 10 mM HEPES in addition to 1 mM MgCl2, 1 mM MnCl2, and 1 mM CaCl2 which are necessary for Con A activity. The cell concentration in the final solution was diluted to $10^7$ cells/ml.

The Con A, from Calbiochem (San Diego, Calif.), was diluted to 10 mg/ml Immobilization of Con A on the electrodes was carried out by physical adsorption. Con A solution was injected and incubated into the channel for 15 mM, then activated by the injection of Mn2+, Mg2+, and Ca2+ ions. A 200 mM KCl solution in 10 mM Hepes buffer with a pH of 6.8 containing yeast was injected into the channel at a flow rate of 100 nl/min.

Results and Discussion
Impedance Spectrum

The impedance behavior across the channel is dictated by the processes occurring at the electrode-electrolyte interface and also the physical properties of the electrolyte, which can be represented with an electrical equivalent circuit consisting of a network of resistances and capacitances. Of particular importance are the bulk solution resistance and also the double layer capacitance, the latter of which results from hydrolyzed ions accumulating at the surface of the electrodes. Reactions occurring at the interface such as electron-transfer and ion diffusion from the bulk electrolyte to the electrode surface (Warburg impedance) may also affect the impedance at lower frequencies. However, such effects become negligible at higher frequencies. Due to the small separation of the layer of accumulated ions with the electrode surface, the double layer capacitance becomes very large to the extent that it dominates the impedance at low frequencies, which explains the drop in impedance as frequency increases. At higher frequencies, as the impedance resulting from the combined effects of the double layer capacitance, the electron transfer resistance, and also the Warburg impedance diminishes, the solution resistance dominates the impedance, which consequently becomes flat with frequency.

Figure 19:
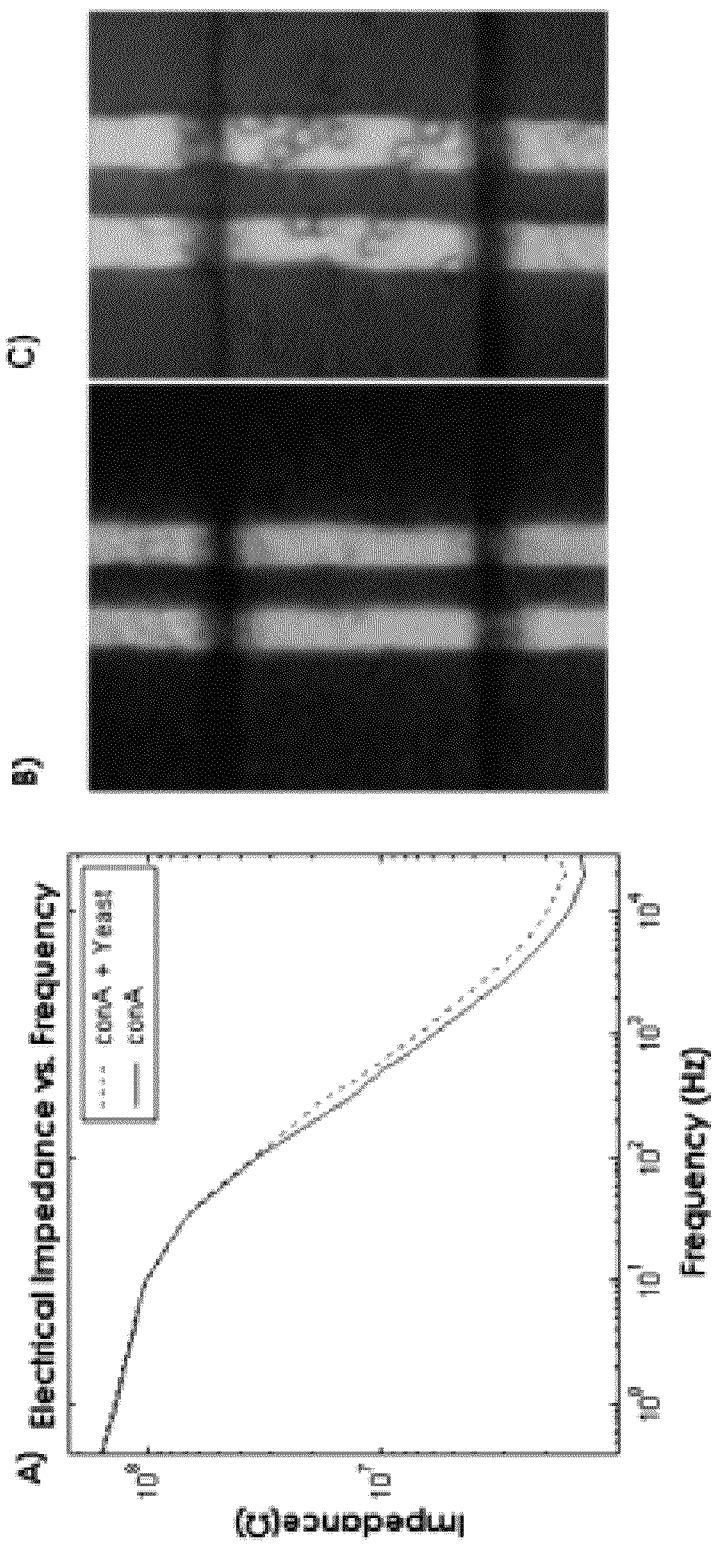
FIG. 19. (A) Impedance as a function of frequency. (B) Optical micrograph of electrodes before yeast binding. (C) Optical micrograph of electrodes after yeast binding.

It was necessary to measure the impedance spectrum across the channel in order to gain a proper understanding of the impedance behavior as a function of frequency as shown in FIG. 19A. As seen in FIG. 19A, the impedance levels off above 10 kHz indicating the solution resistance is dominant at these frequencies. The binding of yeast to Con A on the electrode results in an increase in ionic impedance at frequencies above 10 kHz indicating that impedance changes can be achieved resulting from ionic solution resistance increase. FIG. 19B is an optical micrograph showing the channels before the binding of yeast, and FIG. 19C is an optical micrograph showing the channel after the yeast cells have been attached inside the channel. As seen in FIG. 19C, yeast cells bind on both the gold electrodes and the glass base of the channel. However, no yeast cells were observed to bind to the PDMS top layer. This demonstrates that the above mentioned method of Con A immobilization results in the Con A adsorbing onto both the gold electrodes and on the glass base of the channel. This would limit the sensitivity of the device since some targeted cells would bind to the channel wall outside the active area of the sensor. One may address this problem by construction of self-assembled monolayer on gold. Fabrication of a layer of protein G on this surface and attachment of the antibody onto the protein G layer could be carried out, essentially as described by Oh, B. K. et al. 2004 *Biosens. Bioelectron* 19: 1497.

Of particular interest is to find the frequency at which the ionic resistance in the channel begins to dominate the impedance. It may be feasible to detect the binding of a targeted cell based on a change in capacitance, which can be done by measuring impedance at low frequencies where the electrical impedance is dominated by the double layer capacitance of the electrodes. However, we had difficulties achieving this due to a drift in impedance which occurred during our experiments at low frequencies, which made it difficult to get consistent results. It is likely that this impedance drift is due to an accumulation of ions at the surface of the electrode at low frequencies resulting from dc input bias offset currents of the circuitry connected to the electrodes, an effect which seems to have been frequently observed in the literature. As seen in the impedance spectrum, the binding of yeast cells on the channel walls in the region between electrodes A and C results in an increase in impedance at frequencies above 100 Hz. Based on the impedance curve, it can be seen that the solution resistance begins to dominate the impedance at frequencies above 10 kHz. The binding of yeast to Con A on the electrode results in an increase in ionic impedance at frequencies above 10 kHz indicating that impedance changes can be achieved resulting from ionic solution resistance increase.

Binding Specificity

Figure 20:
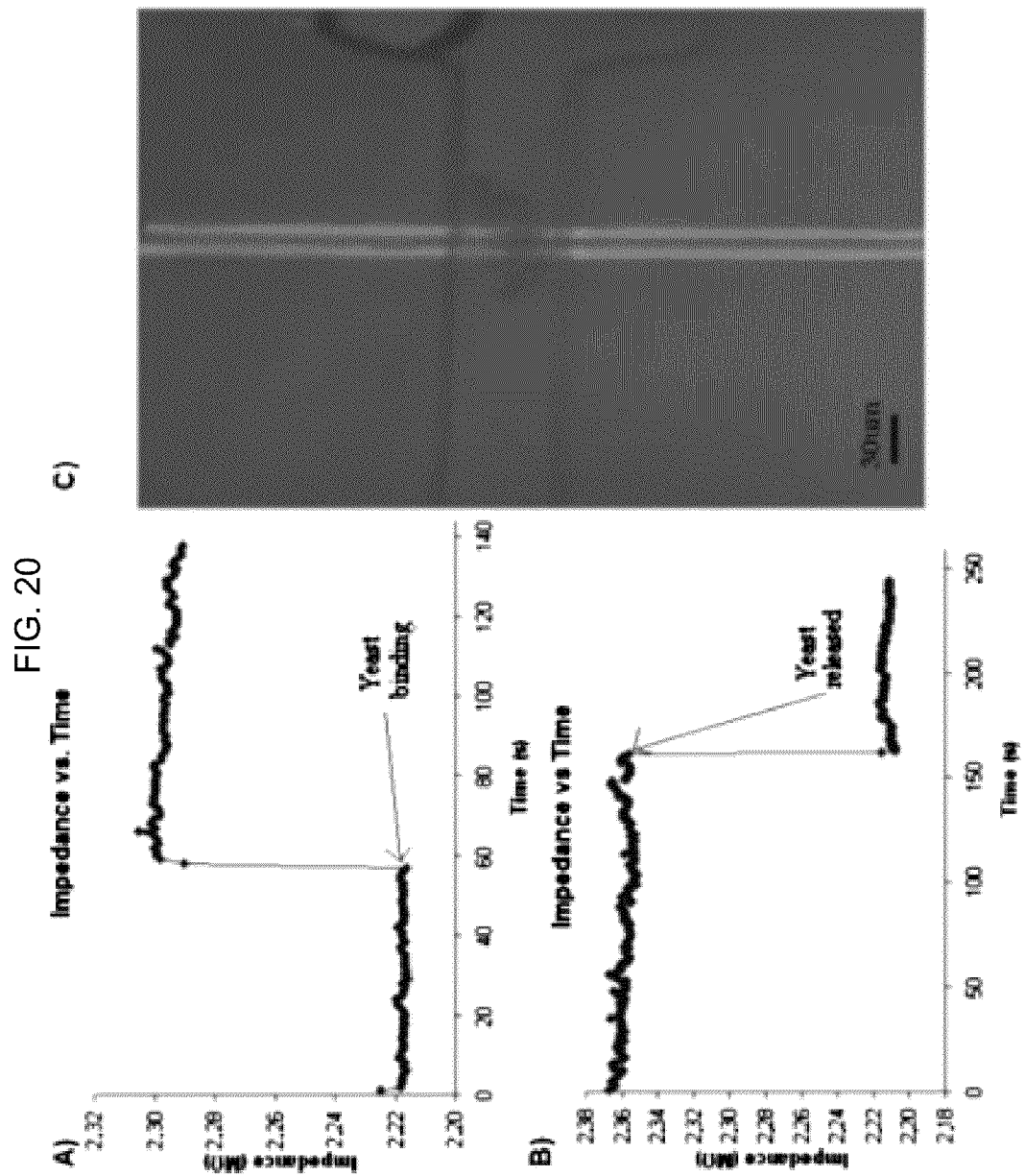
FIG. 20. (A) Impedance as a function of time, yeast binding. (B) Impedance as a function of time, yeast released. (C) Optical micrograph of electrodes after yeast binding.

In order to achieve real-time detection, the electrical impedance was measured over time between electrodes A and C at a frequency of 29.8 kHz in the 50 μm deep channel. This frequency turned out to be optimum for our system, since the ionic impedance is dominated by solution resistance. We refrained from working at frequencies higher than this, in order to avoid the effects of parasitic inductances. FIG. 20C is an optical micrograph showing a clump of approximately 30 yeast cells binding onto electrode A resulting in an instantaneous increase in impedance at time t=59 s as shown in FIG. 20A. In a separate experiment (FIG. 20B), impedance measurements were taken as a clump of yeast was already bound onto the electrodes. At time t=155 s, the yeast cells were removed by increasing the pressure slightly, which resulted in an instantaneous decrease in impedance. As seen in FIG. 20B, the noise level is 0.02 MΩ, which is 1% of the base value of 2.22 MΩ. A change of 0.8 MΩ resulted from the binding of a clump of approximately 30 cells. This means that with the current device geometry at least eight cells need to bind to the electrodes in order to cause a change greater than the noise level. In order to increase the electrical sensitivity to the single cell level, a potential optimization would consist of decreasing the cross sectional area of the microchannel by a factor of eight, a modification which can be easily carried out by skilled artisans.

Large Channel Experiments

Figure 21:
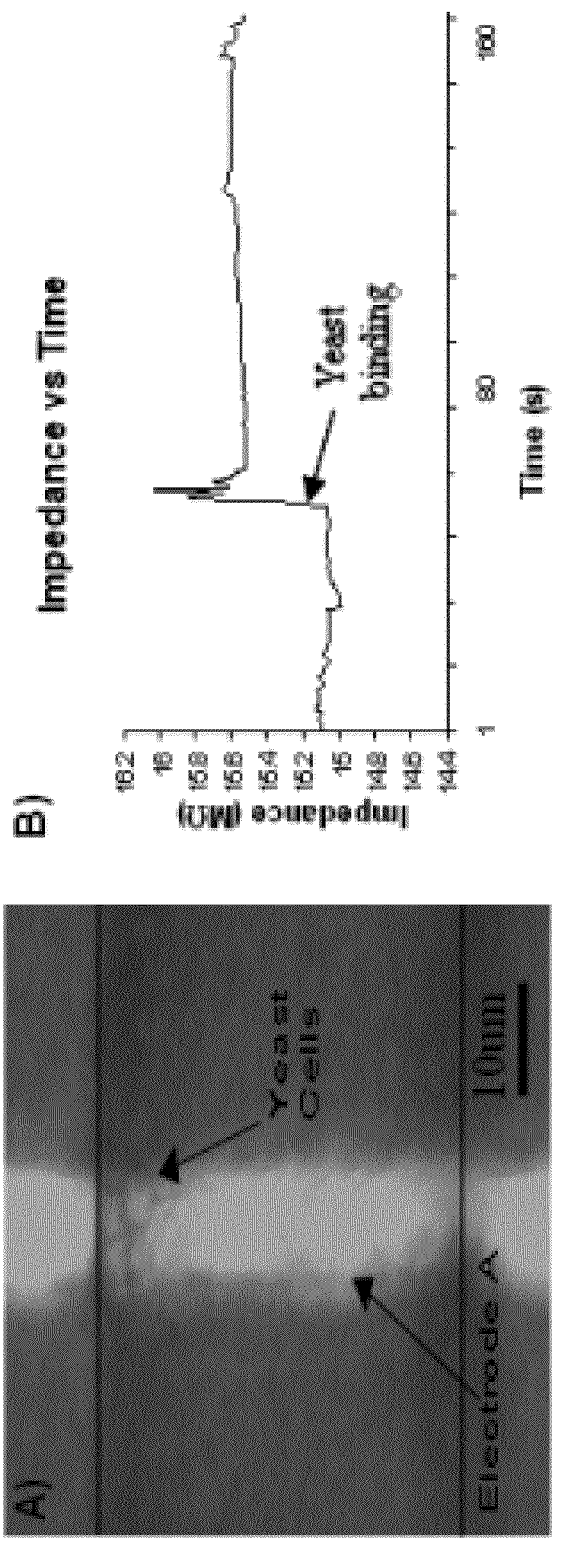
FIG. 21. (A) Optical micrograph in large channel experiments. (B) Impedance as a function of time.

FIG. 21A is an optical micrograph showing yeast cells being captured by the receptors on the electrode surface in the 50 μm deep channel. Results in FIG. 21B show an instantaneous increase in electrical impedance (at 29.8 kHz) as a small number of cells bind to the surface of the electrodes at t=55 s, demonstrating real-time detection of cell capture. A current change of 2.6% resulted from several cells binding onto the electrode. In order to verify that binding of the cells to the channel walls were as a result of specific antigen-antibody interactions, we performed two different control experiments for the 50 μm deep channels. A 200 mM KCl solution in 10 mM Hepes buffer with a pH of 6.8 containing yeast was injected at a flow rate of 100 nl/min into a channel in which Con A had not been immobilized on the surface. In order to further confirm the specificity, we ran a separate experiment where we treated the surface of yeast with alpha-mannosidase and alpha-glucosidase for removing the sugars, mannose and glucose which have an affinity for Con A. We immobilized the channel with Con A and injected 50 μl of yeast solution with a flow rate of 100 nl/min. In both experiments, no binding of yeast occurred anywhere in the channel as predicted and consequently no changes in current occurred either. This confirms that results in FIG. 21 are due to specific binding, and that such a device configuration can be used to detect the presence of a target cell in a complex mixture.

The ability to selectively detect target cells in a complex mixture requires that nonspecific binding of nontarget cells onto the electrodes and the glass base between the electrodes be minimized. Given that nonspecific interactions are weaker than specific binding events, we minimized the nonspecific interactions by using a flow rate high enough to unbind the nonspecifically bound cells. In our 50 μm wide by 50 μm deep channels, at very low flow rates (below 100 nl/min), we experienced many nontarget cells coming to rest on the electrodes and the glass base of the channel. At flow rates higher than 200 nl/min, we experienced target cells not having the opportunity to adsorb to the electrodes or the glass base of the channel, thus being undetectable using our technique. Thus, we used 100 nl/min since we found it to be the optimum flow rate for our system, both minimizing nonspecific binding events, while at the same time providing target cells with a sufficient opportunity to bind to the active area of the sensor.

A number of high-affinity monoclonal antibodies raised against bacterial surface antigens can also be used. The use of a mixture of such antibodies in the system would maximize specific interactions and further increase the strength of specific interactions relative to nonspecific binding. These attempts would further lower the possibilities for nonspecific adsorption.

Small Channel Experiments

Figure 22:
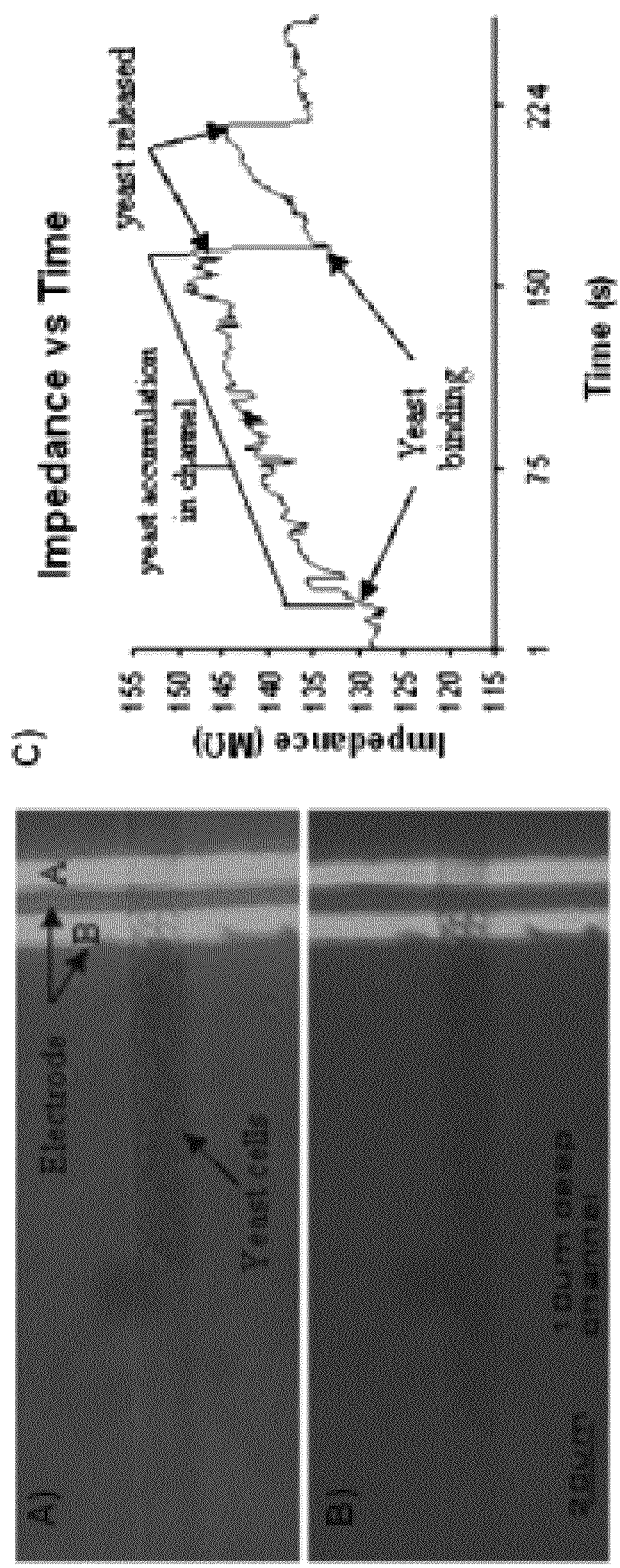
FIG. 22. (A) and (B) Optical micrographs in small channel experiments. (C) Impedance as a function of time.

In an attempt to further increase the electrical sensitivity of the sensor and also the probability of a cell being captured by the receptors in the active area, the 20 μm wide by 10 μm deep channels were tested. In this particular experiment, no receptors were immobilized onto the electrodes, so all capture was a result of nonspecific binding. FIGS. 22A and 22B are optical micrographs showing cells being captured on the electrodes and clogging the channel. As shown by the plot in FIG. 22C, at t=20 s as the first cells were captured by the electrode and the subsequent cells began accumulating in the channel, the impedance ramps up at a relatively steady rate. At t=160 s, the fluid pressure was momentarily slightly increased to unbind the cells from the electrodes and unclog the channel, resulting in an instantaneous drop in impedance. Immediately after the drop, cells began re-accumulating, which resulted in a steady increase in impedance until t=220 s when another momentary slight increase in fluid pressure was applied to release the cells. Beyond this time, no more cells were captured in the channel resulting in relatively constant impedance over time.

For channel sizes comparable to the diameter of yeast (5 μm), nonspecific binding and channel clogging have been shown to be problematic. A channel depth of 10 μm has shown to be too shallow for proper operation of the sensor. Larger channels have shown to be more practical, since we have proven them to be sensitive enough to electrically detect the presence of a small number of cells, while at the same time minimizing channel clogging and nonspecific binding. However, in order to obtain an electrical sensitivity approaching the single cell level, an intermediate channel depth could be used, which is well within the level of skill in the art.

Conclusions

We have demonstrated the proof of concept for a direct (label-free format) method for real-time detection of target cells. This method utilizes impedance measurements at 29.8 kHz to probe solution resistance changes associated with the blockage of ionic current due to cell binding on the channel walls in the active area of the sensor. While we focused on yeast cells in this study, the method can also be used for detection of pathogenic bacteria, cancer cells, or even testing water quality for possible contaminations, with appropriate optimization of channel geometries. In order to extend this method to practical applications like the detection of bacterial cells, and maintain the high electrical sensitivity of the device, it would be necessary to scale down the size of the channel geometries, thereby making it more compatible to the smaller dimensions of bacterial cells, in comparison to yeast cells. One particular advantage offered by this device is its selectivity in cell capture, which makes it possible to multiplex an array of these sensors onto a single chip and probe a solution to determine which types of bacterial cells it contains.

We demonstrated the feasibility of this technique for selective detection of target cells in a solution containing $10^7$ cells/ml. The sensitivity of this technique is limited by the probability of a target cell being captured in the active area of the sensor. The binding of target cells to the antibodies immobilized on the glass base in regions outside of the active area of the sensor also limits sensitivity. Detection limit can be enhanced by effectively increasing the active area of the device by integrating multiple sets of electrodes across the channel. Further enhancements of sensitivity may be achieved by adopting an immobilization procedure which results in antibodies being immobilized predominantly on the gold electrodes, as opposed to the entire channel length. Multiple recycling of the solution in the channel may also help with capturing cells which may pass through the channel without attaching to the electrodes. Upon making such improvements to the device, we envision and recognize achieving detection limits comparable to those reported most recently in the literature, which is near $10^1$ CFU/ml in solution. This method of detection may be used for development of a handheld device for point of care diagnostics.

Example 1

In this example, we describe a representative kinase assay for the human tyrosine kinase Abl. The reaction chamber was fabricated by bonding a PDMS microchannel to a glass slide using oxygen plasma. Abl peptide substrates were immobilized on the chamber surface using biotin-streptavidin chemistry in which the peptide was first biotinylated and then bound to the microchannel surface through streptavidin and biotinylated BSA that was passively adsorbed onto the glass. After the kinase reaction, the reaction chamber was washed once each with 10 mM Tris-HCl, pH 7.5/140 mM NaCl, 2M NaCl, 2M NaCl/1% H3PO4, and 10 mM Tris-HCl, pH 7.5/140 mM NaCl/0.05% Tween 20 (TBST) and blocked with 3% nonfat milk in TBST for one hour at room temperature. Phosphorylated Abl peptide substrates were detected using 2.8 μm paramagnetic beads (Invitrogen, protein G-coated) that were conjugated to anti-phosphotyrosine antibodies (Millipore, 4G10 Platinum), blocked in 3% NFM in TBST to minimize aggregation, and resuspended in TBST. Using these parameters, we have achieved a detection level of 10 aM (FIG. 6). Referring to FIG. 6, signal intensities were directly derived from number of beads bound. The titration curve demonstrates a detection limit of 10 aM.

Example 2

To evaluate the performance of our microfluidic platform, immunoassays detecting phospho-CrkL (a known target of Abl tyrosine kinase) recombinant protein and kinase assays detecting Abl tyrosine kinase activity were performed in both 96-well plate and our microfluidic chip format.

Comparison of Sandwich Immunoassay

For the 96-well plate assay, rabbit anti-CrkL monoclonal antibodies (clone Y244, Nevus Biologicals #NB 110-56895) were immobilized by overnight adsorption at 4° C. The wells were then blocked using 3% BSA, and the analyte sample was incubated for 12 hours at room temperature. Phospho-CrkL recombinant proteins present in the analyte sample was detected by incubating mouse anti-phosphotyrosine antibodies (clone 4G10, Millipore #05-1050, two hours at room temperature), followed by FITC-conjugated anti-mouse secondary antibodies (Jackson ImmunoResearch #715-095-150, two hours at room temperature) and quantifying the fluorescence using a plate reader (Perkin Elmer's Wallac Victor 2).

For the microfluidic chip assay, the same rabbit anti-CrkL monoclonal antibodies used in the 96-well plate assay were used to functionalize the surface of the microfluidic channel. However, because of the fluidics involved in our setup, the antibodies were immobilized using biotin-streptavidin chemistry. Biotinylated BSA (Sigma Aldrich #A6043, 1 mg/mL) was first allowed to adsorb (15 minutes, room temperature) onto the glass surface the microchannel. Streptavidin (Thermo Scientific #21125, 1 mg/mL) was next injected into the microchannel and allowed to bind the biotinylated BSA (15 minutes, room temperature), followed by biotin-conjugated anti-rabbit antibodies (Jackson ImmunoResearch #711-065-152, 30 minutes, room temperature). Anti-CrkL monoclonal antibodies (clone Y244, Novus Biologicals #NB110-56895) were then immobilized by binding to the anti-rabbit antibodies. The microchannels were blocked using 3% BSA, and the analyte sample was incubated for 1 hour at room temperature with a flow rate of 0.02 µl/min Phospho-CrkL recombinant proteins present in the analyte sample was detected using 2.8 µm beads (Protein-G Dynabeads, Invitrogen #100.04D) conjugated with the anti-phosphotyrosine antibodies (clone 4G10, Millipore #05-1050); beads were injected into the microfluidic channel, nonspecifically bound beads were washed away using PBST (Phosphate buffered saline with 0.01% Tween-20), and specifically bound beads were digitally counted.

Results (two biological replicates, three technical replicates) show that our microfluidic chip format enables the detection of ~$10^3$ fewer molecules in a one-hour assay compared to a 12-hour assay performed in 96-well plate format. 1 nM phospho-CrkL was also tested in a one-hour 96-well plate assay and 200 pM phospho-CrkL was tested in a 12-hour 96-well plate assay, however the fluorescence signals for both conditions were at background levels.

|  | 96-well plate format | Our format |
|---|---|---|
| Current limit of detection | 1 nM | 100 pM |
| Binding reaction time | 12 hours | 1 hour |
| Binding reaction volume | 100 µl | 1.2 µl |
| Number of molecules detected | $6 \times 10^{10}$ molecules | $7.2 \times 10^7$ molecules |

Comparison of Kinase Assay

For the 96-well plate assay, optimized peptide substrates for Abl, Abltide EAIYAAPFAKKK (SEQ ID NO:6), were immobilized onto the bottom surface of each well. Because of the small size of the peptide substrates, the peptides were immobilized using biotin-streptavidin chemistry. Biotinylated BSA (Sigma Aldrich #A6043) was first adsorbed (overnight, 4° C.) onto the surface the 96-well plate. Streptavidin (Thermo Scientific #21125) was then incubated (overnight, 4° C.), followed by biotin-conjugated Abltides (Millipore #12-539, overnight, 4° C.). Abl kinase (Millipore #14-529) and 100 µM ATP were then added to the 96-well plate, and the kinase reaction was allowed to proceed for one hour at 30° C. Standard kinase buffer (20 mM Hepes, pH 7.4, 10 mM $MgCl_2$, 10 mM $MnCl_2$, 1 mM DTT, 0.1% Brij35) supplemented with phosphatase inhibitors (PhosSTOP, Roche #04906845001) was used. The kinase reaction was stopped using a series of washes: once each with TBS (Tris buffered saline) with 0.1% SDS, 2M NaCl, 2M NaCl with 1% $H_3PO_4$, and TBST (TBS with 0.01% Tween-20). The 96-well plate was then blocked with 3% nonfat milk, and any resulting phosphorylated peptide substrates were detected by incubating mouse anti-phosphotyrosine antibodies (clone 4G10, Millipore #05-1050, two hours, room temperature), followed by FITC-conjugated anti-mouse secondary antibodies (Jackson ImmunoResearch #715-095-150, two hours, room temperature). As with the immunoassay, fluorescence was quantified using a plate reader (Perkin Elmer's Wallac Victor 2).

For the microfluidic chip assay, the same optimized peptide substrates for Abl used in the 96-well plate assay were immobilized onto the bottom surface of each microfluidic channel using the same biotin-streptavidin immobilization chemistry. Biotinylated BSA (Sigma Aldrich #A6043) was first adsorbed (15 minutes, room temperature) onto the surface the microchannel. Streptavidin (Thermo Scientific #21125) was next incubated in the microchannel (15 minutes, room temperature), followed by biotin-conjugated Abltides (Millipore #12-539, overnight, 4° C.). Abl kinase (Millipore #14-529) and 100 µM ATP were injected into the microchannel at a flow rate of 0.02 µl/min, and as before, the kinase reaction was allowed to proceed for one hour at 30° C. Standard kinase buffer (20 mM Hepes, pH 7.4, 10 mM $MgCl_2$, 10 mM $MnCl_2$, 1 mM DTT, 0.1% Brij35) supplemented with phosphatase inhibitors (PhosSTOP, Roche #04906845001) was again used, and the kinase reaction was stopped using the same series of washes as those done with the 96-well plate. The microchannels were then blocked with 3% nonfat milk, and any resulting phosphorylated peptide substrates were detected using 2.8 µm beads (Protein-G Dynabeads, Invitrogen #100.04D) conjugated with the anti-phosphotyrosine antibodies (clone 4G10, Millipore #05-1050); beads were injected into the microfluidic channel, nonspecifically bound beads were washed using PBST (Phosphate buffered saline with 0.01% Tween-20), and specifically bound beads were digitally counted.

Results show that our microfluidic chip format enables the detection of ~$10^7$ fewer molecules compared to an assay performed in 96-well plate format.

|  | 96-well plate format | Our format |
|---|---|---|
| Current limit of detection | 10 pM | 10-100 aM |
| Kinase assay reaction time | 1 hour | 1 hour |
| Binding reaction volume | 100 µl | 1.2 µl |
| Number of molecules detected | $6 \times 10^8$ molecules | 7.2-72 molecules |

Example 3

Cell Capture

In order to demonstrate the ability of our technique for targeted cell detection, we performed an assay for detection and quantification of *Candida albicans* levels in a test sample.

Here we physically adsorbed mouse monoclonal antibody (Abcam part no: ab23368) against *C. albicans* on the glass surface, by incubating 5 µl per channel for 20 minutes (at a 1/10 dilution of the stock sample). After antibodies had been immobilized, we blocked the surface for non-specific binding using PBS with 1% BSA and 0.01% Tween. We injected 5 µl of yeast cells per channel into the device at a concentration of $3 \times 10^7$ cells/ml. The cells flowed through at a rate of 200 nl/min for 15 minutes. The captured cells (FIG. 23) were then quantified. The same experiment was performed with *Saccharomyces cerevisiae* as a control with a concentration of $1 \times 10^7$ cells/ml. The cells were quantified, and the results are shown in FIG. 24.

Figure 23:
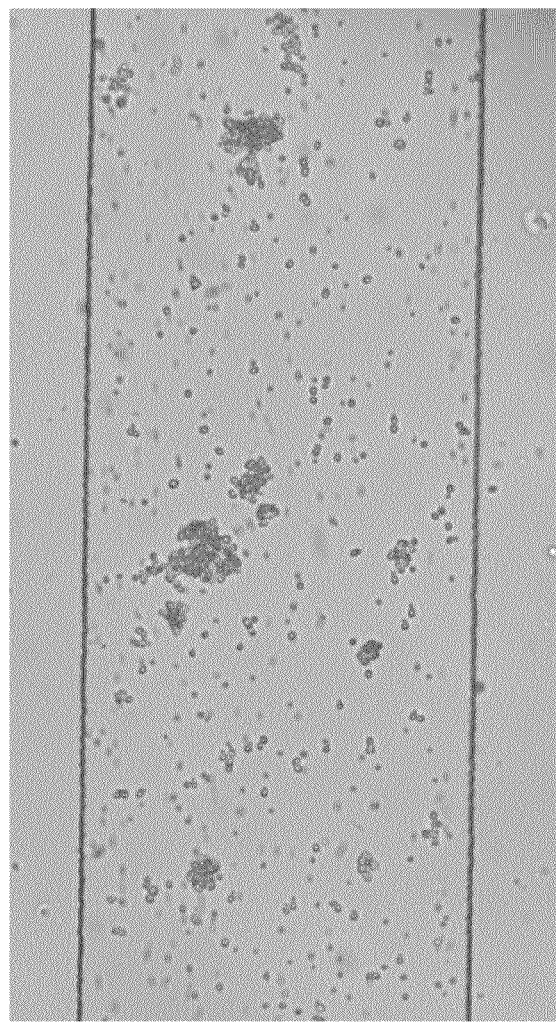
FIG. 23. Optical image of captured cells in channel.

Referring to FIG. 23, the sample was injected into the microchannel. *C. albicans* that are present in the sample will bind onto the surface of the channel. *S. cerevisiae* will not. The channel width was 300 µm and height was 25 µm. Each chip was composed of 16 parallel 8 mm long channels. Cells flowed through the device for 15 minutes. After cells had bound, a flow was applied so that the unbound cells were washed off. Specifically bound cells were quantified.

Figure 24:
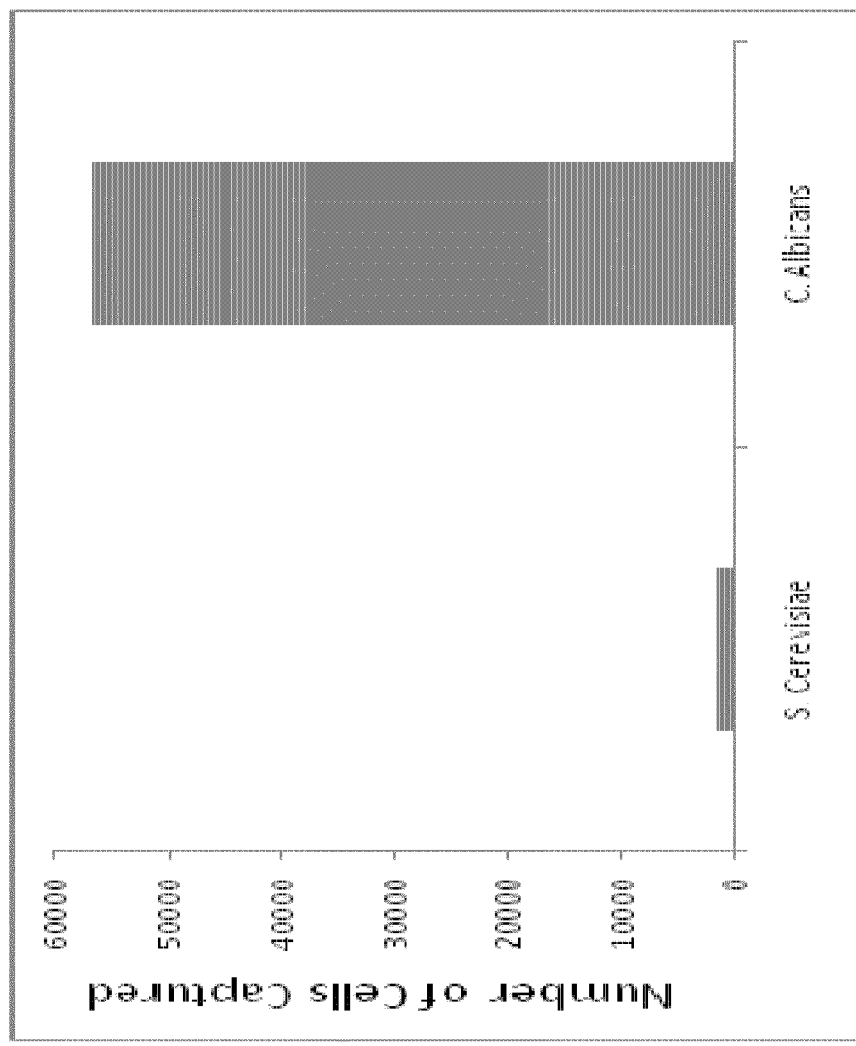
FIG. 24. Number of cells captured in channel.

Referring to FIG. 24, after 15 minutes of wash, captured cells were quantified. In the experimental protocol, we assayed a sample containing *C. albicans*. As a control experiment, we separately assayed a sample containing *S. cerevisiae* and compared the cell counts for the two samples. The amount of *S. cerevisiae* binding to the surface compared to the *C. albicans* was negligible, thus demonstrating the selectivity of our technique.

Example 4

Electrical Counting

Figure 25:
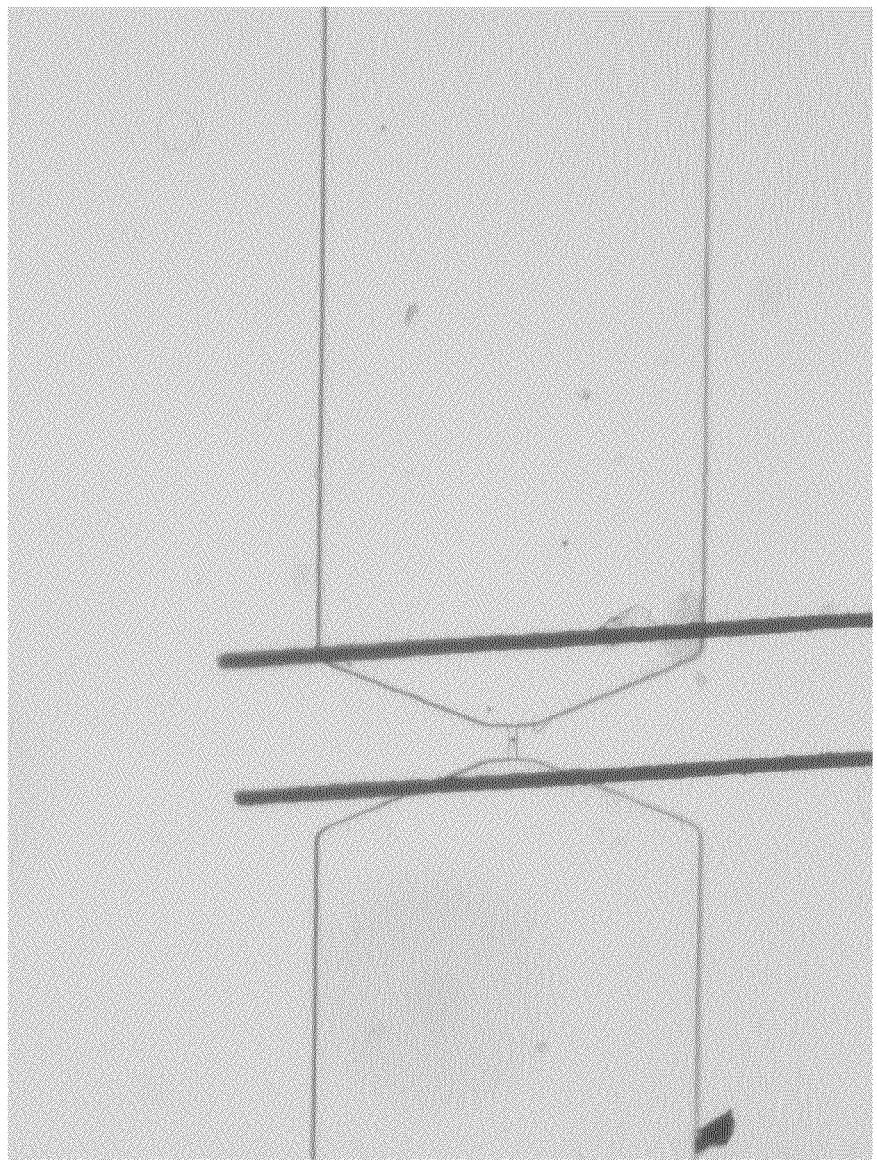
FIG. 25. Optical image of channel with micropore.

Given that good sensitivity was reached in Example 1 with 2.8 µm diameter beads, we designed and tailored our electrical sensor to be able to detect beads of this size. To do so, we fabricated a microfluidic channel integrated with electrodes. The channel was composed of a 8 µm×6 µm×30 µm (w×h×l) micropore with 300 µm wide and 20 µm high channels tapered to it from both sides as shown in FIG. 25. Electrodes that were 10 µm in width were spaced 100 µm apart. The advantage of using the tapered design is that while the electrodes are spaced far apart from each other, the dominant voltage drop between the electrodes is limited to that of the pore region.

Referring to FIG. 25, it shows a 300 µm wide and 20 µm high channel tapered to a 8 µm wide by 6 µm high by 30 µm long micropore. Electrodes are 10 µm wide spaced 100 µm apart from each other.

We measured the signal using a lock-in approach. A sinusoidal wave of 48 mV at 100 kHz was applied to the left electrode. The right electrode was connected to a lock-in-amplifier (Stanford Research Systems, part no. SR 830), which detected the 100 kHz signal and measured the amplitude of the wave. The data were collected with a data acquisition card and read by a Labview program. A baseline drift removal algorithm was written in Matlab code to remove the baseline drift.

Figure 26:
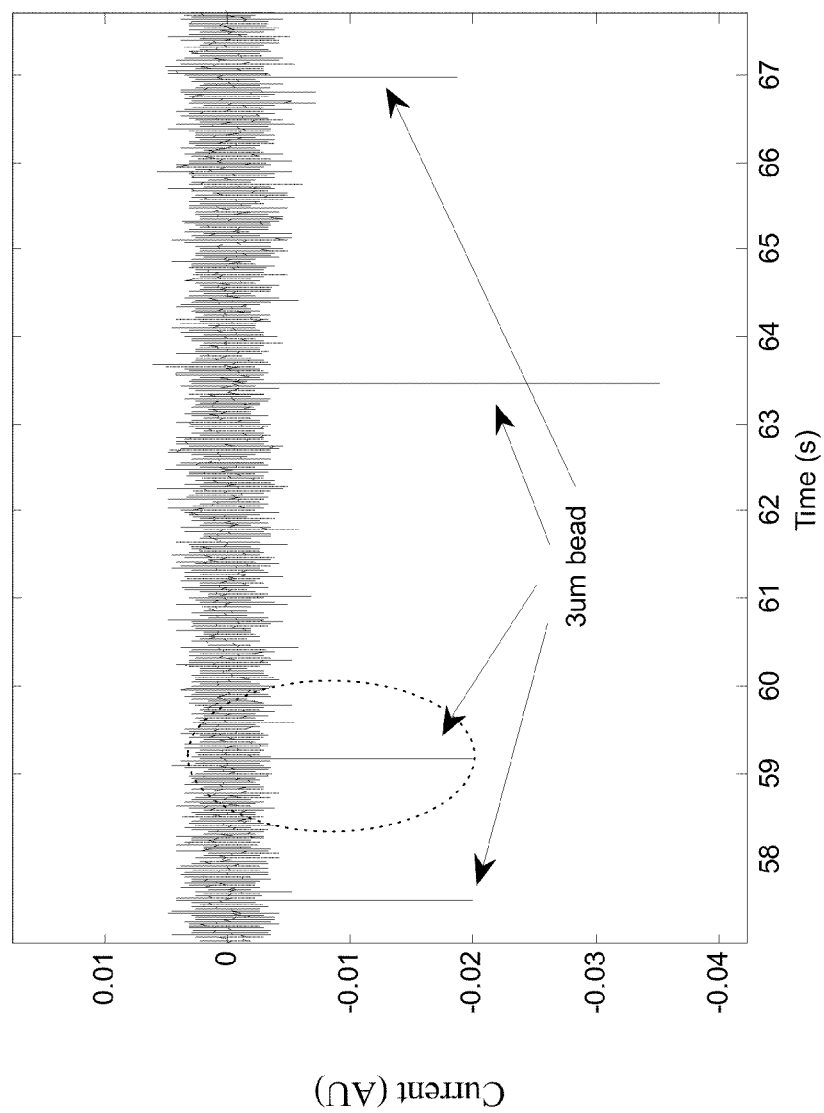
FIG. 26. Current as a function of time as beads pass through micropore.
Figure 27:
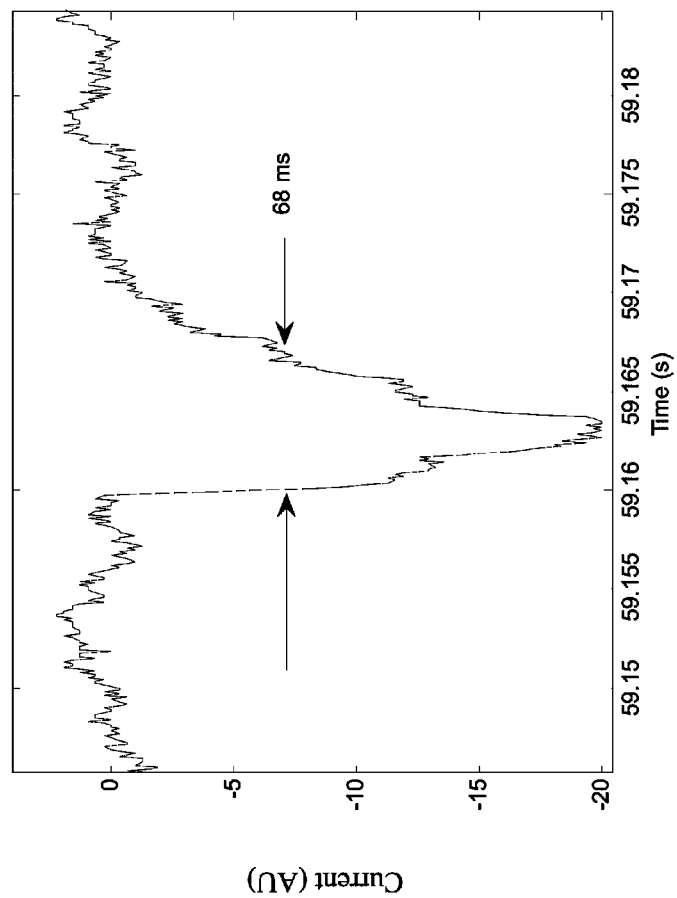
FIG. 27. Zoomed in view of pulse circled in FIG. 26 representing drop in current as bead passes through micropore.

In order to test the ability of our device to count beads, we suspended 2.8 µm paramagnetic beads in 10% SDS, a buffer that could be used to elute beads from the surface of the channel. For verification, we optically monitored our micropore under an optical microscope as we monitored the impedance across the channel. This allowed us to be sure that the pulses that we saw in our current indeed corresponded to beads passing across the micropore. FIG. 26 shows representative data of electrical impedance being monitored as beads pass across the channel. The negative spikes in the current correspond to 2.8 µm beads. FIG. 27 shows a close up view of one of the peaks. The time of flight for the bead is roughly 68 ms. Here, we have demonstrated electrical counting of 2.8 µm beads.

Referring to FIG. 26, it shows representative data of current measured across the micropore as 2.8 µm beads suspended in 10% SDS pass through one by one. The signal in the negative direction represents the passing through the micropore of a 2.8 µm bead.

Referring to FIG. 27, it shows a zoomed in view $\times 10^{-3}$ of the pulse circled in FIG. 26 representing a drop in the current as a 2.8 µm bead passes through the micropore. The time of flight for the bead happens to be roughly 68 ms.

Example 5

Cascaded Filters

In order to integrate the reaction chamber with the electrical sensor so that beads can be quantified electrically, several different approaches for integrating the two can be used. Here we discuss two of the devices we have implemented. These microchannels were fabricated in PDMS, and the molds were patterned onto a silicon substrate using SU-8 photoresist. One problem to be solved for smaller channel sizes is to prevent channel clogging. This can be done in many ways. One approach involves a separate waste channel along with cascaded filters. The unbound beads are washed off of the reaction chamber surface and redirected into the waste channel. Afterwards the specifically bound beads are eluted from the surface of the channel using 10% SDS. The eluted beads are directed into the counting micropore which is preceded by a cascade of filters gradually reducing in size such that any particles larger than the micropore size are blocked before they reach the counting micropore.

Below we show optical micrographs of two different possible implementations of the cascaded filters. These devices integrating the reaction chamber with the electrical sensor demonstrate one approach to solving the problem for smaller channel sizes to prevent channel clogging.

Figure 28:
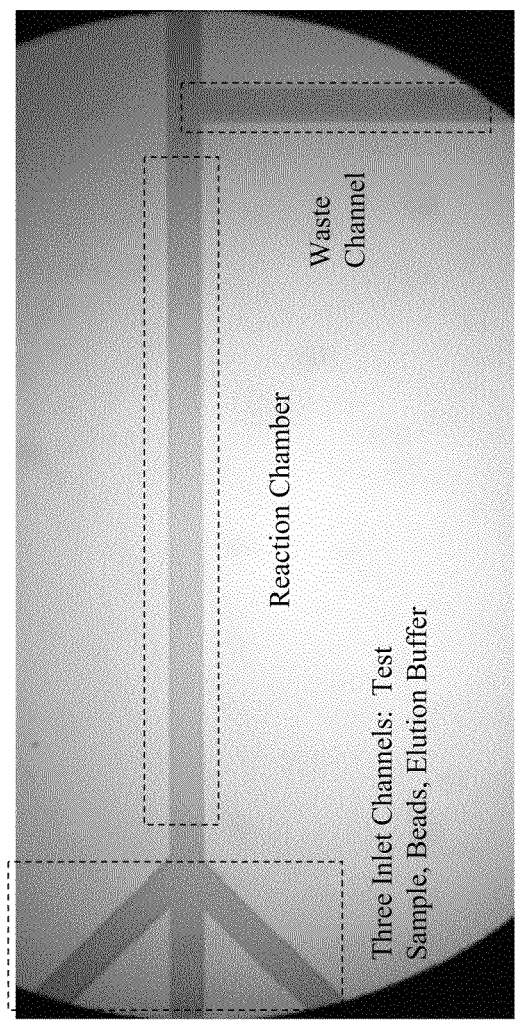
FIG. 28. Optical image of inlet, reaction chamber, and waste channel.
Figure 29:
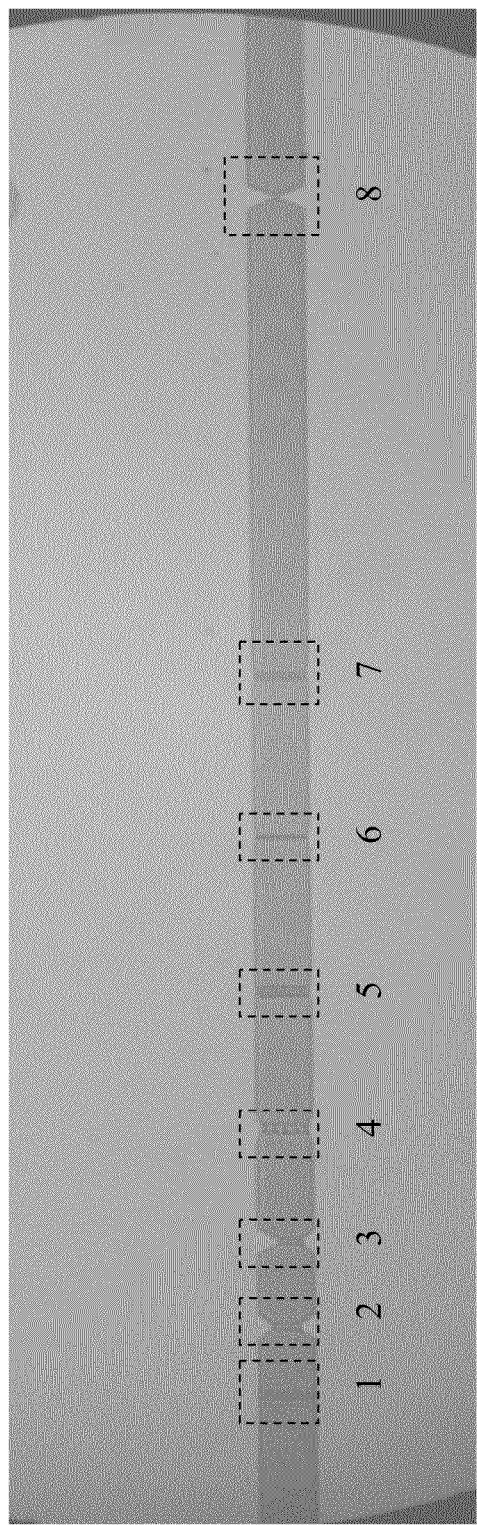
FIG. 29. Optical image of cascaded filters (design #1) and counting micropore.
Figure 30:
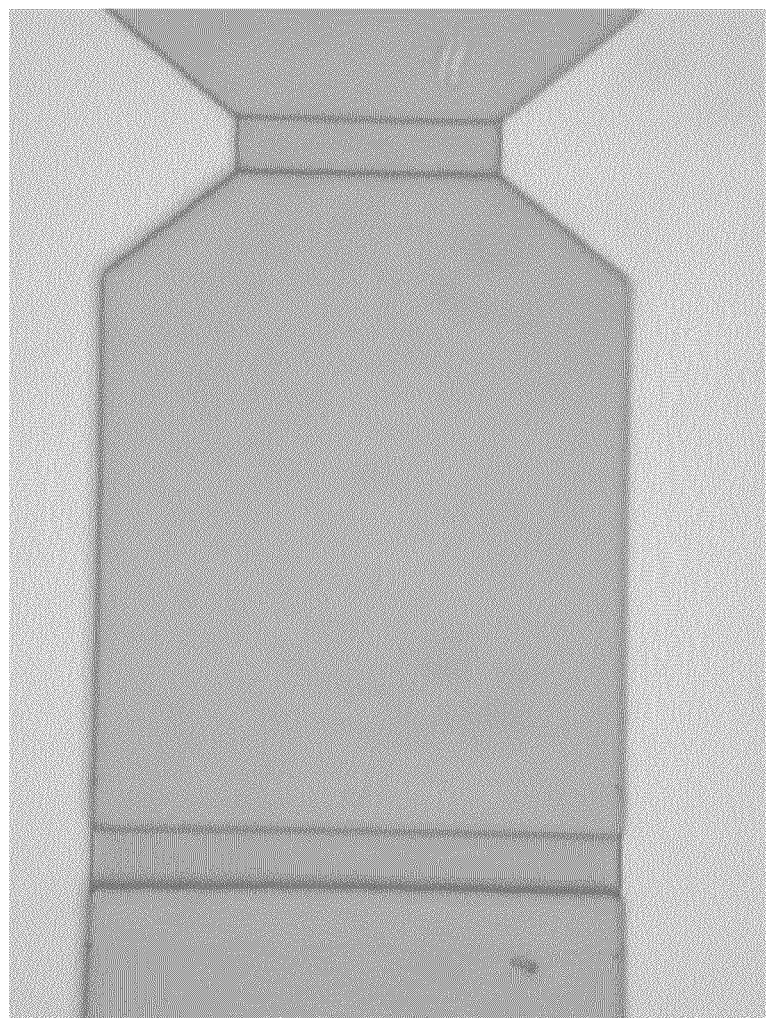
FIG. 30. Zoomed in optical image of filter one and two. The first is 300 μm in width. The second is 150 μm in width.
Figure 31:
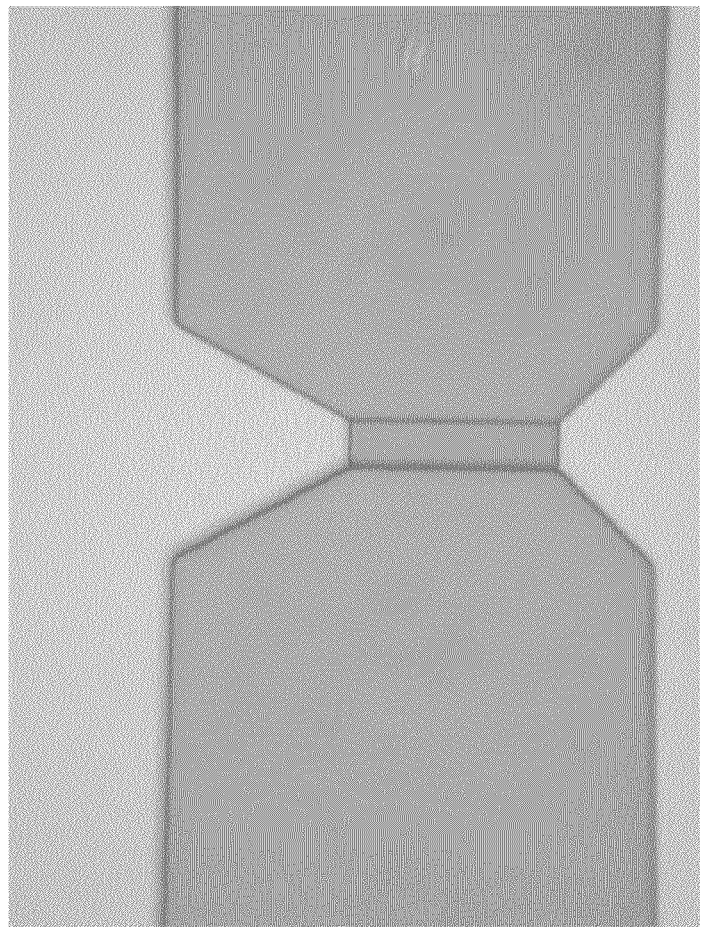
FIG. 31. Zoomed in optical image of filter three; it is 150 μm in width.
Figure 32:
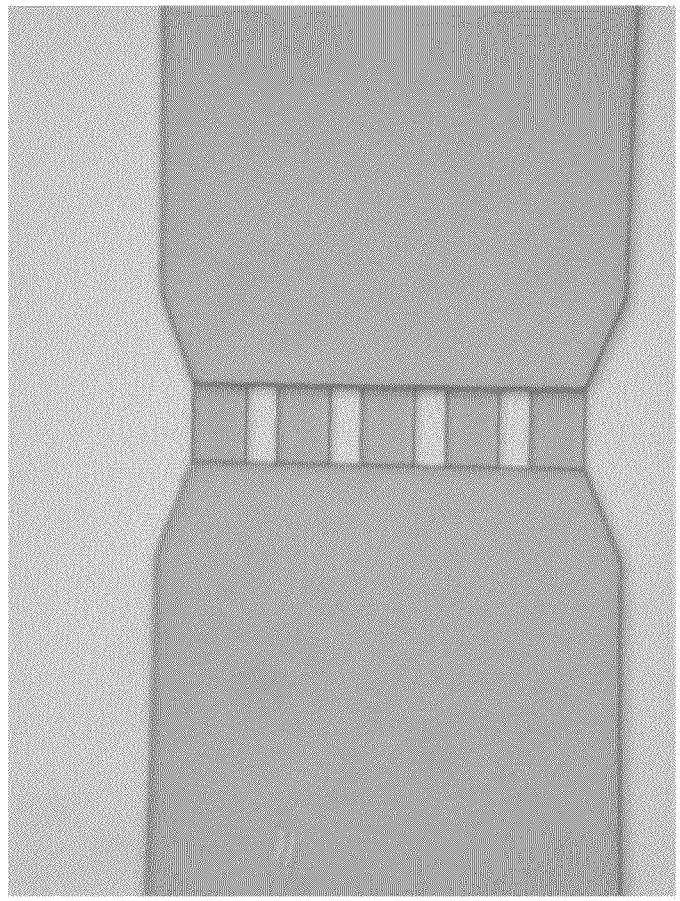
FIG. 32. Zoomed in optical image of filter four; it is 50 μm in width.
Figure 33:
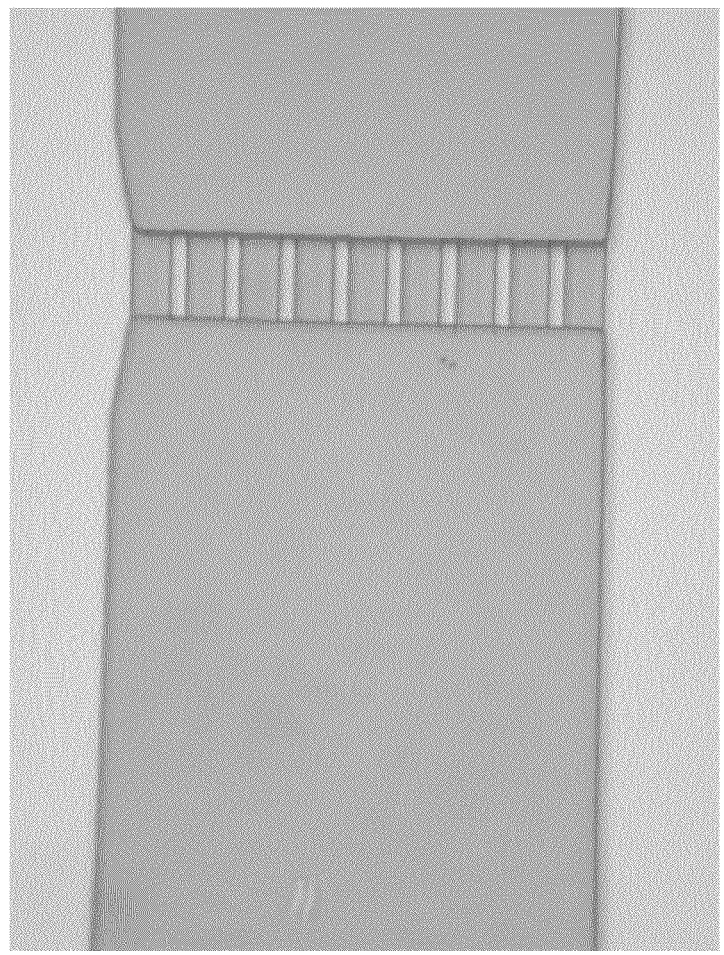
FIG. 33. Zoomed in optical image of filter five; it is 25 μm in width.
Figure 34:
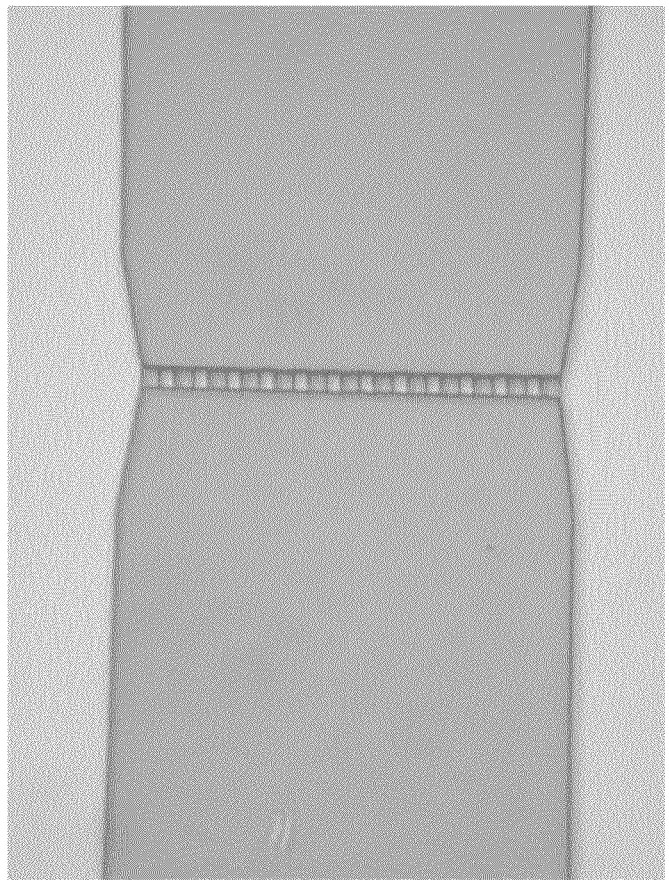
FIG. 34. Zoomed in optical image of filter six; it is 8 μm in width.
Figure 35:
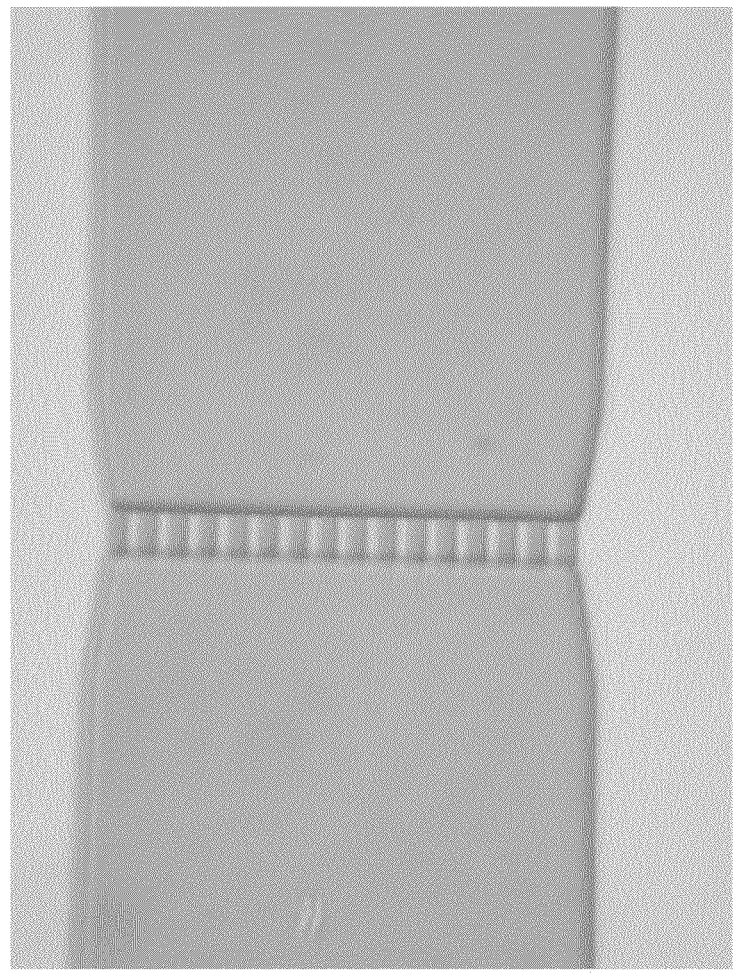
FIG. 35. Zoomed in optical image of filter seven; it is 8 µm in width.
Figure 36:
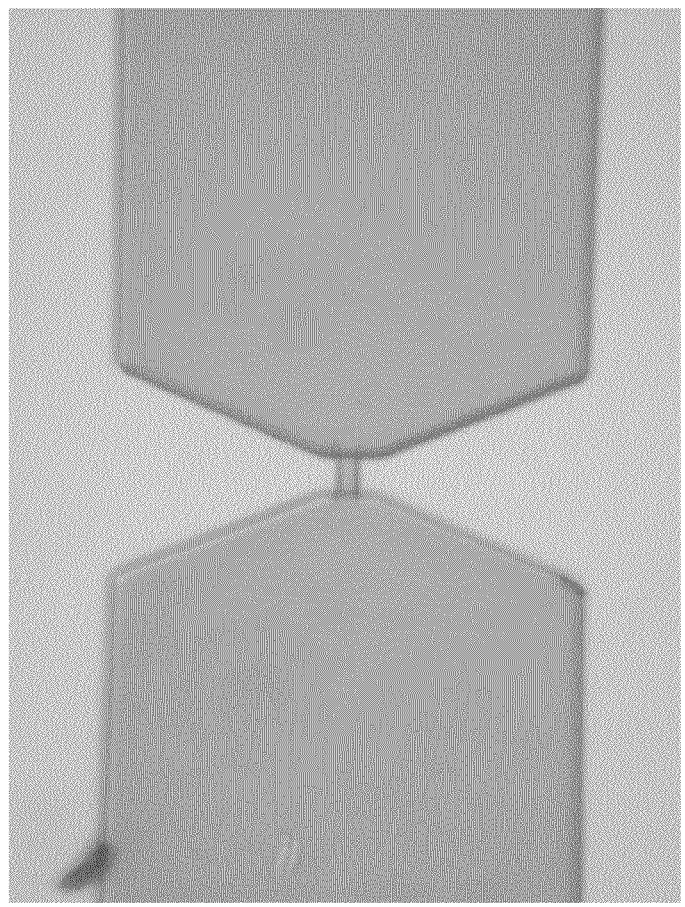
FIG. 36. Optical image of counting micropore itself.

FIGS. 28 to 36 show the implementation for the first design. In this implementation, the cascaded filters are pores that gradually reduce in size as they get closer to the electrical sensor. FIGS. 28 and 29 are optical images showing the inlet, reaction chamber, and waste channel, and the cascaded filters and counting micropore, respectively. FIGS. 30 to 35 show zoomed in optical images of the various filters as they get smaller, finally approaching the size of the counting micropore itself. All of the filter pores are 6 µm in height. FIG. 36 shows a zoomed in optical image of the 8 µm counting micropore.

Figure 37:
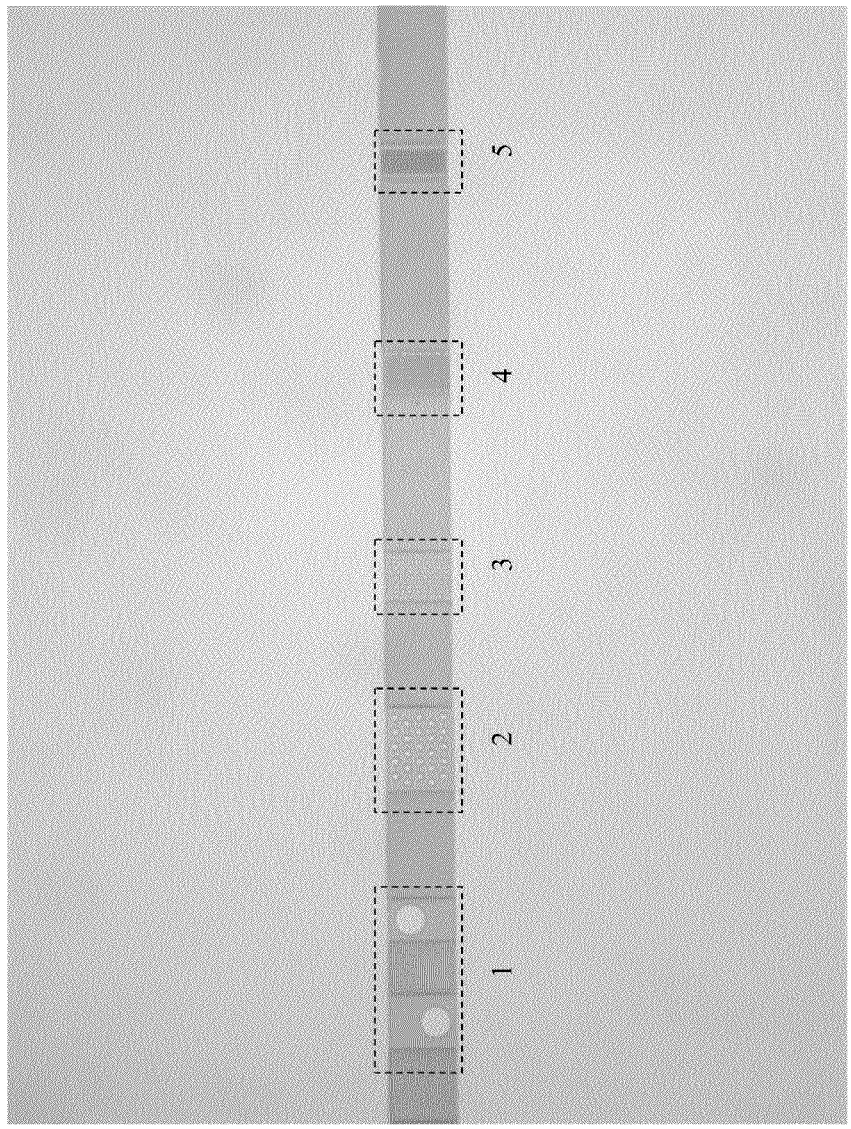
FIG. 37. Optical image of cascaded filters (design #2).
Figure 38:
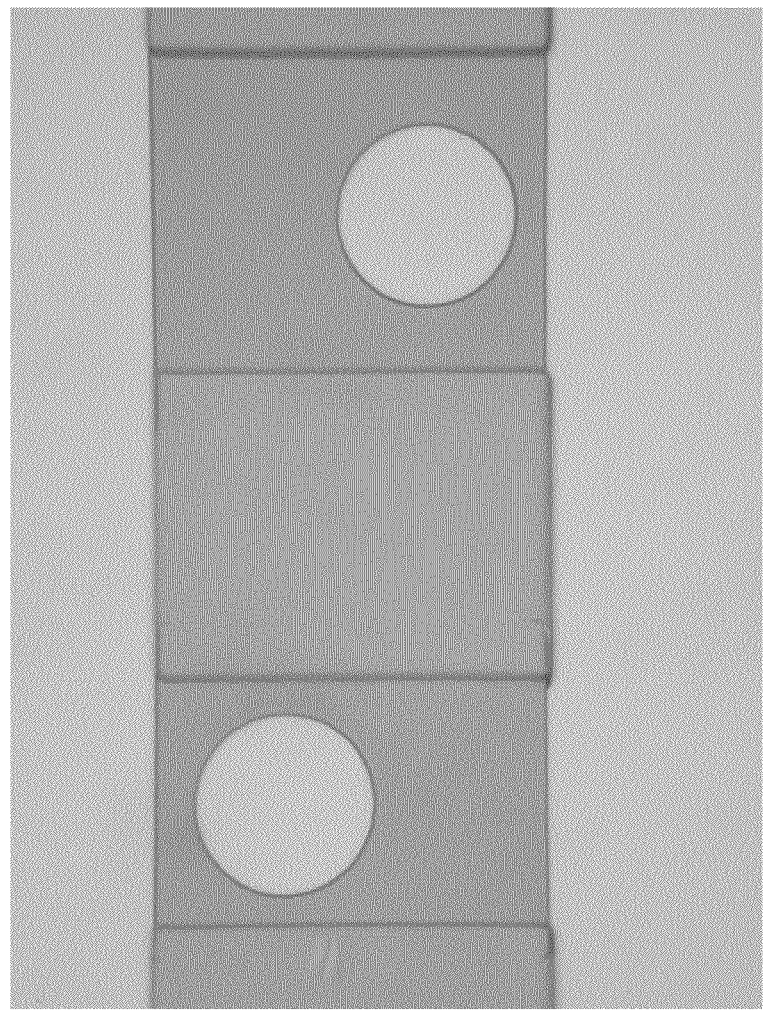
FIG. 38. Zoomed in optical image of filter one; the pillars are 150 µm in diameter.
Figure 39:
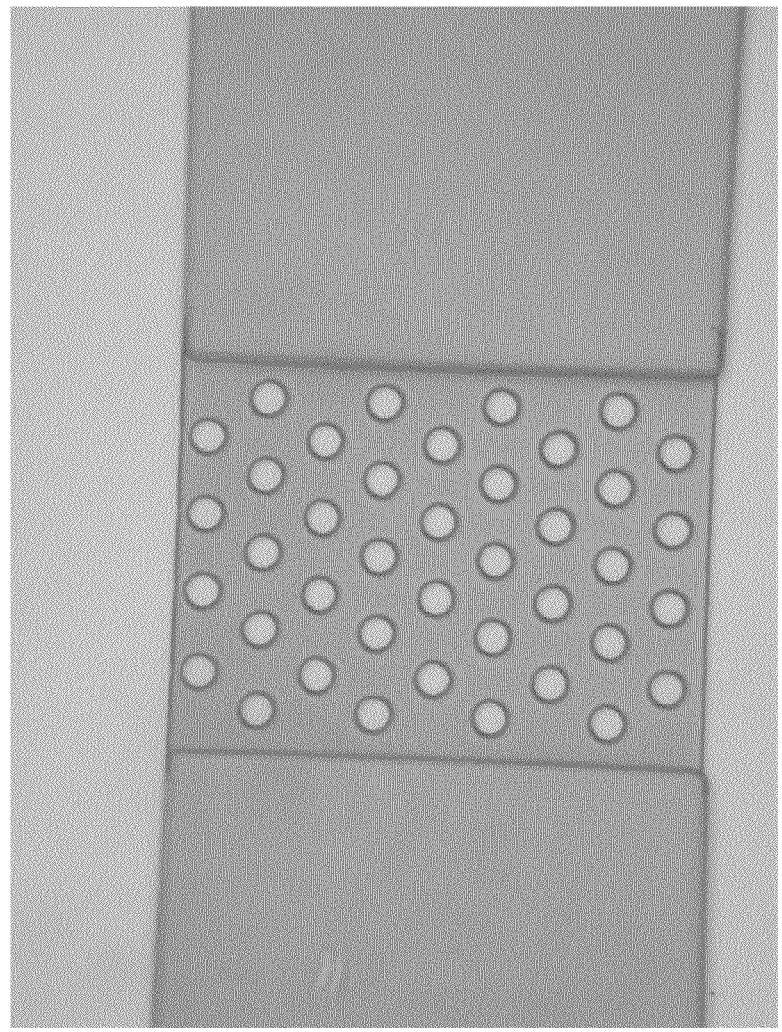
FIG. 39. Zoomed in optical image of filter three; the pillars are 22 µm in diameter.
Figure 40:
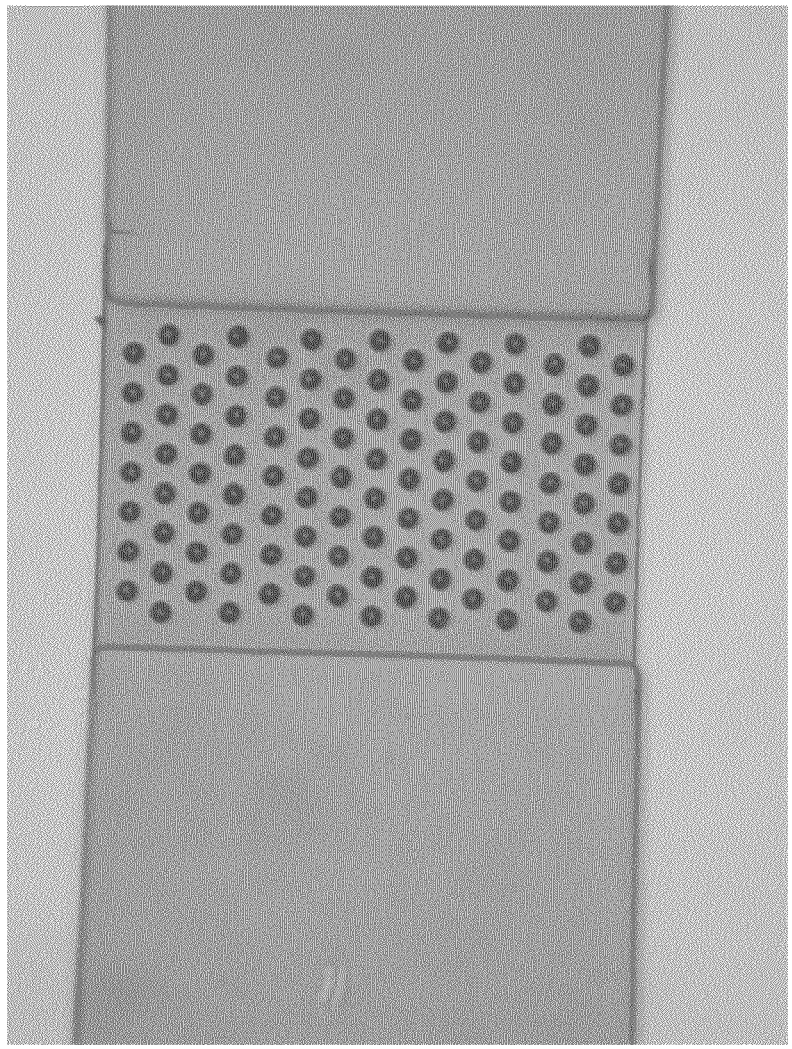
FIG. 40. Zoomed in optical image of filter four; the pillars are 8 µm in diameter.
Figure 41:
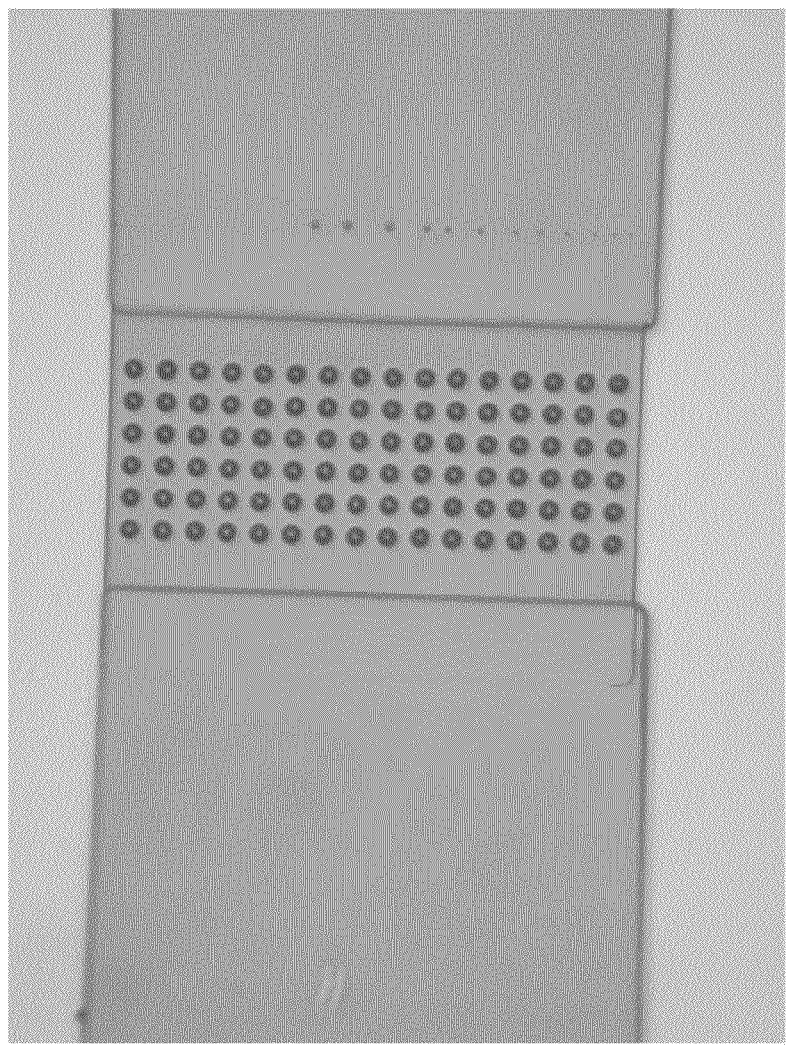
FIG. 41. Zoomed in optical image of filter five; the pillars are 8 µm in diameter.

FIGS. 37 to 41 show the implementation for the second design. In this implementation, the cascaded filters are pillars that gradually reduce in size and increase in density as they approach the electrical sensor. FIG. 37 is an optical image showing a zoomed out view of the cascade of filters. FIGS. 38 to 41 are optical images showing zoomed in views of the pillars as they get smaller and denser. All of the pillars are 6 µm in height. In the largest set of pillars, the pillars are 150 µm in diameter and 6 µm in height. In the smallest set, the pillars are 8 µm in diameter and spaced 8 µm apart to filter out anything larger in size than 8 µm.

These examples and embodiments are illustrative and are not to be read as limiting the scope of the invention as it is defined by this specification and the appended claims.

All references cited in this specification are incorporated herein by reference.

What is claimed is:

1. A method for detecting or determining the concentration of biomolecules in an analyte comprising:
   a) moving fluid containing a microsphere through a first microfluidic channel, wherein a surface of said channel is functionalized with at least one molecule selected to interact with a biomolecule, said channel being configured to interact with a microsphere, wherein a surface of said microsphere is functionalized with at least one molecule selected to interact with said biomolecule, whereby said microsphere interacts with said channel;
   b) eluting a microsphere interacting with said biomolecule from said first microfluidic channel and moving fluid containing said microsphere upon elution from said first microfluidic channel through a second microfluidic channel in fluid communication with said first microfluidic channel;
   c) measuring a change in electrical impedance or optical microscopy across said second microfluidic channel as said microsphere moves through said second microfluidic channel; and
   (d) correlating changes measured in step (c) for counting a plurality of microspheres moving through said second channel to detect or determine the concentration of biomolecules.

2. A method for detecting or determining the concentration of nucleic acids in an analyte comprising:
   a) moving fluid containing a microsphere through a first microfluidic channel, wherein a surface of said channel is functionalized with at least one probe nucleic acid selected to interact with a target nucleic acid, said channel being configured to interact with a microsphere, wherein a surface of said microsphere is functionalized with at least one molecule selected to interact with said target nucleic acid, whereby said microsphere interacts with said channel;
   b) eluting a microsphere interacting with said biomolecule from said first microfluidic channel and moving fluid containing said microsphere upon elution from said first microfluidic channel through a second microfluidic channel in fluid communication with said first microfluidic channel;
   c) measuring a change in electrical impedance or optical microscopy across said second microfluidic channel as said microsphere moves through said second microfluidic channel; and
   (d) correlating changes measured in step (c) for counting a plurality of microspheres moving through said second channel to detect or determine the concentration of nucleic acids.

3. A method for detecting or determining the concentration of enzymes in an analyte comprising:
   a) moving fluid containing a microsphere through a first microfluidic channel, wherein a surface of said channel is functionalized with at least one substrate selected to be catalyzed by said enzyme, said channel being configured to interact with a microsphere, wherein a surface of said microsphere is functionalized with at least one molecule selected to interact with a product of catalysis of said substrate by said enzyme, whereby said microsphere interacts with said channel;
   b) eluting a microsphere interacting with said biomolecule from said first microfluidic channel and moving fluid containing said microsphere upon elution from said first microfluidic channel through a second microfluidic channel in fluid communication with said first microfluidic channel;
   c) measuring a change in electrical impedance or optical microscopy across said second microfluidic channel as said microsphere moves through said second microfluidic channel; and
   (d) correlating changes measured in step (c) for counting a plurality of microspheres moving through said second channel to detect or determine the concentration of enzymes.

4. A method for detecting or determining the concentration of enzymes in an analyte comprising:
   a) moving fluid containing a microsphere through a first microfluidic channel, wherein a surface of said channel is functionalized with at least one molecule selected to interact with a product of catalysis of a substrate by said enzyme, said channel being configured to interact with a microsphere, wherein a surface of said microsphere is functionalized with at least one substrate selected to be catalyzed by said enzyme, whereby said microsphere interacts with said channel;
   b) eluting a microsphere interacting with said biomolecule from said first microfluidic channel and moving fluid containing said microsphere upon elution from said first microfluidic channel through a second microfluidic channel in fluid communication with said first microfluidic channel;
   c) measuring a change in electrical impedance or optical microscopy across said second microfluidic channel as said microsphere moves through said second microfluidic channel; and
   (d) correlating changes measured in step (c) for counting a plurality of microspheres moving through said second channel to detect or determine the concentration of enzymes.

5. A method for detecting or determining the concentration of cells in an analyte comprising:
   a) moving fluid containing a cell through a first microfluidic channel, wherein a surface of said channel is functionalized with at least one molecule selected to interact with a biomolecule on a surface of said cell, said channel being configured to interact with said cell, whereby said cell interacts with said channel;
   b) eluting a microsphere interacting with said biomolecule from said first microfluidic channel and moving fluid containing said cell upon elution from said first microfluidic channel through a second microfluidic channel in fluid communication with said first microfluidic channel;
   c) measuring a change in electrical impedance or optical microscopy across said second channel as said cell moves through said second channel; and (d) correlating changes measured in step (c) for counting a plurality of microspheres moving through said second channel to detect or determine the concentration of cells.

6. The method of claim 1, wherein said at least one molecule is an antibody.

7. The method of claim 1, wherein said first microfluidic channel is fabricated in polydimethylsiloxane (PDMS).

8. The method of claim 1, wherein said second microfluidic channel is fabricated in polydimethylsiloxane (PDMS).

9. The method of claim 1, wherein a molded PDMS slab comprising said second microfluidic channel is sealed to a glass chip with prefabricated electrodes.

10. A method according to claim 1 further comprising multiplexing a plurality of steps a, b, and c through multiple channels.

11. The method of claim 1, wherein said biomolecules are proteins.

* * * * *

UNITED STATES PATENT AND TRADEMARK OFFICE
CERTIFICATE OF CORRECTION

| | | |
|---|---|---|
| PATENT NO. | : 8,614,056 B2 | |
| APPLICATION NO. | : 13/070002 | |
| DATED | : December 24, 2013 | |
| INVENTOR(S) | : Ronald W. Davis et al. | |

It is certified that error appears in the above-identified patent and that said Letters Patent is hereby corrected as shown below:

In the Specification

Column 1, line 19, cancel the text beginning with "Statement Regarding Government Support" to and ending "in this invention" in column 1, line 25.

Signed and Sealed this
Thirty-first Day of March, 2015

Michelle K. Lee
*Director of the United States Patent and Trademark Office*

SEQUENCE LISTING

<160> NUMBER OF SEQ ID NOS: 6

<210> SEQ ID NO 1
<211> LENGTH: 15
<212> TYPE: PRT
<213> ORGANISM: Artificial
<220> FEATURE:
<223> OTHER INFORMATION: Synthetic

<400> SEQUENCE: 1

Lys Val Glu Lys Ile Gly Glu Gly Thr Tyr Gly Val Val Tyr Lys
1               5                   10                  15

<210> SEQ ID NO 2
<211> LENGTH: 62
<212> TYPE: DNA
<213> ORGANISM: Artificial
<220> FEATURE:
<223> OTHER INFORMATION: Synthetic

<400> SEQUENCE: 2
cccccccccc tttttttttt tttttttttt tttttttttt tttttttttt tttttttttt      60
tt                                                                     62

<210> SEQ ID NO 3
<211> LENGTH: 62
<212> TYPE: DNA
<213> ORGANISM: Artificial
<220> FEATURE:
<223> OTHER INFORMATION: Synthetic

<400> SEQUENCE: 3
cccccccccc aaaaaaaaaa aaaaaaaaaa aaaaaaaaaa aaaaaaaaaa aaaaaaaaaa      60
aa                                                                     62

<210> SEQ ID NO 4
<211> LENGTH: 45
<212> TYPE: DNA
<213> ORGANISM: Artificial
<220> FEATURE:
<223> OTHER INFORMATION: Synthetic

<400> SEQUENCE: 4
aggtgtgggg tgatcatttg tcagtgtgag ggagtgtggt agtgc                      45

<210> SEQ ID NO 5
<211> LENGTH: 45
<212> TYPE: DNA
<213> ORGANISM: Artificial
<220> FEATURE:
<223> OTHER INFORMATION: Synthetic

<400> SEQUENCE: 5
acacctgcac taccacactc cctcacactg acaaatgatc acccc                      45

<210> SEQ ID NO 6
<211> LENGTH: 12
<212> TYPE: PRT
<213> ORGANISM: Artificial
<220> FEATURE:
<223> OTHER INFORMATION: Synthetic

```
<400> SEQUENCE: 6

Glu Ala Ile Tyr Ala Ala Pro Phe Ala Lys Lys Lys
1               5                  10
```